（12）United States Patent
Hasegawa et al.

US008791290B2

(10) Patent No.: US 8,791,290 B2
(45) Date of Patent: Jul. 29, 2014

(54) ACETAL COMPOUND, POLYMER, RESIST COMPOSITION, AND PATTERNING PROCESS

(75) Inventors: Koji Hasegawa, Joetsu (JP); Jun Hatakeyama, Joetsu (JP); Takeshi Nagata, Joetsu (JP); Seiichiro Tachibana, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 315 days.

(21) Appl. No.: 13/069,824

(22) Filed: Mar. 23, 2011

(65) Prior Publication Data

US 2011/0236831 A1    Sep. 29, 2011

(30) Foreign Application Priority Data

Mar. 24, 2010   (JP) ................. 2010-067769

(51) Int. Cl.
    *C07C 67/02*  (2006.01)
(52) U.S. Cl.
    USPC ......................................... 560/260
(58) Field of Classification Search
    USPC ........ 430/285.1, 325; 526/268, 270; 560/219, 560/220
    See application file for complete search history.

(56) References Cited

U.S. PATENT DOCUMENTS

| 6,448,420 B1 | 9/2002 | Kinsho et al. |
|---|---|---|
| 6,830,866 B2 | 12/2004 | Kobayashi et al. |
| 7,514,204 B2 | 4/2009 | Hatakeyama et al. |
| 7,537,880 B2 | 5/2009 | Harada et al. |
| 7,598,016 B2 | 10/2009 | Kobayashi et al. |
| 7,622,242 B2 | 11/2009 | Hatakeyama et al. |
| 7,642,034 B2 | 1/2010 | Hatakeyama et al. |
| 7,670,750 B2 | 3/2010 | Harada et al. |
| 7,759,047 B2 | 7/2010 | Hatakeyama et al. |
| 7,771,913 B2 | 8/2010 | Kaneko et al. |
| 2007/0003867 A1 | 1/2007 | Hatakeyama et al. |
| 2008/0090172 A1 | 4/2008 | Hatakeyama et al. |
| 2008/0318171 A1 | 12/2008 | Tsubaki |
| 2009/0011365 A1 | 1/2009 | Kobayashi et al. |
| 2009/0042147 A1 | 2/2009 | Tsubaki |
| 2009/0280434 A1 | 11/2009 | Harada et al. |
| 2010/0040972 A1 | 2/2010 | Tarutani et al. |
| 2010/0330507 A1 | 12/2010 | Tsubaki et al. |

FOREIGN PATENT DOCUMENTS

| JP | 2000-327633 A | 11/2000 |
|---|---|---|
| JP | 2003-066612 A | 3/2003 |
| JP | 3790649 B2 | 6/2006 |
| JP | 2007-025634 A | 2/2007 |
| JP | 2007-297590 A | 11/2007 |
| JP | 2007-316448 A | 12/2007 |
| JP | 2008-003569 A | 1/2008 |
| JP | 2008-081716 A | 4/2008 |
| JP | 2008-107443 A | 5/2008 |
| JP | 2008-111089 A | 5/2008 |
| JP | 2008-111103 A | 5/2008 |
| JP | 2008-122932 A | 5/2008 |
| JP | 2008-203639 A | 9/2008 |
| JP | 2008-239918 A | 10/2008 |
| JP | 2008-281974 A | 11/2008 |
| JP | 2008-281975 A | 11/2008 |
| JP | 2008-281980 A | 11/2008 |
| JP | 2008-309878 A | 12/2008 |
| JP | 2008-309879 A | 12/2008 |
| JP | 2009-025707 A | 2/2009 |
| JP | 2009-025723 A | 2/2009 |
| JP | 2009-031767 A | 2/2009 |
| JP | 2009-053657 A | 3/2009 |
| JP | 2009-098638 A | 5/2009 |
| JP | 2009-276363 A | 11/2009 |
| WO | WO 2011/105626 A1 * | 2/2011 |
| WO | WO 2011 105626 * | 9/2011 |

OTHER PUBLICATIONS

Koji Arimatsu et al.; "Sensitivity Enhancement of Chemical-Amplification-Type Photoimaging Materials by Acetoacetic Acid Derivatives", Journal of Photopolymer Science and Technology, 1995, vol. 8, No. 1, pp. 43-46.
Koji Arimatsu et al.; "Effect of Phenolic Hydroxyl Residues on the Improvement of Acid-Proliferation-Type Photoimaging Materials", Journal of Photopolymer Science and Technology, 1996, vol. 9, No. 1, pp. 29-30.
Hiroko Nakamura et al.; "Contact Hole Formation by Multiple Exposure Technique in Ultra-low K1 Lithography", Proc. of SPIE, vol. 5377, pp. 255-263, 2004.
Shuji Nakao et al.; "0.12um Hole Pattern Formation by KrF Lithography for Giga Bit DRAM", IEEE IEDM Digest, 1996, pp. 61-64.
D.C. Owe-Yang et al.; "Double Exposure for the Contact Layer of the 65-nm Node", 2005, Proc. of SPIE, vol. 5753, pp. 171-180.
V. Truffert et al.; "Ultimate Contact Hole Resolution Using Immersion Lithography with Line/Space Imaging", 2009, Proc. of SPIE, vol. 7274, pp. 72740N1-72740N12.

* cited by examiner

*Primary Examiner* — Brandon Fetterolf
*Assistant Examiner* — Blaine G Doletski
(74) *Attorney, Agent, or Firm* — Westerman, Hattori, Daniels & Adrian, LLP

(57) ABSTRACT

The invention provides an acetal compound containing an adamantane ring having an alcoholic hydroxyl group which is protected with an acetal group having a carbonyl moiety of branched structure. A photoresist film comprising a polymer comprising recurring units derived from the acetal compound and an acid generator is characterized by a high dissolution contrast when it is subjected to exposure and organic solvent development to form an image via positive/negative reversal.

4 Claims, 13 Drawing Sheets

PHOTORESIST COATING

PHOTORESIST EXPOSURE

ORGANIC SOLVENT DEVELOPMENT

ACETAL COMPOUND, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2010-067769 filed in Japan on Mar. 24, 2010, the entire contents of which are hereby incorporated by reference.

TECHNICAL FIELD

This invention relates to an acetal compound useful as a starting reactant for functional, pharmaceutical and agricultural chemicals, a polymer comprising recurring units derived from the acetal compound, a photoresist composition comprising the polymer, and a pattern forming process using the photoresist composition. The acetal compound is useful as a starting monomer for the preparation of a polymer that finds use as a base resin in a radiation-sensitive resist composition having high transparency to radiation with a wavelength of up to 500 nm, especially up to 300 nm, specifically KrF, ArF or $F_2$ laser radiation and improved development properties.

The invention also relates to a pattern forming process involving exposure of resist film, deprotection reaction with the aid of acid and heat, and development with an organic solvent to form a negative tone pattern in which the unexposed region is dissolved and the exposed region is not dissolved, and a resist composition for use in the process.

BACKGROUND ART

In the recent drive for higher integration and operating speeds in LSI devices, the pattern rule is made drastically finer. The photolithography which is currently on widespread use in the art is approaching the essential limit of resolution determined by the wavelength of a light source. As the light source used in the lithography for resist pattern formation, g-line (436 nm) or i-line (365 nm) from a mercury lamp was widely used in 1980's. Reducing the wavelength of exposure light was believed effective as the means for further reducing the feature size. For the mass production process of 64 MB dynamic random access memories (DRAM, processing feature size 0.25 μm or less) in 1990's and later ones, the exposure light source of i-line (365 nm) was replaced by a KrF excimer laser having a shorter wavelength of 248 nm. However, for the fabrication of DRAM with a degree of integration of 256 MB and 1 GB or more requiring a finer patterning technology (processing feature size 0.2 μm or less), a shorter wavelength light source was required. Over a decade, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required an advancement to reduce the wavelength of exposure light, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the development of $F_2$ lithography was abandoned and instead, the ArF immersion lithography was introduced.

In the ArF immersion lithography, the space between the projection lens and the wafer is filled with water having a refractive index of 1.44. The partial fill system is compliant with high-speed scanning and when combined with a lens having a NA of 1.3, enables mass production of 45-nm node devices.

One candidate for the 32-nm node lithography is lithography using extreme ultraviolet (EUV) radiation with wavelength 13.5 nm. The EUV lithography has many accumulative problems to be overcome, including increased laser output, increased sensitivity, increased resolution and minimized line edge or width roughness (LER, LWR) of resist film, defect-free MoSi laminate mask, reduced aberration of reflection mirror, and the like.

Another candidate for the 32-nm node lithography is high refractive index liquid immersion lithography. The development of this technology was abandoned because LUAG, a high refractive index lens candidate had a low transmittance and the refractive index of liquid did not reach the goal of 1.8.

The process that now draws attention under the above-discussed circumstances is a double patterning process involving a first set of exposure and development to form a first pattern and a second set of exposure and development to form a pattern between the first pattern features. A number of double patterning processes are proposed. One exemplary process involves a first set of exposure and development to form a photoresist pattern having lines and spaces at intervals of 1:3, processing the underlying layer of hard mask by dry etching, applying another layer of hard mask thereon, a second set of exposure and development of a photoresist film to form a line pattern in the spaces of the first exposure, and processing the hard mask by dry etching, thereby forming a line-and-space pattern at a half pitch of the first pattern. An alternative process involves a first set of exposure and development to form a photoresist pattern having spaces and lines at intervals of 1:3, processing the underlying layer of hard mask by dry etching, applying a photoresist layer thereon, a second set of exposure and development to form a second space pattern on the remaining hard mask portion, and processing the hard mask by dry etching. In either process, the hard mask is processed by two dry etchings.

As compared with the line pattern, the hole pattern is difficult to reduce the feature size. In order for the prior art method to form fine holes, an attempt is made to form fine holes by under-exposure of a positive resist film combined with a hole pattern mask. This, however, results in the exposure margin being extremely narrowed. It is then proposed to form holes of greater size, followed by thermal flow or RELACS® method to shrink the holes as developed. However, there is a problem that control accuracy becomes lower as the pattern size after development and the size after shrinkage differ greater and the quantity of shrinkage is greater. With the hole shrinking method, the hole size can be shrunk, but the pitch cannot be narrowed.

It is then proposed in Proc. SPIE, Vol. 5377, p. 255 (2004) that a pattern of X-direction lines is formed in a positive resist film using dipole illumination, the resist pattern is cured, another resist material is coated thereon, and a pattern of Y-direction lines is formed in the other resist film using dipole illumination, leaving a lattice-like line pattern, interstices of which provide a hole pattern. Although a hole pattern can be formed at a wide margin by combining X and Y lines and using dipole illumination featuring a high contrast, it is difficult to etch vertically staged line patterns at a high dimensional accuracy. It is proposed in IEEE IEDM Tech. Digest 61 (1996) to form a hole pattern by exposure of a negative resist film through a Levenson phase shift mask of X-direction lines combined with a Levenson phase shift mask of Y-direction lines. However, the crosslinking negative resist film has the drawback that the resolving power is low as compared with the positive resist film, because the maximum resolution of ultrafine holes is determined by the bridge margin.

A hole pattern resulting from a combination of two exposures of X- and Y-direction lines and subsequent image reversal into a negative pattern can be formed using a high-contrast line pattern of light. Thus holes having a narrow pitch and fine size can be opened as compared with the prior art.

Proc. SPIE Vol. 7274, p. 72740N (2009) reports three methods for forming hole patterns via image reversal. The three methods are: method (1) involving subjecting a positive resist material to two double-dipole exposures of X and Y lines to form a dot pattern, depositing a $SiO_2$ film thereon by LPCVD, and effecting $O_2$-RIE for reversal of dots into holes; method (2) involving forming a dot pattern by the same steps as in (1), but using a resist material designed to turn alkali-soluble and solvent-insoluble upon heating, coating a phenol-base overcoat film thereon, effecting alkaline development for image reversal to form a hole pattern; and method (3) involving double dipole exposure of a positive resist material and organic solvent development for image reversal to form holes.

The formation of negative pattern through organic solvent development is a traditional technique. A resist material comprising cyclized rubber is developed using an alkene such as xylene as the developer. An early chemically amplified resist material comprising poly(t-butoxycarbonyloxystyrene) is developed with anisole as the developer to form a negative pattern.

Recently a highlight is put on the organic solvent development again. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkali development and organic solvent development is under study.

As the ArF resist material for negative tone development with organic solvent, positive ArF resist compositions of the prior art design may be used. Pattern forming processes are described in JP-A 2008-281974, 2008-281975, 2008-281980, 2009-053657, 2009-025707, and 2009-025723.

These patent documents disclose resist materials for organic solvent development comprising a copolymer of hydroxyadamantane methacrylate, a copolymer of norbornane lactone methacrylate, a copolymer of methacrylate having acidic groups including carboxyl, sulfo, phenol, thiol and other groups substituted with two or more acid labile groups, and a copolymer of methacrylate having a cyclic acid-stable group ester, and pattern forming processes using the same.

Further, JP-A 2008-309878 discloses a process for forming a pattern through organic solvent development in which a protective film is applied onto a resist film. JP-A 2008-309879 discloses a topcoatless process for forming a pattern through organic solvent development in which an additive is added to a resist material so that the additive may segregate at the resist film surface after spin coating to provide the surface with improved water repellency.

CITATION LIST

Patent Document 1: JP-A 2008-281974
Patent Document 2: JP-A 2008-281975
Patent Document 3: JP-A 2008-281980
Patent Document 4: JP-A 2009-053657
Patent Document 5: JP-A 2009-025707
Patent Document 6: JP-A 2009-025723
Patent Document 7: JP-A 2008-309878
Patent Document 8: JP-A 2008-309879
Non-Patent Document 1: Proc. SPIE Vol. 5377, p. 255 (2004)
Non-Patent Document 2: IEEE IEDM Tech. Digest 61 (1996)
Non-Patent Document 3: Proc. SPIE Vol. 7274, p. 72740N (2009)

DISCLOSURE OF INVENTION

As compared with the positive resist system which becomes dissolvable in alkaline developer as a result of acidic carboxyl or analogous groups generating through deprotection reaction, the organic solvent development provides a low dissolution contrast. The alkaline developer provides an alkaline dissolution rate that differs by a factor of 1,000 or more between the unexposed and exposed regions whereas the organic solvent development provides a dissolution rate difference of only about 10 times. While Patent Documents 1 to 6 describe conventional photoresist materials of the alkaline aqueous solution development type, there is a demand for a novel material which can offer a significant dissolution contrast upon organic solvent development.

When holes are formed by negative development, regions surrounding the holes receive light so that excess acid is generated therein. It is then important to control acid diffusion because the holes are not opened if the acid diffuses inside the holes.

If the acid in the exposed region evaporates during PEB and deposits on the unexposed region, the positive pattern following alkaline development suffers from such drawbacks as rounded top of its profile and film slimming. An inverse phenomenon occurs on negative development with organic solvent, that is, holes are not opened or the opening size of holes at the top is reduced.

Coverage of a photoresist film with a protective film is effective for preventing evaporation of acid during PEB and for avoiding any hole opening failure following negative development, but still insufficient. The problem of hole opening failure following negative development is serious if a photoresist film is not covered with a protective film.

An object of the invention is to provide a photoresist composition which displays a high sensitivity and a high dissolution contrast during organic solvent development. Specifically, an object of the invention is to provide an acetal compound, a polymer prepared from the acetal compound and suited for use in photoresist compositions, a resist composition comprising the polymer as a base resin, and a pattern forming process using the resist composition.

The inventors have found that an acetal compound having the general formula (1) defined below is obtainable in a simple way, and that a resist composition comprising a polymer resulting from the acetal compound is improved in dissolution contrast during organic solvent development and forms a hole pattern via positive/negative reversal which is improved in sensitivity, resolution, and dimensional uniformity.

In one aspect, the invention provides an acetal compound having the general formula (1).

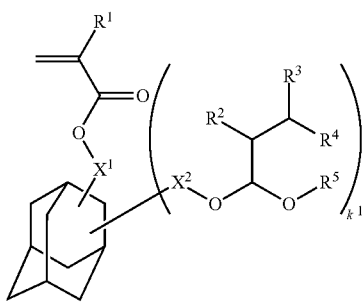

(1)

Herein $R^1$ is hydrogen, methyl or trifluoromethyl, $R^2$ is a straight, branched or cyclic monovalent $C_1$-$C_{10}$ hydrocarbon group, $R^3$ and $R^4$ are each independently hydrogen or a straight, branched or cyclic monovalent $C_1$-$C_{10}$ hydrocarbon group, $R^2$ and $R^3$ may bond together to form an aliphatic hydrocarbon ring with the carbon atoms to which they are attached, $X^1$ and $X^2$ are each independently a single bond or a straight or branched divalent $C_1$-$C_4$ hydrocarbon group, $R^5$ is a straight, branched or cyclic monovalent $C_1$-$C_{15}$ hydrocarbon group, and $k^1$ is an integer of 1 to 3.

In another aspect, the invention provides a polymer comprising recurring units having the general formula (2).

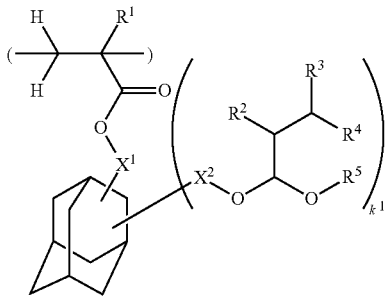

(2)

Herein $R^1$ to $R^5$, $X^1$, $X^2$, and $k^1$ are as defined above.

In a preferred embodiment, the polymer further comprises recurring units (b) of at least one type having a carboxyl group substituted with an acid labile group and/or recurring units (c) of at least one type derived from a monomer having an adhesive group selected from the class consisting of hydroxyl, cyano, carbonyl, ester, ether, lactone, carboxyl, and carboxylic anhydride groups.

In a further aspect, the invention provides a resist composition comprising a base resin comprising the polymer defined above, an acid generator, and an organic solvent.

In a still further aspect, the invention provides a pattern forming process comprising the steps of applying a resist composition comprising a base resin comprising the polymer defined above, an acid generator, and an organic solvent onto a substrate, heat treating the composition to form a resist film, exposing the resist film to high-energy radiation to define exposed and unexposed regions, heat treating, and developing the exposed film with an organic solvent developer to form a negative pattern wherein the unexposed region of film is dissolved and the exposed region of film is not dissolved.

In a preferred embodiment, the developer comprises at least one solvent selected from the group consisting of 2-octanone, 2-nonanone, 2-heptanone, 3-heptanone, 4-heptanone, 2-hexanone, 3-hexanone, diisobutyl ketone, methyl-cyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the step of exposing the resist film to high-energy radiation includes ArF immersion lithography of 193 nm wavelength or EUV lithography of 13.5 nm wavelength.

Typically, the ArF immersion lithography of 193 nm wavelength uses a halftone phase shift mask bearing a dot shifter pattern, whereby a pattern of holes is formed at the dots after development.

In a preferred embodiment, the exposure step uses a halftone phase shift mask bearing a lattice-like shifter pattern, whereby a pattern of holes is formed at the intersections between gratings of the lattice-like shifter pattern after development.

In a preferred embodiment, the exposure step uses halftone phase shift masks and includes two exposures of two intersecting sets of lines, whereby a pattern of holes is formed at the intersections between lines after development.

Most often, the halftone phase shift mask bearing a dot shifter pattern or lattice-like shifter pattern has a transmittance of 3 to 15%.

In a preferred embodiment, the phase shift mask used is a phase shift mask including a lattice-like first shifter having a line width equal to or less than a half pitch and a second shifter arrayed on the first shifter and consisting of lines whose on-wafer size is 2 to 30 nm thicker than the line width of the first shifter, whereby a pattern of holes is formed only where the thick shifter is arrayed.

In another preferred embodiment, the phase shift mask used is a phase shift mask including a lattice-like first shifter having a line width equal to or less than a half pitch and a second shifter arrayed on the first shifter and consisting of dots whose on-wafer size is 2 to 100 nm thicker than the line width of the first shifter, whereby a pattern of holes is formed only where the thick shifter is arrayed.

Another embodiment of the pattern forming process comprises the steps of applying a resist composition comprising a base resin comprising the polymer defined above, an acid generator, and an organic solvent onto a substrate, heat treating the composition to form a resist film, forming a protective film on the resist film, exposing the resist film to high-energy radiation to define exposed and unexposed regions, heat treating, and applying a developer to the coated substrate to form a negative pattern wherein the unexposed region of resist film and the protective film are dissolved and the exposed region of resist film is not dissolved.

The protective film is preferably formed of a composition comprising a polymer bearing a 1,1,1,3,3,3-hexafluoro-2-propanol residue and an amino group or amine salt-containing compound, or a composition comprising a polymer bearing a 1,1,1,3,3,3-hexafluoro-2-propanol residue and having amino group or amine salt-containing recurring units copolymerized, the composition further comprising an alcohol solvent of at least 4 carbon atoms, an ether solvent of 8 to 12 carbon atoms, or a mixture thereof.

ADVANTAGEOUS EFFECTS OF INVENTION

The resist composition, specifically chemically amplified positive resist composition, according to the invention displays a high resolution in the micropatterning technology, specifically ArF lithography, and is very useful in precise micropatterning.

In the process of image formation via positive/negative reversal by organic solvent development, a photoresist film comprising a polymer comprising recurring units derived from the acetal compound and an acid generator is characterized by a high dissolution contrast between the unexposed region of promoted dissolution and the exposed region of inhibited dissolution. By subjecting this photoresist film to exposure through a mask bearing a lattice-like pattern and organic solvent development, a fine hole pattern can be formed at a high sensitivity and a high precision of dimensional control.

BRIEF DESCRIPTION OF DRAWINGS

FIG. 1 schematically illustrates in cross-sectional views the pattern forming process of the invention.

DESCRIPTION OF EMBODIMENTS

Figure 1A:
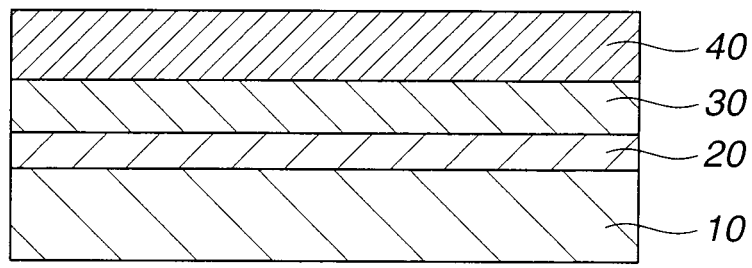
FIG. 1A shows a photoresist film formed on a substrate.

In the disclosure, the singular forms "a," "an" and "the" include plural referents unless the context clearly dictates otherwise. The notation (Cn-Cm) means a group containing from n to m carbon atoms per group.

The abbreviations and acronyms have the following meaning.

Mw: weight average molecular weight
Mn: number average molecular weight
Mw/Mn: molecular weight distribution or dispersity
GPC: gel permeation chromatography
PEB: post-exposure baking
PGMEA: propylene glycol monomethyl ether acetate The abbreviation "phr" refers to parts by weight per 100 parts by weight of resin or polymer.

It is understood that for some structures represented by chemical formulae, there can exist enantiomers and diastereomers because of the presence of asymmetric carbon atoms. In such a case, a single formula collectively represents all such isomers. The isomers may be used alone or in admixture.

Acetal Compound

In the first embodiment, the invention provides an acetal compound having the general formula (1).

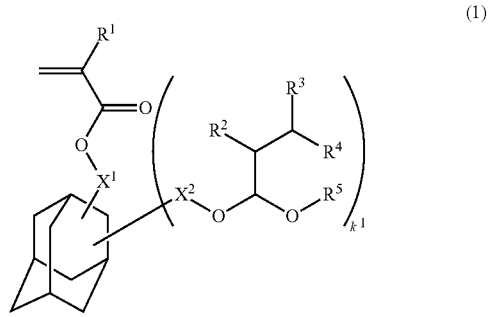

(1)

Herein $R^1$ is hydrogen, methyl or trifluoromethyl; $R^2$ is a straight, branched or cyclic monovalent $C_1$-$C_{10}$ hydrocarbon group; $R^3$ and $R^4$ are each independently hydrogen or a straight, branched or cyclic monovalent $C_1$-$C_{10}$ hydrocarbon group; $R^2$ and $R^3$ may bond together to form an aliphatic hydrocarbon ring with the carbon atoms to which they are attached; $X^1$ and $X^2$ are each independently a single bond or a straight or branched divalent $C_1$-$C_4$ hydrocarbon group; $R^5$ is a straight, branched or cyclic monovalent $C_1$-$C_{15}$ hydrocarbon group; and $k^1$ is an integer of 1 to 3.

Suitable straight, branched or cyclic monovalent $C_1$-$C_{10}$ hydrocarbon groups represented by $R^2$ to $R^4$ include alkyl groups such as methyl, ethyl, n-propyl, isopropyl, n-butyl, sec-butyl, isobutyl, tert-butyl, cyclopentyl, cyclohexyl, 2-ethylhexyl, and n-octyl.

Where $R^2$ and $R^3$ bond together to form an aliphatic hydrocarbon ring with the carbon atoms to which they are attached, suitable aliphatic hydrocarbon rings are those of 3 to 20 carbon atoms, preferably 4 to 15 carbon atoms, including cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, and adamantane.

Suitable straight, branched or cyclic monovalent $C_1$-$C_{15}$ hydrocarbon groups represented by $R^5$ include alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl.

Suitable straight or branched divalent $C_1$-$C_4$ hydrocarbon groups represented by $X^1$ and $X^2$ include alkylene groups such as methylene, ethylene, propane-1,1-diyl, propane-1,2-diyl, propane-1,3-diyl, butane-1,1-diyl, butane-1,2-diyl, butane-1,3-diyl, and butane-1,4-diyl.

The subscript $k^1$ is an integer of 1 to 3, with $k^1=2$ being preferred. In the case of $k^1=1$, the acetal compound must be introduced in a higher proportion in the synthesis of a polymer for accomplishing a high contrast. In the case of $k^1=3$, the acetal compound itself may have a higher molecular weight and sometimes become difficult to purify by distillation.

Illustrative non-limiting examples of the compound having formula (1) are given below wherein $R^1$ is as defined above and Me stands for methyl.

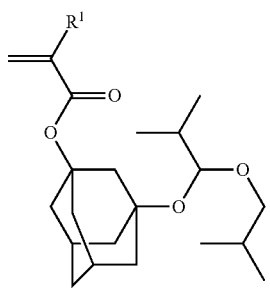

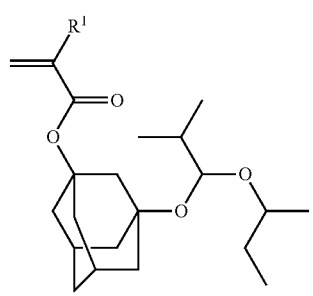

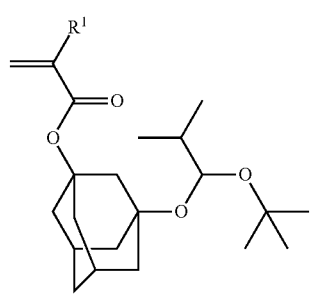

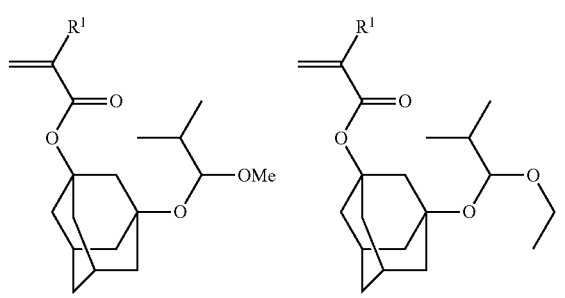

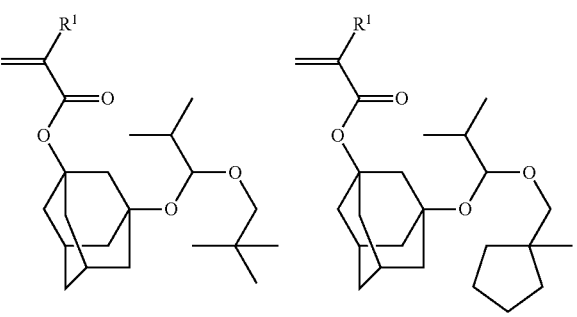

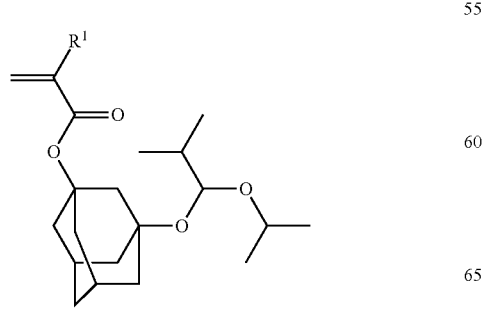

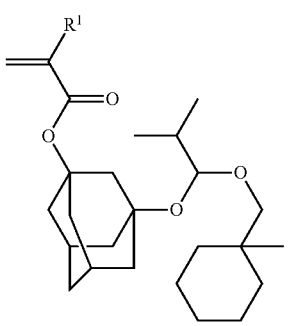

-continued
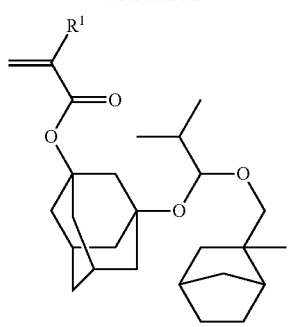
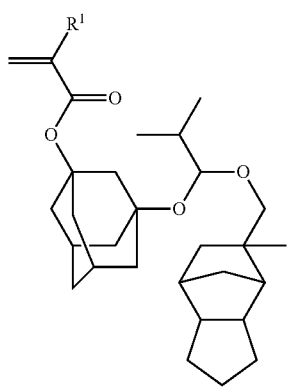
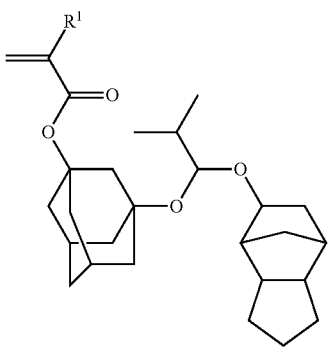
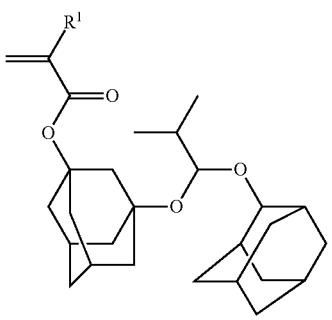
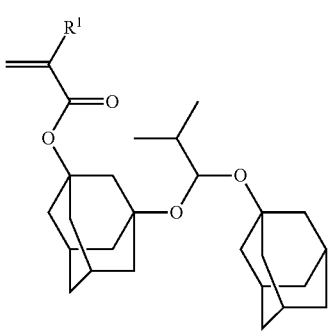
-continued
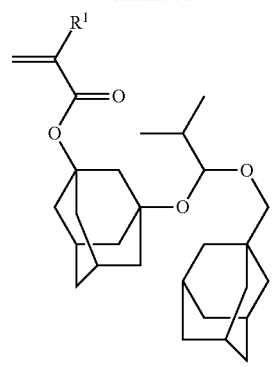
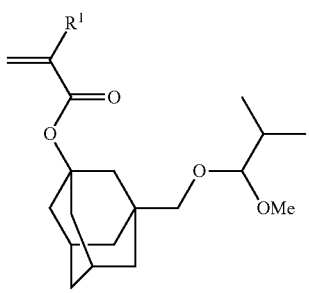
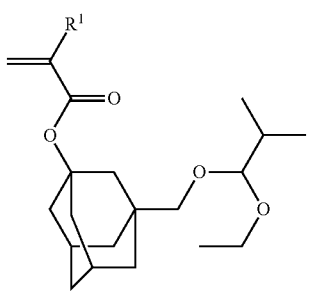
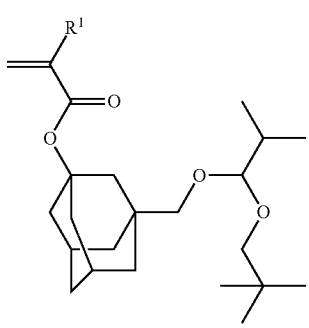
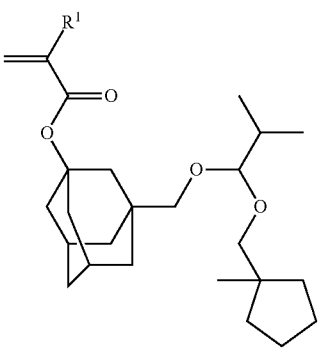

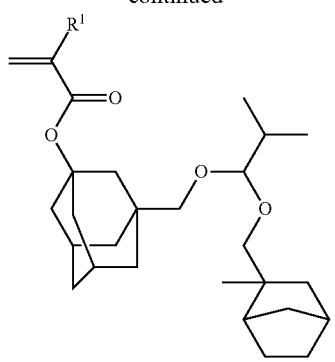
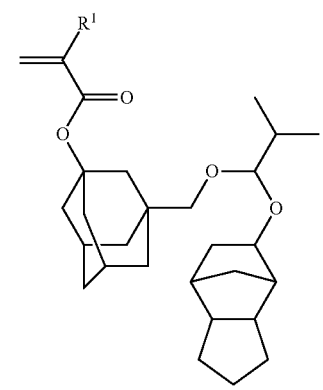
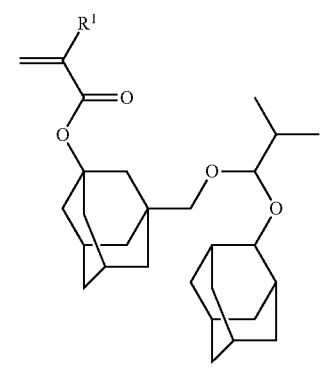
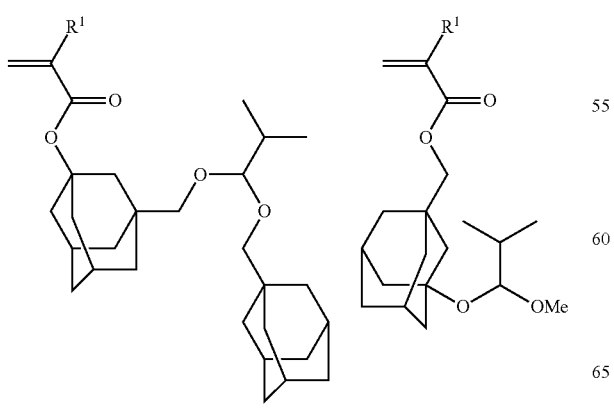
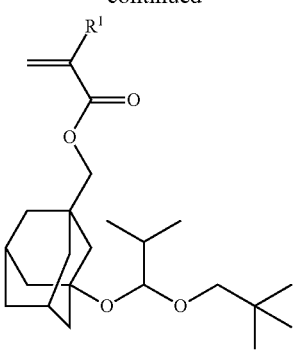
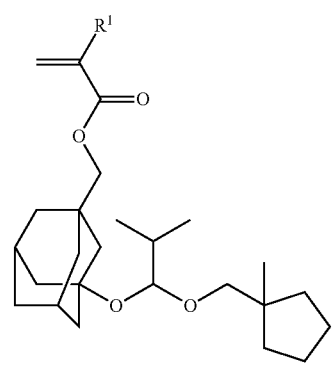
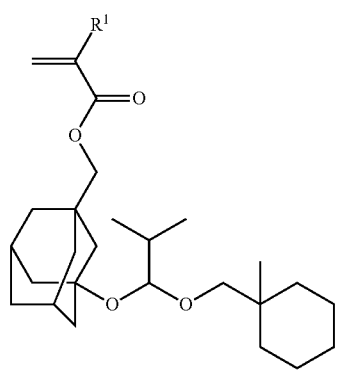
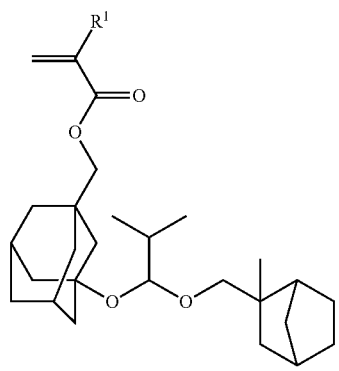

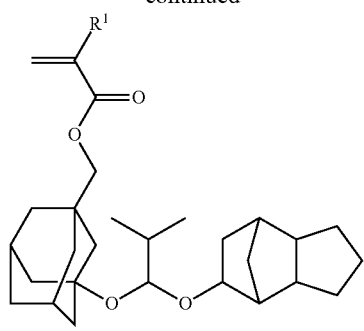
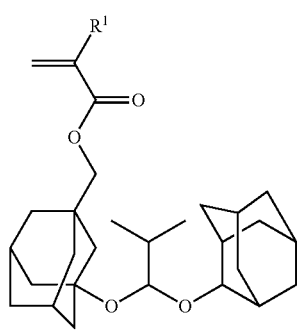
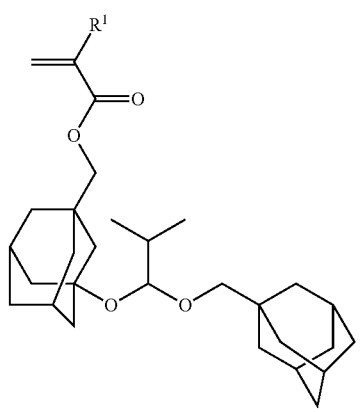
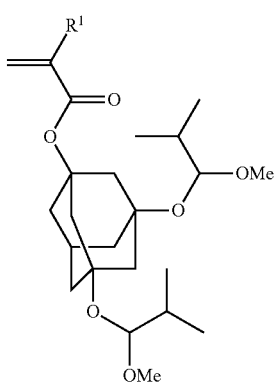
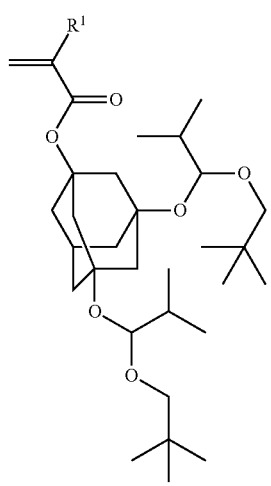
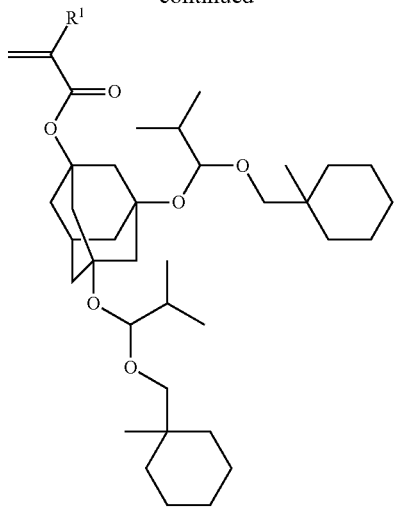
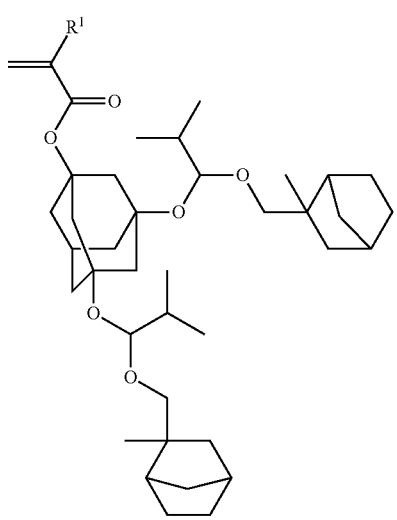
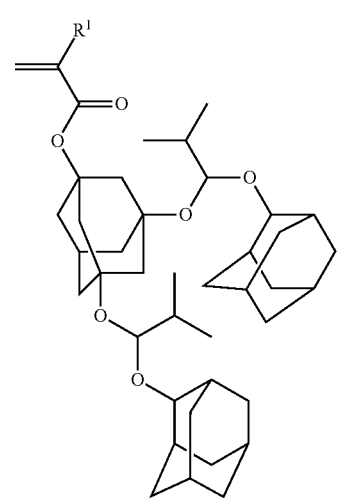

17
-continued
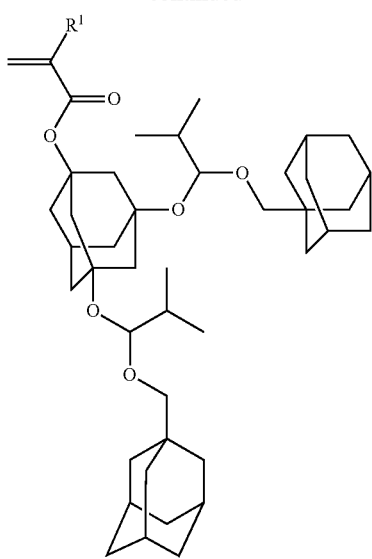
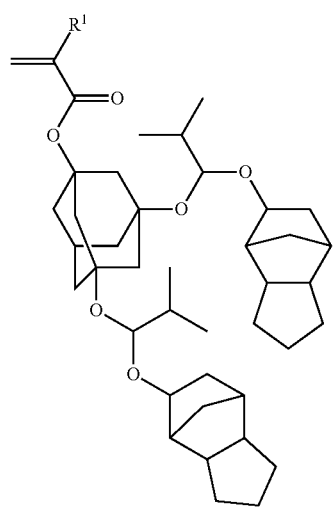
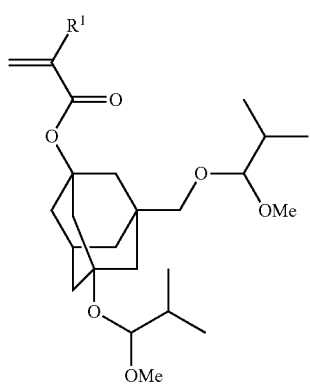
18
-continued
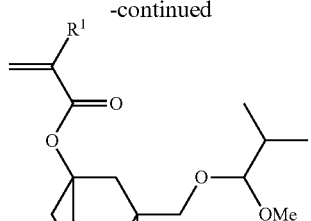
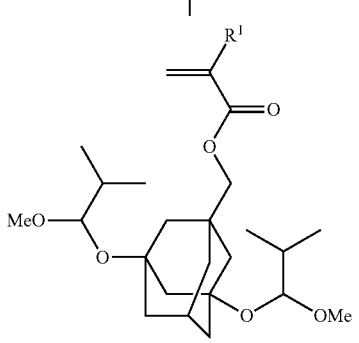
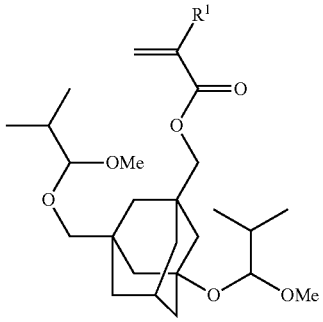
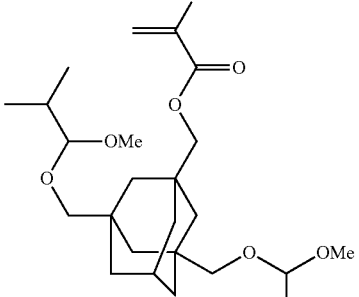
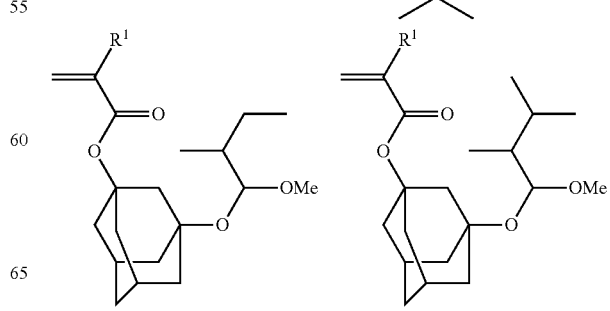

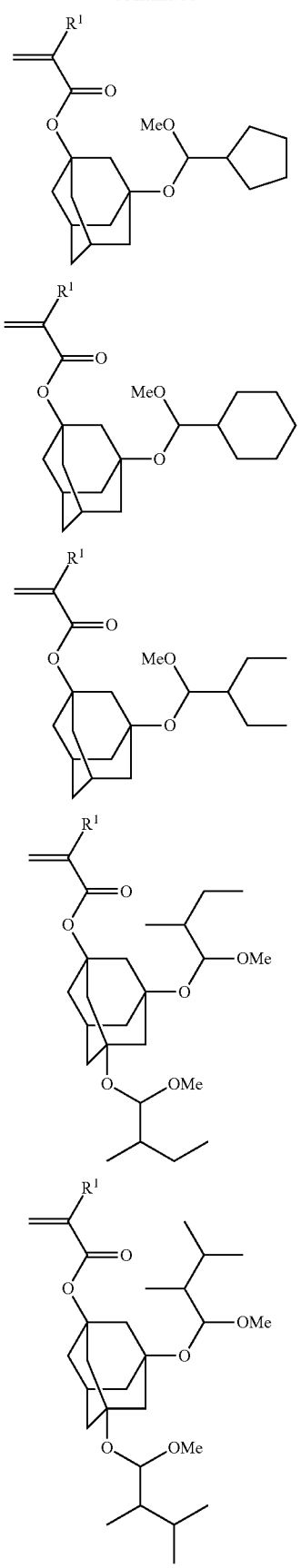
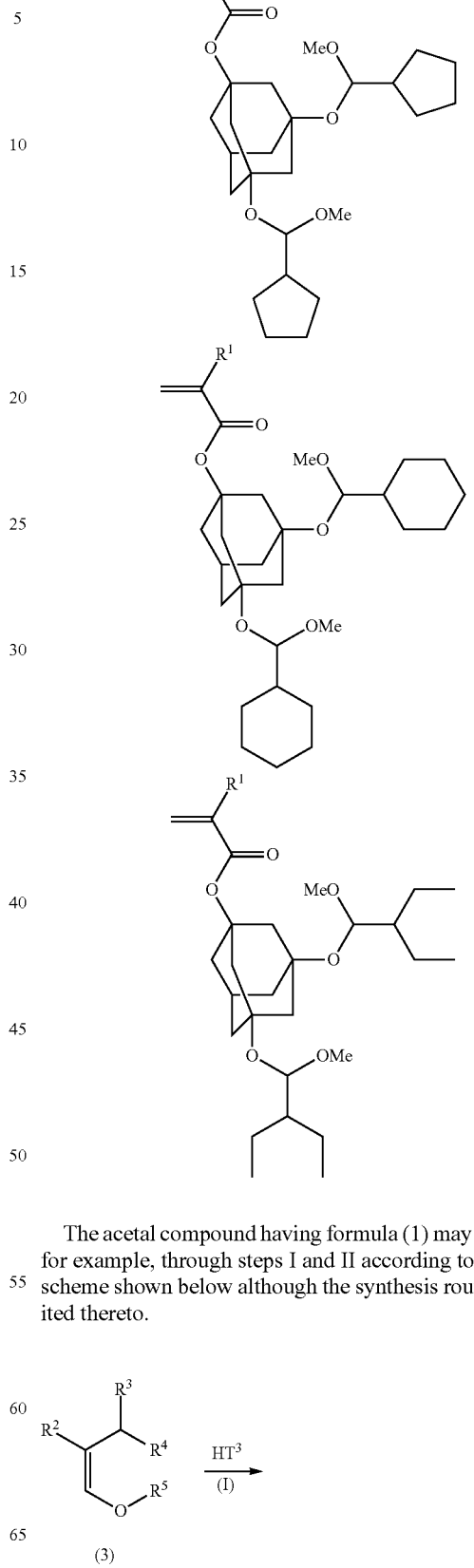
The acetal compound having formula (1) may be prepared, for example, through steps I and II according to the reaction scheme shown below although the synthesis route is not limited thereto.
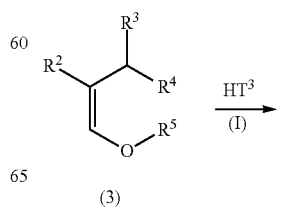

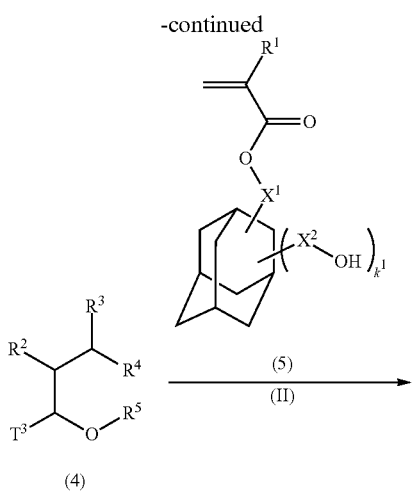

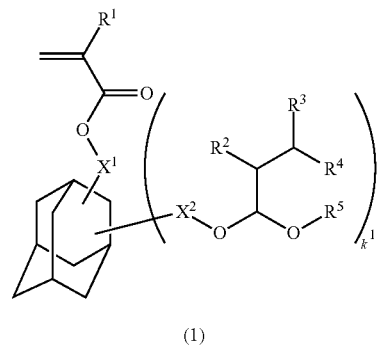

Herein $R^1$ to $R^5$, $X^1$, $X^2$, and $k^1$ are as defined above, and $T^3$ is halogen.

Step I is to add hydrogen halide to a vinyl ether compound (3) to form a haloalkyl ether compound (4). Typical of halogen $T^3$ are chlorine, bromine and iodine. Of these, chlorine is most preferred for ease of handling. The reaction may be conducted in a solventless system or in a solvent. Depending on reaction conditions, a suitable solvent may be selected from among ethers such as tetrahydrofuran, diethyl ether, di-n-butyl ether, and 1,4-dioxane, hydrocarbons such as n-hexane, n-heptane, benzene, toluene, xylene, and cumene, aprotic polar solvents such as dimethyl sulfoxide (DMSO) and N,N-dimethylformamide (DMF), and chlorinated organic solvents such as methylene chloride, chloroform, and carbon tetrachloride, alone or in admixture.

Reaction conditions including temperature and time may widely vary. In an example where $T^3$ is chlorine, the reaction temperature is desirably set in a range of −30° C. to 80° C., more desirably −10° C. to 40° C. for rapid reaction to completion. The reaction time is determined as appropriate by monitoring the reaction process by gas chromatography (GC) or silica gel thin-layer chromatography (TLC) because it is desirable from the yield aspect to drive the reaction to completion. Usually the reaction time is about 0.1 to about 10 hours. If necessary, the compound may be purified from the reaction mixture by standard techniques like distillation, chromatography and recrystallization. Most often, the crude product has a sufficient purity as the reactant to the subsequent step and may be used in the subsequent step without purification.

Step II is a protection reaction of haloalkyl ether compound (4) with a starting alcohol compound (5) to form an acetal compound (I). The reaction may be conducted in a standard way, for example, in a solventless system or in a solvent, by adding alcohol compound (5), haloalkyl ether compound (4), and a base such as triethylamine, pyridine or 4-dimethylaminopyridine in sequence or at the same time, and optional cooling or heating.

The amount of haloalkyl ether compound (4) used is preferably 0.5 to 10 moles, more preferably 1.0 to 2.0 moles per mole of alcohol compound (5), when the starting alcohol compound (5) has $k^1$=1. If the amount of compound (4) is less than 0.5 mole, a large fraction of the starting compound is left unreacted, leading to a substantial drop of yield. More than 10 moles of compound (4) may be disadvantageous from the cost aspect because of an increased reactant expense and a reduced pot yield.

Examples of the solvent used herein include hydrocarbons such as toluene, xylene, hexane, and heptane, chlorinated solvents such as methylene chloride, chloroform, and dichloroethane, ethers such as diethyl ether, tetrahydrofuran, and dibutyl ether, ketones such as acetone and 2-butanone, esters such as ethyl acetate and butyl acetate, nitriles such as acetonitrile, alcohols such as methanol and ethanol, aprotic polar solvents such as N,N-dimethylformamide, N,N-dimethylacetamide and dimethyl sulfoxide, and water, alone or in admixture. A phase transfer catalyst such as tetrabutylammonium hydrogen sulfate may be added to the reaction system. The amount of phase transfer catalyst used may be preferably 0.0001 to 1.0 mole, and more preferably 0.001 to 0.5 mole per mole of alcohol compound (5) wherein $k^1$ is 1. Less than 0.0001 mole of the catalyst may fail to achieve the desired addition effect whereas more than 1.0 mole may be uneconomical due to an increased material expense.

It is desired for higher yields that the reaction time be determined by monitoring the progress of reaction by thin-layer chromatography (TLC) or gas chromatography (GC). The reaction time is usually about 30 minutes to about 40 hours. The acetal compound (1) may be recovered from the reaction mixture by ordinary aqueous work-up. If necessary, it can be purified by any standard technique such as distillation, recrystallization or chromatography.

An alternative exemplary method for the synthesis of acetal compound (1) is an addition reaction between a vinyl ether compound (3) and an alcohol compound (5) in the presence of an acid catalyst. The reaction may readily proceed in a standard way. For example, the reaction between vinyl ether compound (3) and alcohol compound (5) is conducted in a solventless system or in a solvent such as toluene or hexane in the presence of an acid catalyst at a reaction temperature of 0 to 50° C., while optionally removing water of reaction out of the system. Suitable acid catalysts used herein include mineral acids such as hydrochloric acid, sulfuric acid, nitric acid, and perchloric acid, and organic acids such as p-toluenesulfonic acid, benzenesulfonic acid, methanesulfonic acid, and trifluoroacetic acid.

Typical of the substituent group in the form of an alcoholic hydroxyl group protected with acetal as in the invention are ethoxyethyl (EOE) and tetrahydropyranyl (THP) groups. However, these groups are not practical because they are extremely reactive with acid, raising a problem with respect to the storage stability of resist material.

It is noted that JP-A 2008-203639 discloses conceptually a broad range of structure encompassing an acetal compound having formula (1) disclosed herein. Synthesis process is nowhere disclosed. It was uncertain for those skilled in the art at that time how to synthesize a compound having an acetal group whose carbonyl moiety is of branched structure as disclosed herein.

It is thus believed that the present invention first discloses, in a substantial sense, acetal compounds in which an alcoholic hydroxyl group having an adamantane ring is protected with an acetal group whose carbonyl moiety is of branched structure. Also the synthesis of such acetal compounds is first disclosed herein.

Polymer

In the second embodiment, the invention provides a polymer or high-molecular-weight compound comprising recurring units derived from the acetal compound of formula (1).

Specifically, the recurring units derived from the acetal compound of formula (1) include units having the general formula (2).

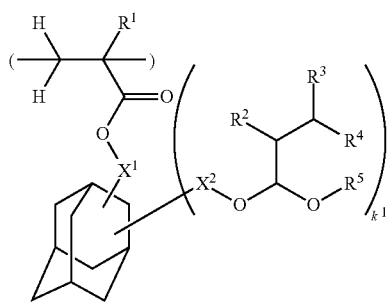

(2)

Herein $R^1$ to $R^5$, $X^1$, $X^2$, and $k^1$ are as defined above.

In addition to the recurring units derived from the acetal compounds having formula (1), the polymer of the invention may further comprise recurring units (b) having an acid labile group-substituted carboxyl group as represented by the following formula.

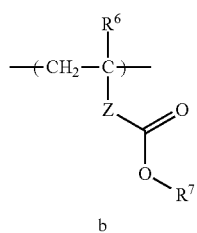

b

Suitable monomers Mb from which recurring units (b) are derived have the following formula.

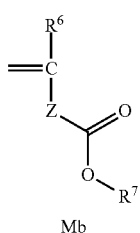

Mb

Herein $R^6$ is hydrogen or methyl, $R^7$ is an acid labile group, and Z is a single bond or —C(=O)—O—$R^8$— wherein $R^8$ is a straight, branched or cyclic $C_1$-$C_{10}$ alkylene group which may contain an ether, ester, lactone or hydroxyl radical, or a naphthylene group.

Examples of the monomers Mb having different Z structures are given below wherein $R^6$ and $R^7$ are as defined above.

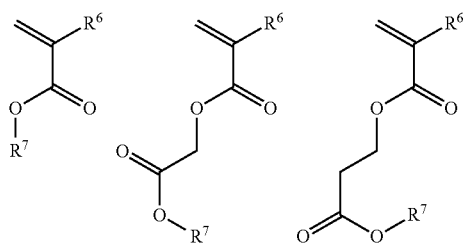

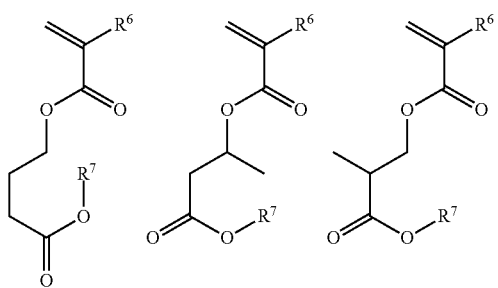

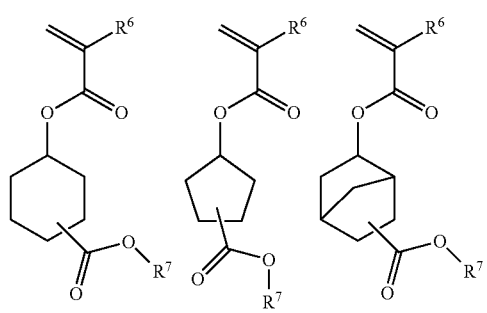

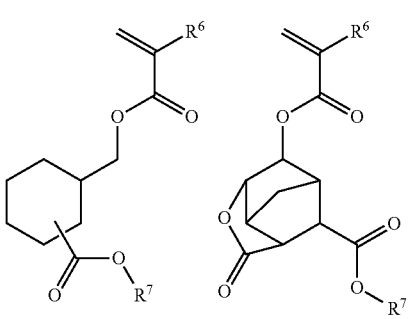

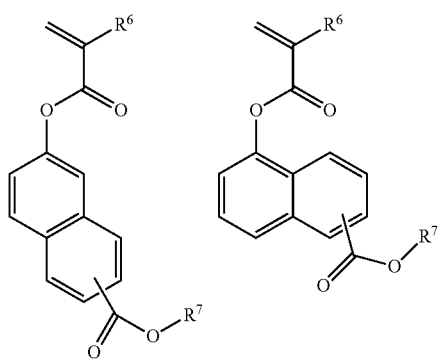

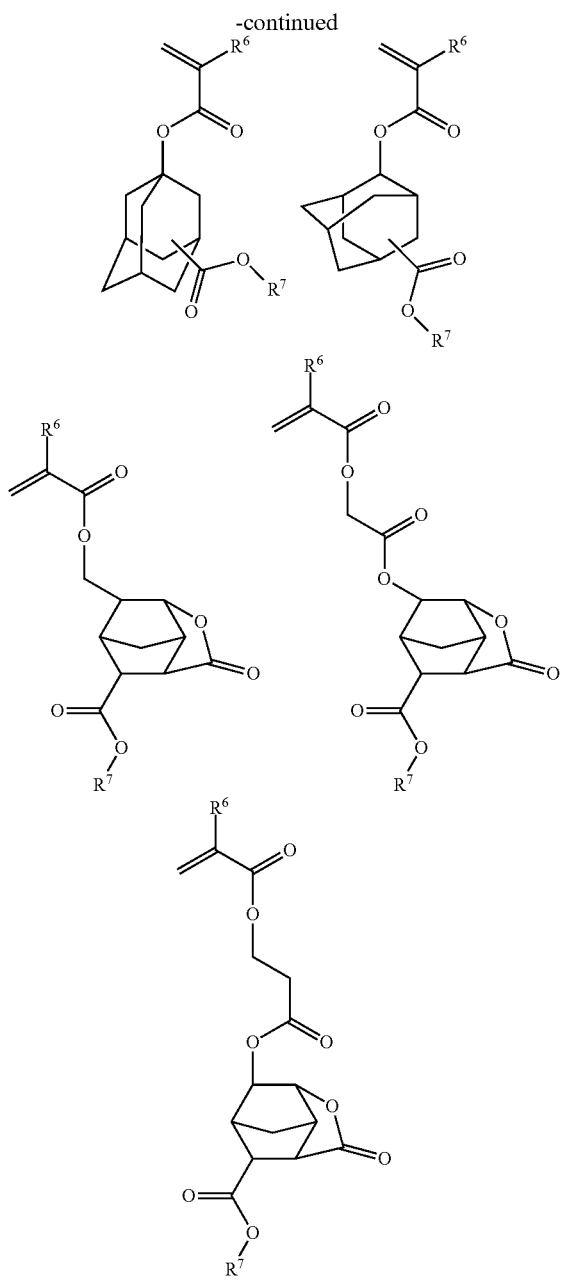

The acid labile group represented by R⁷ may be selected from a variety of such groups. Suitable acid labile groups include groups of the following formulae (AL-10) and (AL-11), tertiary alkyl groups of the following formula (AL-12), and oxoalkyl groups of 4 to 20 carbon atoms, but are not limited thereto.

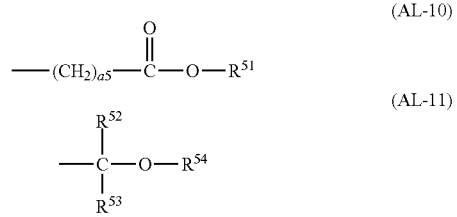

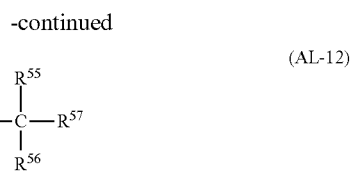

In formulae (AL-10) and (AL-11), $R^{51}$ and $R^{54}$ each are a monovalent hydrocarbon group, typically straight, branched or cyclic alkyl group, of 1 to 40 carbon atoms, more specifically 1 to 20 carbon atoms, which may contain a heteroatom such as oxygen, sulfur, nitrogen or fluorine. $R^{52}$ and $R^{53}$ each are hydrogen or a monovalent hydrocarbon group, typically straight, branched or cyclic alkyl group, of 1 to 20 carbon atoms which may contain a heteroatom such as oxygen, sulfur, nitrogen or fluorine. The subscript "a5" is an integer of 0 to 10, and especially 1 to 5. Alternatively, a pair of $R^{52}$ and $R^{53}$, $R^{52}$ and $R^{54}$, or $R^{53}$ and $R^{54}$ may bond together to form a ring, specifically aliphatic ring, with the carbon atom or the carbon and oxygen atoms to which they are attached, the ring having 3 to 20 carbon atoms, especially 4 to 16 carbon atoms.

In formula (AL-12), $R^{55}$, $R^{56}$ and $R^{57}$ each are a monovalent hydrocarbon group, typically straight, branched or cyclic alkyl group, of 1 to 20 carbon atoms which may contain a heteroatom such as oxygen, sulfur, nitrogen or fluorine. Alternatively, a pair of $R^{55}$ and $R^{56}$, $R^{55}$ and $R^{57}$, or $R^{56}$ and $R^{57}$ may bond together to form a ring, specifically aliphatic ring, with the carbon atom to which they are attached, the ring having 3 to 20 carbon atoms, especially 4 to 16 carbon atoms.

Illustrative examples of the groups of formula (AL-10) include tert-butoxycarbonyl, tert-butoxycarbonylmethyl, tert-amyloxycarbonyl, tert-amyloxycarbonylmethyl, 1-ethoxyethoxycarbonylmethyl, 2-tetrahydropyranyloxycarbonylmethyl and 2-tetrahydrofuranyloxycarbonylmethyl as well as substituent groups of the following formulae (AL-10)-1 to (AL-10)-10.

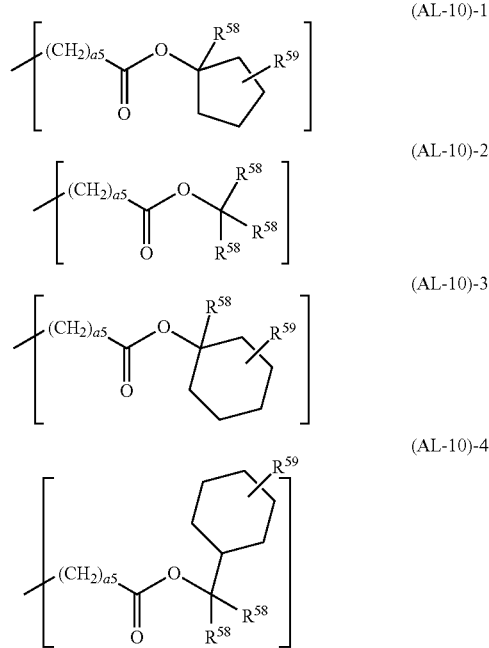

-continued

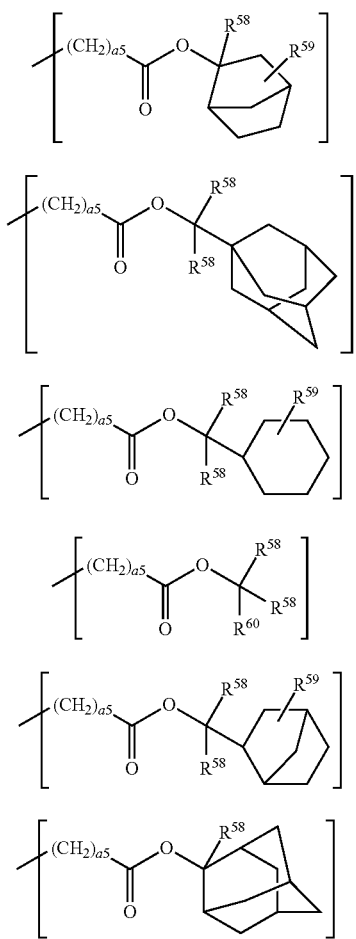

(AL-10)-5
(AL-10)-6
(AL-10)-7
(AL-10)-8
(AL-10)-9
(AL-10)-10

In formulae (AL-10)-1 to (AL-10)-10, $R^{58}$ is each independently a straight, branched or cyclic $C_1$-$C_8$ alkyl group, $C_6$-$C_{20}$ aryl group or $C_7$-$C_{20}$ aralkyl group; $R^{59}$ is hydrogen or a straight, branched or cyclic $C_1$-$C_{20}$ alkyl group; $R^H$ is a $C_6$-$C_{20}$ aryl group or $C_7$-$C_{20}$ aralkyl group; and "a5" is as defined above.

Illustrative examples of the acetal group of formula (AL-11) include those of the following formulae (AL-11)-1 to (AL-11)-34.

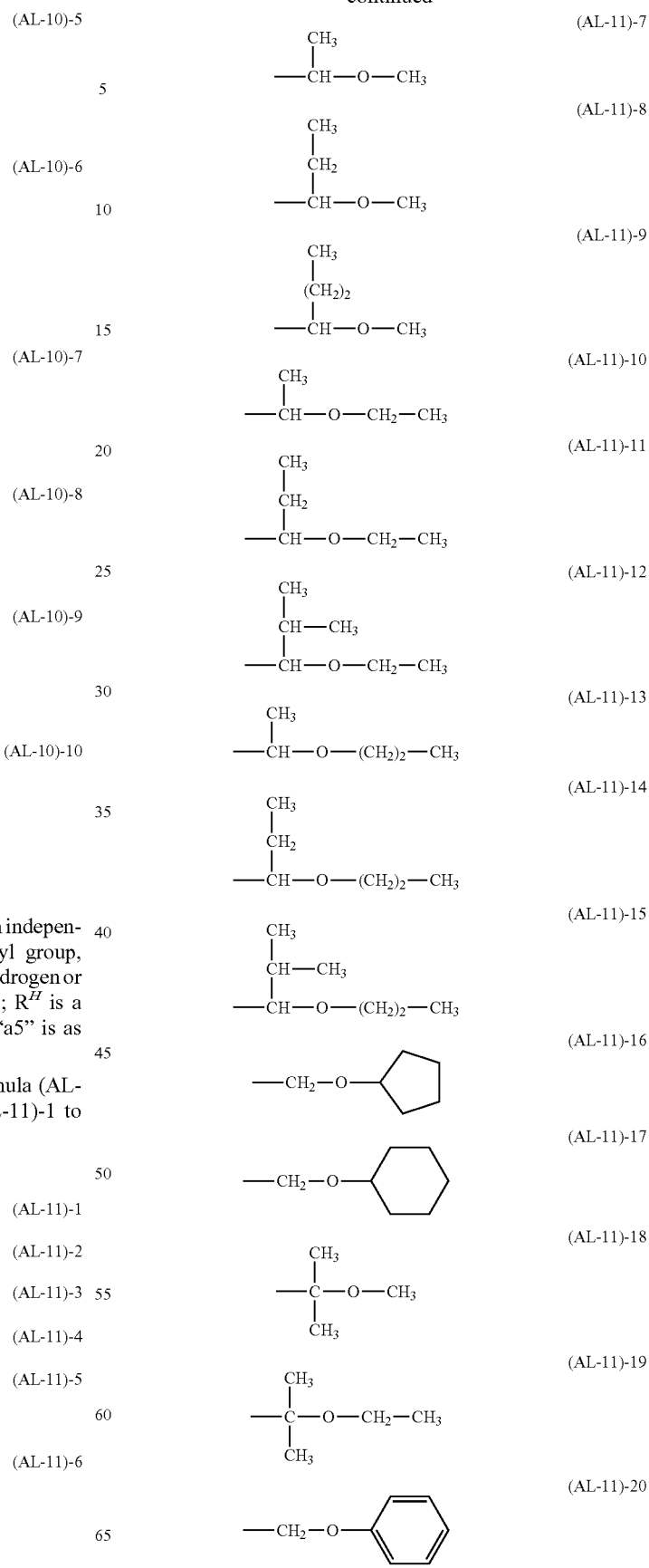

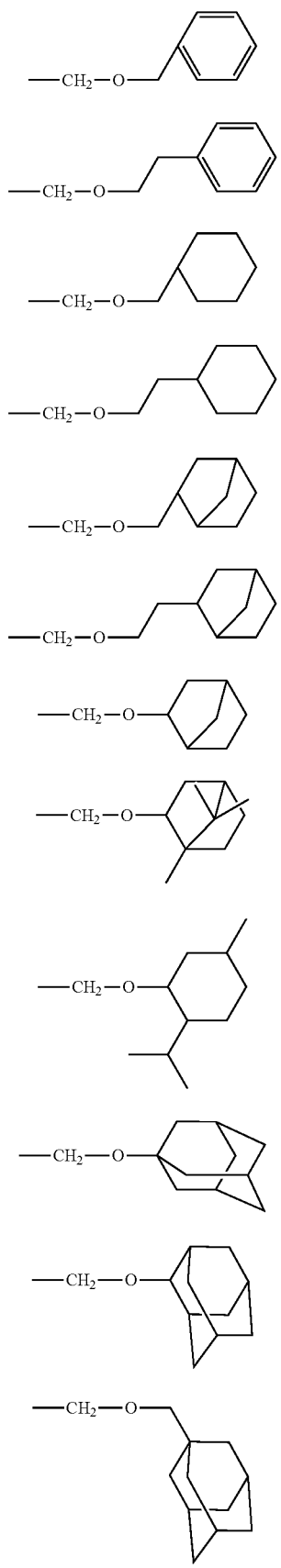
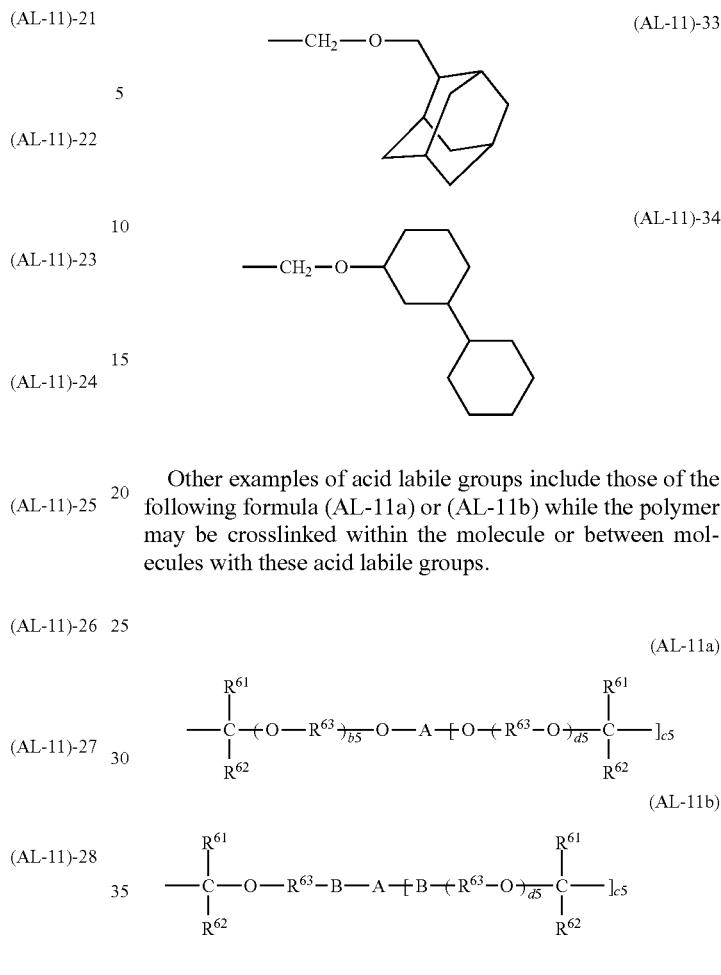

Other examples of acid labile groups include those of the following formula (AL-11a) or (AL-11b) while the polymer may be crosslinked within the molecule or between molecules with these acid labile groups.

$$\mathrm{-\underset{R^{62}}{\overset{R^{61}}{C}}-\!\!\!\!+\!\!\!O\!-\!R^{63}\!\!\!\!\underset{b5}{\vphantom{O}}\!\!-\!O\!-\!A\!\!+\!\!O\!\!+\!R^{63}\!-\!O\!\!\underset{d5}{\vphantom{O}}\!\!-\!\underset{R^{62}}{\overset{R^{61}}{C}}\!-\!]_{c5}} \quad \text{(AL-11a)}$$

$$\mathrm{-\underset{R^{62}}{\overset{R^{61}}{C}}-O\!-\!R^{63}\!-\!B\!-\!A\!\!+\!\!B\!\!+\!R^{63}\!-\!O\!\!\underset{d5}{\vphantom{O}}\!\!-\!\underset{R^{62}}{\overset{R^{61}}{C}}\!-\!]_{c5}} \quad \text{(AL-11b)}$$

Herein $R^{61}$ and $R^{62}$ each are hydrogen or a straight, branched or cyclic $C_1$-$C_8$ alkyl group, or $R^{61}$ and $R^{62}$ may bond together to form a ring with the carbon atom to which they are attached, and $R^{61}$ and $R^{62}$ are straight or branched $C_1$-$C_8$ alkylene groups when they form a ring. $R^{63}$ is a straight, branched or cyclic $C_1$-$C_{10}$ alkylene group. Each of b5 and d5 is 0 or an integer of 1 to 10, preferably 0 or an integer of 1 to 5, and c5 is an integer of 1 to 7. "A" is a (c5+1)-valent aliphatic or alicyclic saturated hydrocarbon group, aromatic hydrocarbon group or heterocyclic group having 1 to 50 carbon atoms, which may be separated by a heteroatom such as oxygen, sulfur or nitrogen or in which some of the hydrogen atoms attached to carbon atoms may be substituted by hydroxyl, carboxyl, carbonyl radicals or fluorine atoms. "B" is —CO—O—, —NHCO—O— or —NH-CONH—.

Preferably, "A" is selected from divalent to tetravalent, straight, branched or cyclic $C_1$-$C_{20}$ alkylene, alkanetriyl and alkanetetrayl groups, and $C_6$-$C_{30}$ arylene groups, which may be separated by a heteroatom such as oxygen, sulfur or nitrogen or in which some of the hydrogen atoms attached to carbon atoms may be substituted by hydroxyl, carboxyl, acyl radicals or halogen atoms. The subscript c5 is preferably an integer of 1 to 3.

The crosslinking acetal groups of formulae (AL-11a) and (AL-11b) are exemplified by the following formulae (AL-11)-35 through (AL-11)-42.

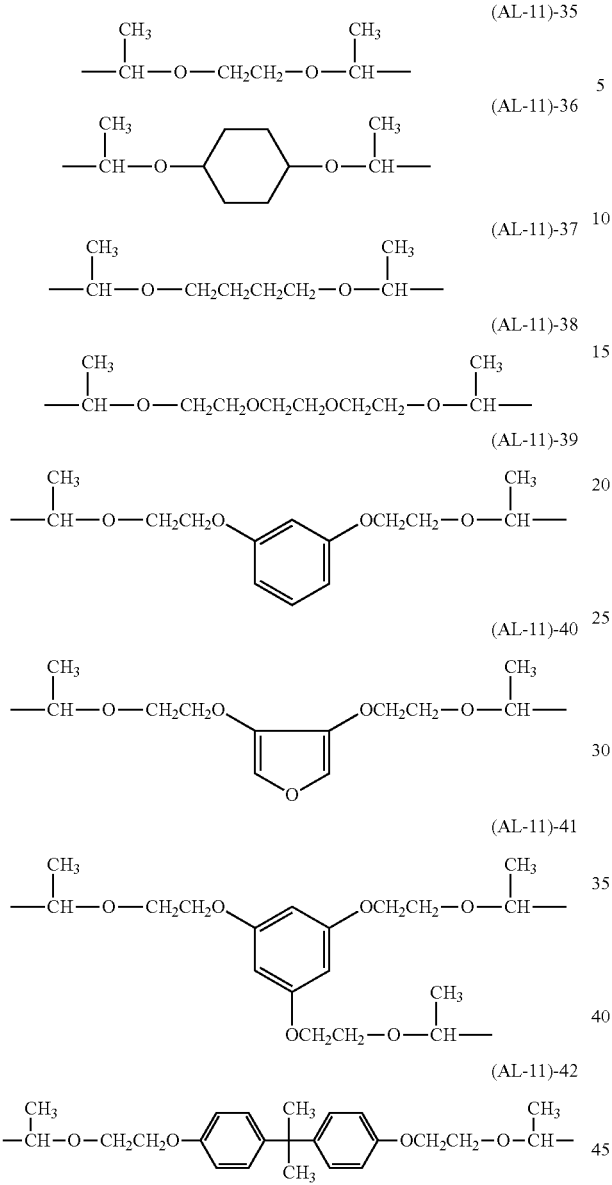
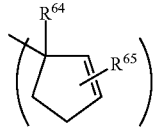
(AL-12)-3
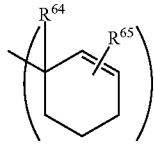
(AL-12)-4
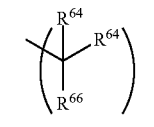
(AL-12)-5
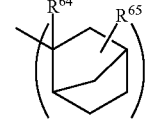
(AL-12)-6
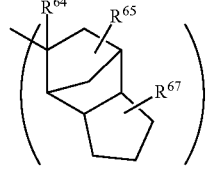
(AL-12)-7
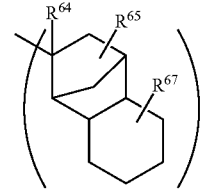
(AL-12)-8
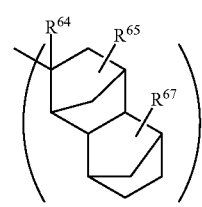
(AL-12)-9
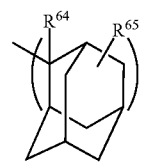
(AL-12)-10
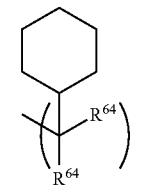
(AL-12)-11
Illustrative examples of the tertiary alkyl of formula (AL-12) include tert-butyl, triethylcarbyl, 1-ethylnorbornyl, 1-methylcyclohexyl, 1-ethylcyclopentyl, and tert-amyl groups as well as those of (AL-12)-1 to (AL-12)-16.
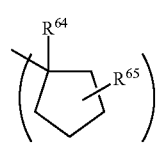
(AL-12)-1
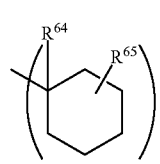
(AL-12)-2

(AL-12)-12

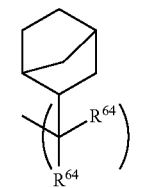

(AL-12)-13

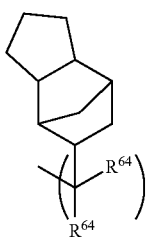

(AL-12)-14

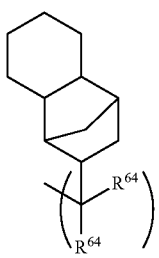

(AL-12)-15

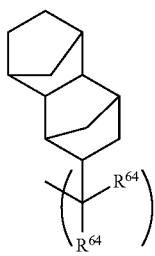

(AL-12)-16

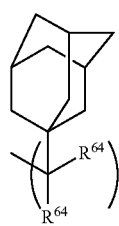

Herein $R^{64}$ is each independently a straight, branched or cyclic $C_1$-$C_8$ alkyl group, $C_6$-$C_{20}$ aryl group or $C_7$-$C_{20}$ aralkyl group, two $R^H$ may bond together to form a ring; $R^{65}$ and $R^{67}$ each are hydrogen or a straight, branched or cyclic $C_1$-$C_{20}$ alkyl group; and $R^{66}$ is a $C_6$-$C_{20}$ aryl group or $C_7$-$C_{20}$ aralkyl group.

With acid labile groups containing $R^{68}$ representative of a di- or poly-valent alkylene or arylene group as shown by formulae (AL-12)-17 and (AL-12)-18, the polymer may be crosslinked within the molecule or between molecules. In formulae (AL-12)-17 and (AL-12)-18, $R^{64}$ is as defined above, $R^{68}$ is a single bond, or a straight, branched or cyclic $C_1$-$C_{20}$ alkylene group or arylene group which may contain a heteroatom such as oxygen, sulfur or nitrogen, and b6 is an integer of 0 to 3.

(AL-12)-17

(AL-12)-18

The groups represented by $R^{64}$, $R^{65}$, $R^{66}$ and $R^{67}$ may contain a heteroatom such as oxygen, nitrogen or sulfur. Such groups are exemplified by those of the following formulae (AL-13)-1 to (AL-13)-7.

—(CH$_2$)$_4$OH      (AL-13)-1

—(CH$_2$)$_2$O(CH$_2$)$_3$CH$_3$      (AL-13)-2

(AL-13)-3

—(CH$_2$)$_2$O(CH$_2$)$_2$OH      (AL-13)-4

—(CH$_2$)$_6$OH      (AL-13)-5

(AL-13)-6

(AL-13)-7

As the acid labile group $R^7$, groups having an exo-form structure represented by the formula (AL-12)-19 are also preferred.

(AL-12)-19

Herein, $R^{69}$ is a straight, branched or cyclic $C_1$-$C_8$ alkyl group or an optionally substituted $C_6$-$C_{20}$ aryl group; $R^{70}$ to $R^{75}$, $R^{78}$ and $R^{79}$ are each independently hydrogen or a monovalent hydrocarbon group, typically alkyl, of 1 to 15 carbon atoms which may contain a heteroatom; and $R^{76}$ and $R^{77}$ are hydrogen or a monovalent hydrocarbon group of 1 to 15 carbon atoms which may contain a heteroatom. Alternatively, a pair of $R^{70}$ and $R^{71}$, $R^{72}$ and $R^{74}$, $R^{72}$ and $R^{75}$, $R^{73}$ and $R^{75}$, $R^{73}$ and $R^{79}$, $R^{74}$ and $R^{78}$, $R^{76}$ and $R^{77}$, or $R^{77}$ and $R^{78}$ may bond together to form a ring, specifically aliphatic ring, with the carbon atom(s) to which they are attached, and in this case, each ring-former R is a divalent hydrocarbon group, typically alkylene, of 1 to 15 carbon atoms which may contain a heteroatom. Also, a pair of $R^{70}$ and $R^{79}$, $R^{76}$ and $R^{79}$, or $R^{72}$ and $R^{74}$ which are attached to vicinal carbon atoms may bond together directly to form a double bond. The formula also represents an enantiomer.

The ester form monomers from which recurring units having an exo-form structure represented by the formula (AL-12)-19 are derived are described in U.S. Pat. No. 6,448,420 (JP-A 2000-327633), with such recurring units being illustrated below.

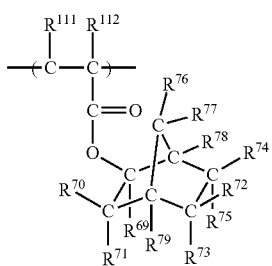

It is noted that $R^{111}$ and $R^{112}$ are each independently hydrogen, methyl, —$COOCH_3$, —$CH_2COOCH_3$ or the like. Illustrative non-limiting examples of suitable monomers are given below.

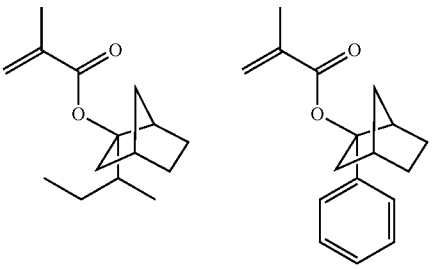

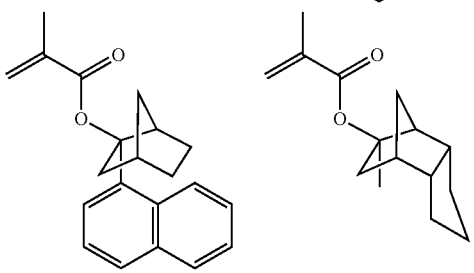

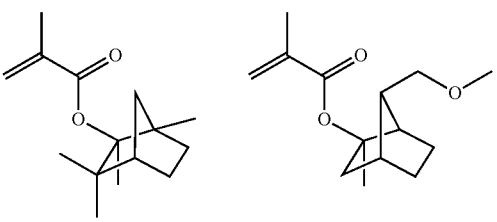

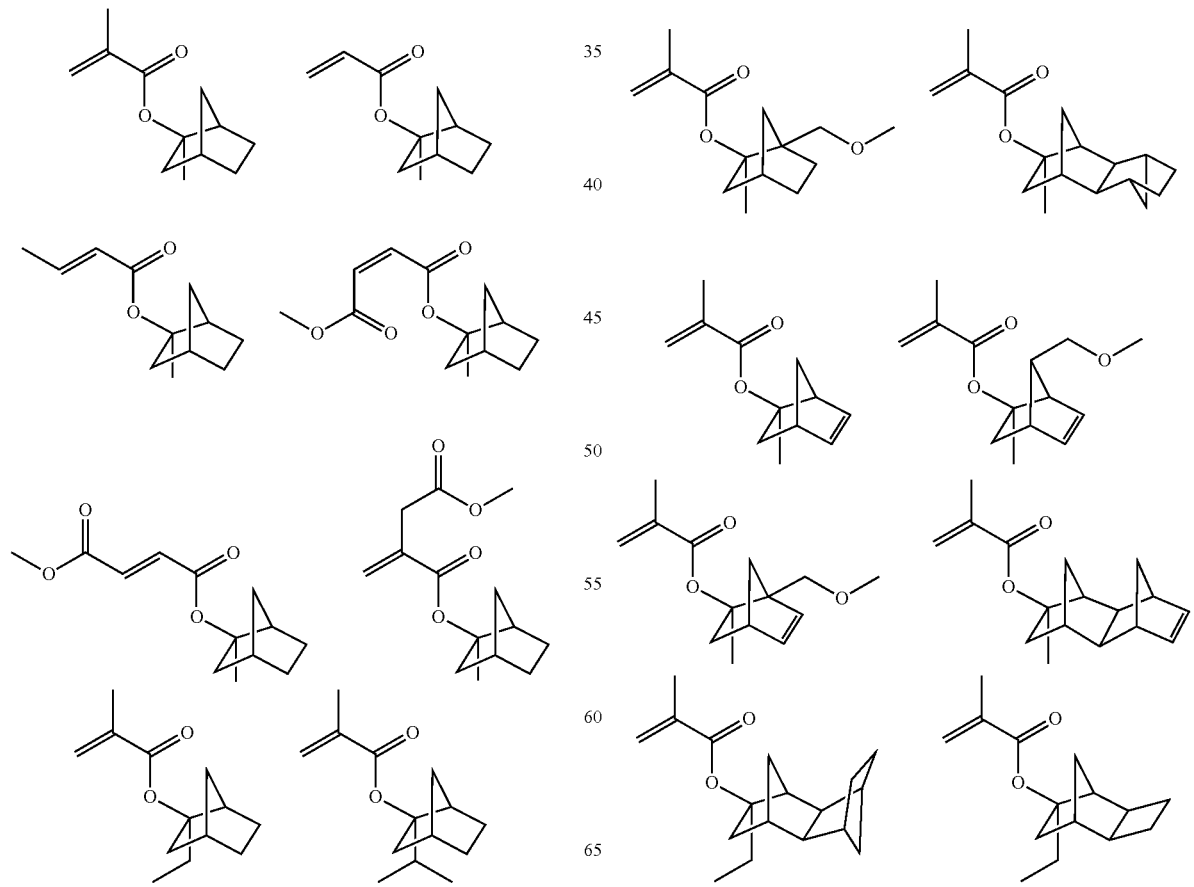

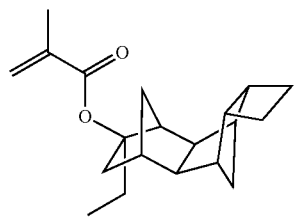

Also included in the acid labile groups of formula (AL-12) as $R^7$ are acid labile groups having furandiyl, tetrahydrofurandiyl or oxanorbornanediyl as represented by the following formula (AL-12)-20.

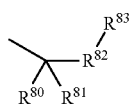

(AL-12)-20

Herein, $R^{80}$ and $R^{81}$ are each independently a monovalent hydrocarbon group, typically a straight, branched or cyclic $C_1$-$C_{10}$ alkyl. $R^{80}$ and $R^{81}$ may bond together to form an aliphatic hydrocarbon ring of 3 to 20 carbon atoms with the carbon atom to which they are attached. $R^{82}$ is a divalent group selected from furandiyl, tetrahydrofurandiyl and oxanorbornanediyl. $R^{83}$ is hydrogen or a monovalent hydrocarbon group, typically a straight, branched or cyclic $C_1$-$C_{10}$ alkyl, which may contain a heteroatom.

Examples of the monomers from which the recurring units substituted with acid labile groups having furandiyl, tetrahydrofurandiyl and oxanorbornanediyl as represented by the formula:

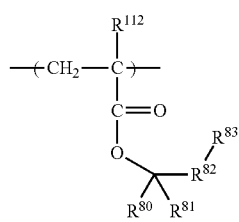

(wherein $R^{80}$ to $R^{83}$, and $R^{112}$ are as defined above) are derived are shown below. Note that Me is methyl and Ac is acetyl.

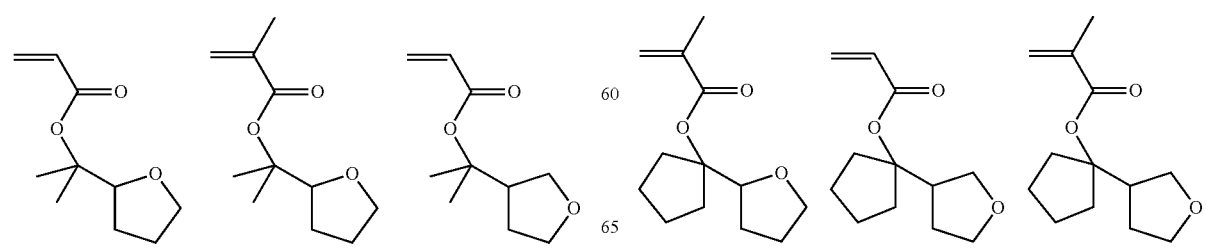

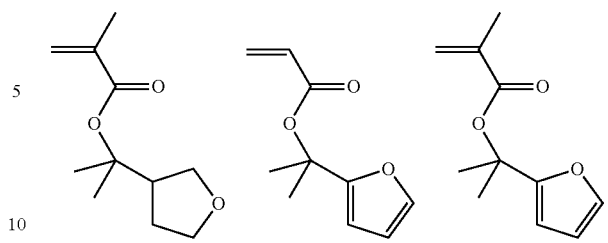

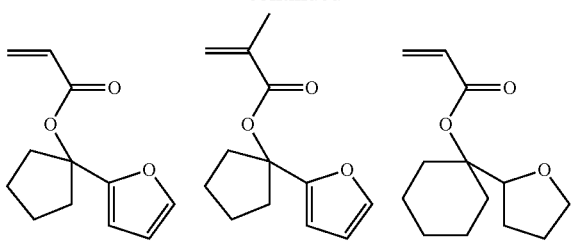
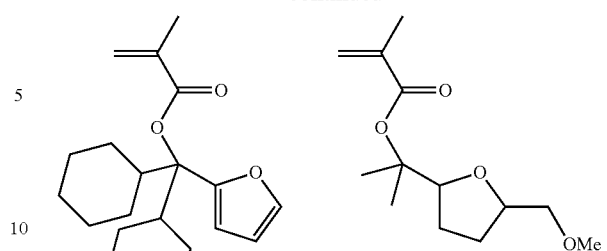
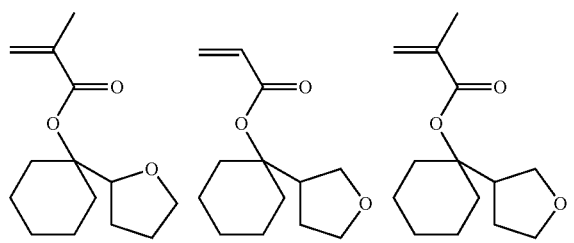
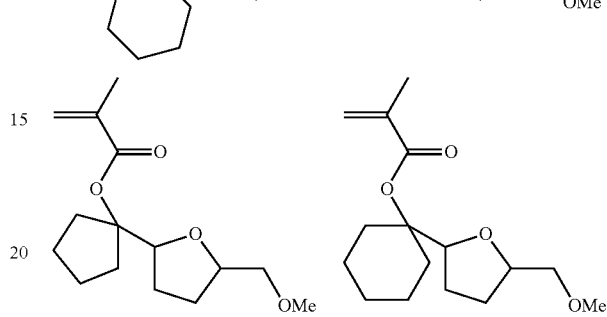
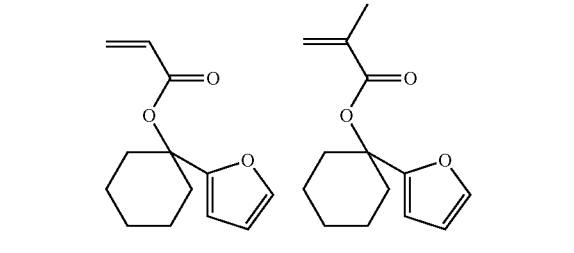
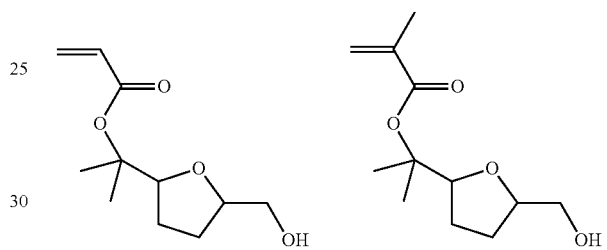
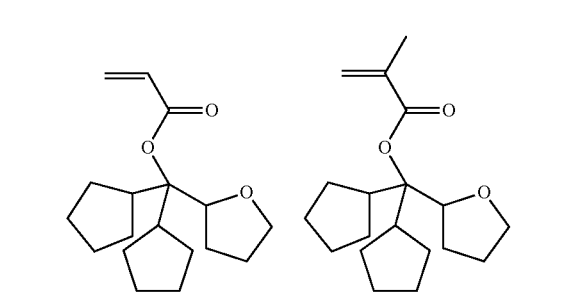
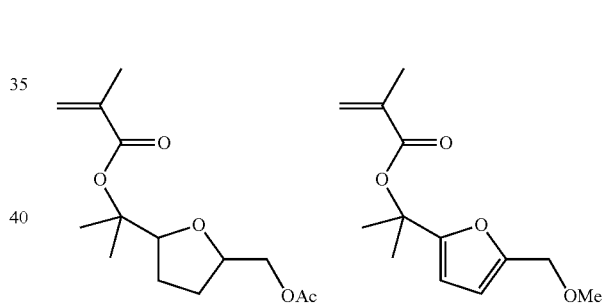
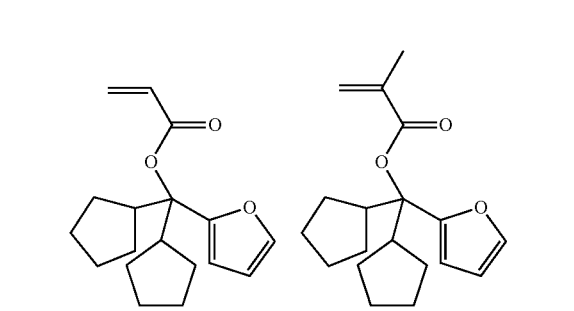
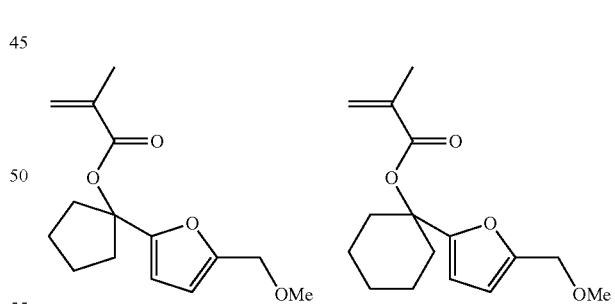
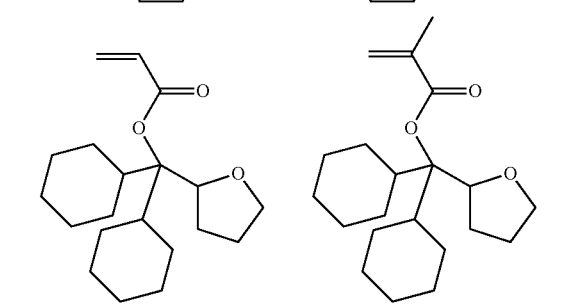
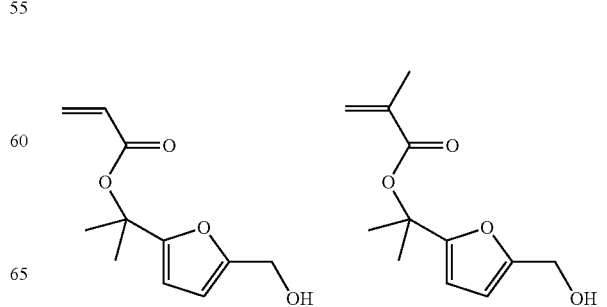

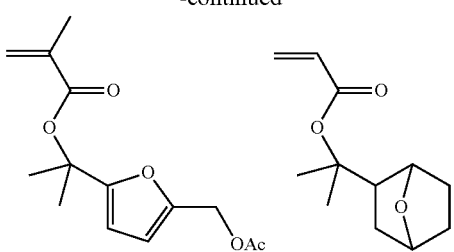
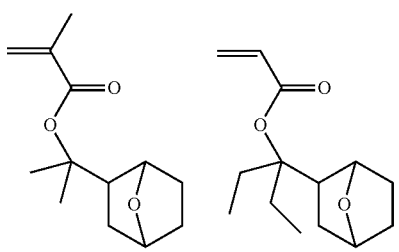
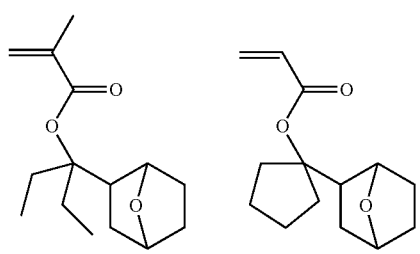
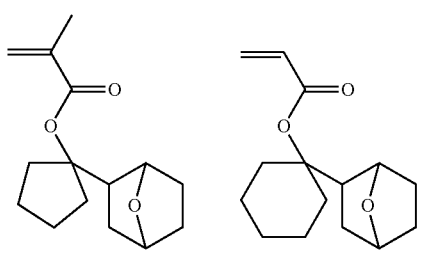
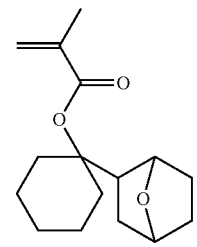

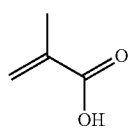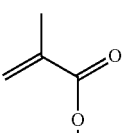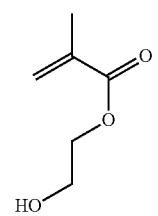
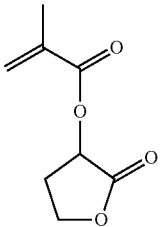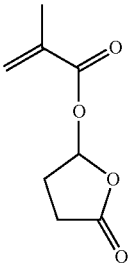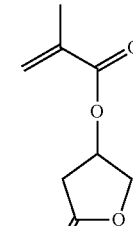
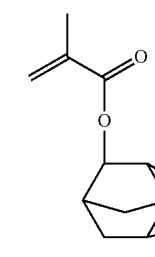
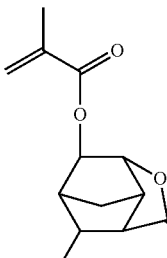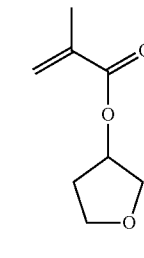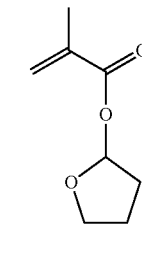
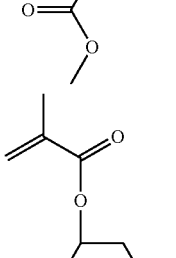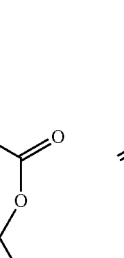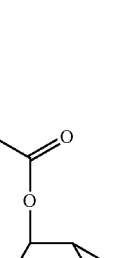
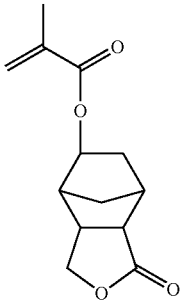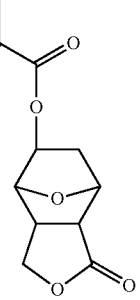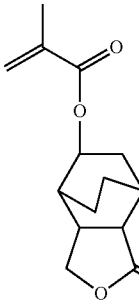

For convenience of description, the unit having formula (2) is designated unit (a). While the polymer used herein preferably includes recurring units (a) and optional recurring units (b), it may have further copolymerized therein recurring units (c) derived from monomers having an adhesive group such as hydroxy, cyano, carbonyl, ester, ether, lactone, carboxyl, carboxylic anhydride, sulfonic ester, and disulfone group. Inter alia, units having a lactone ring are most preferred.

Examples of monomers from which recurring units (c) are derived are given below.

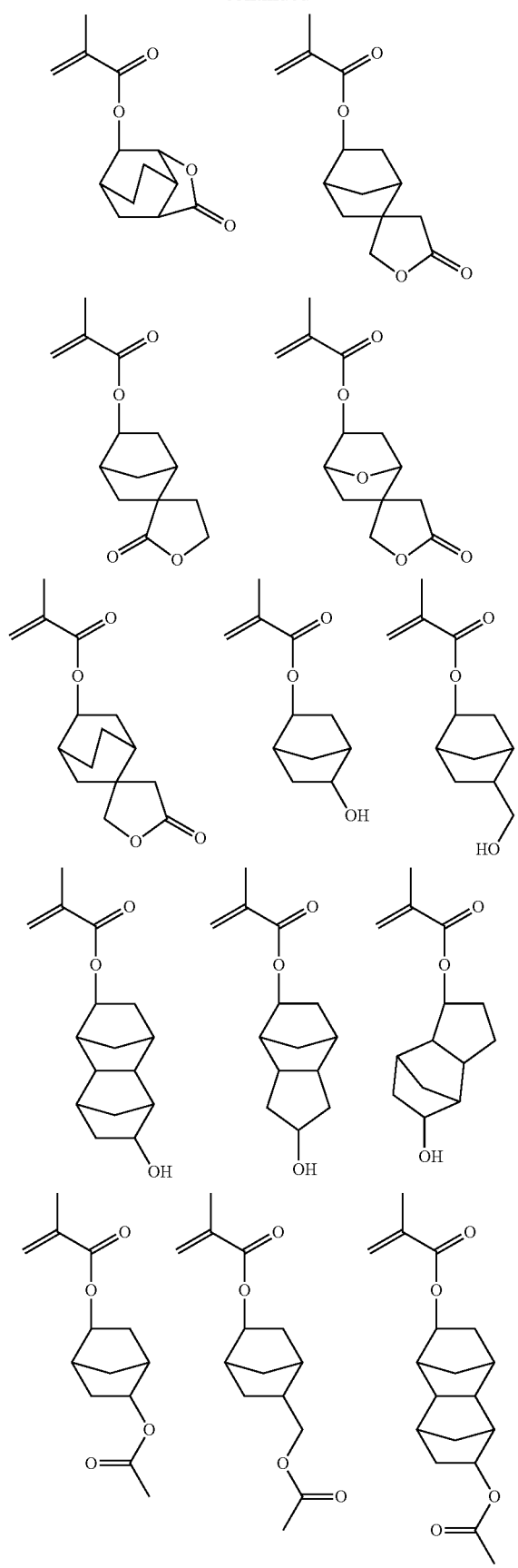
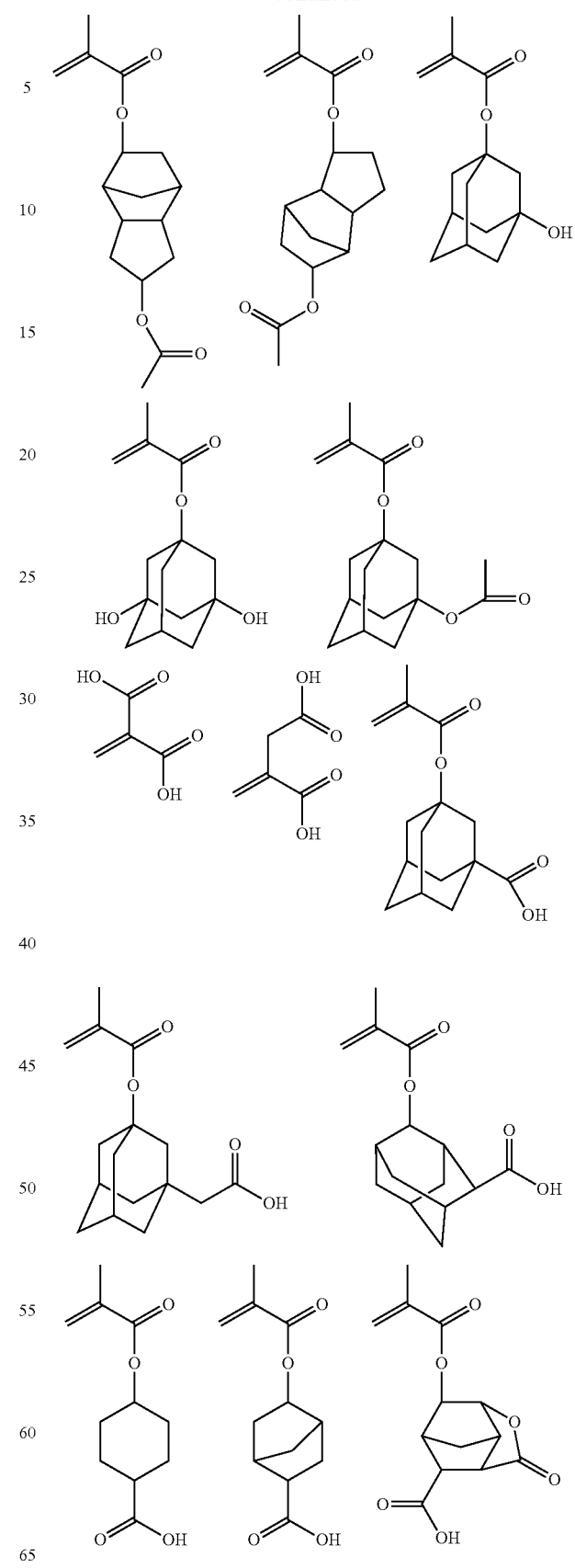

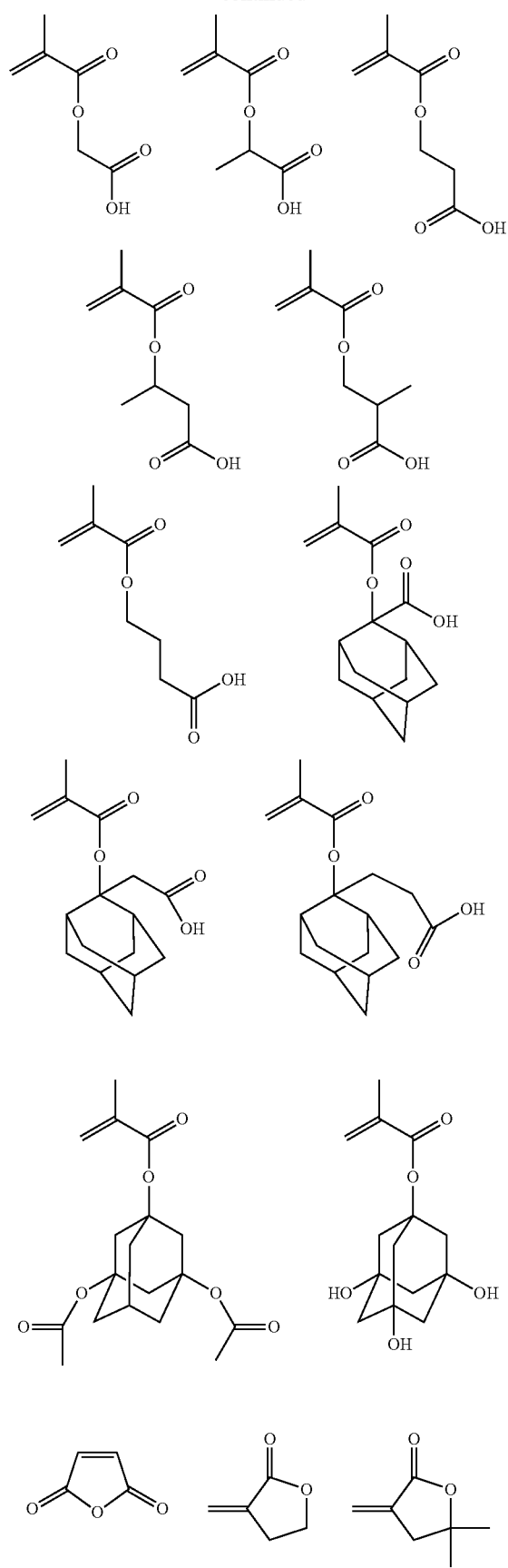
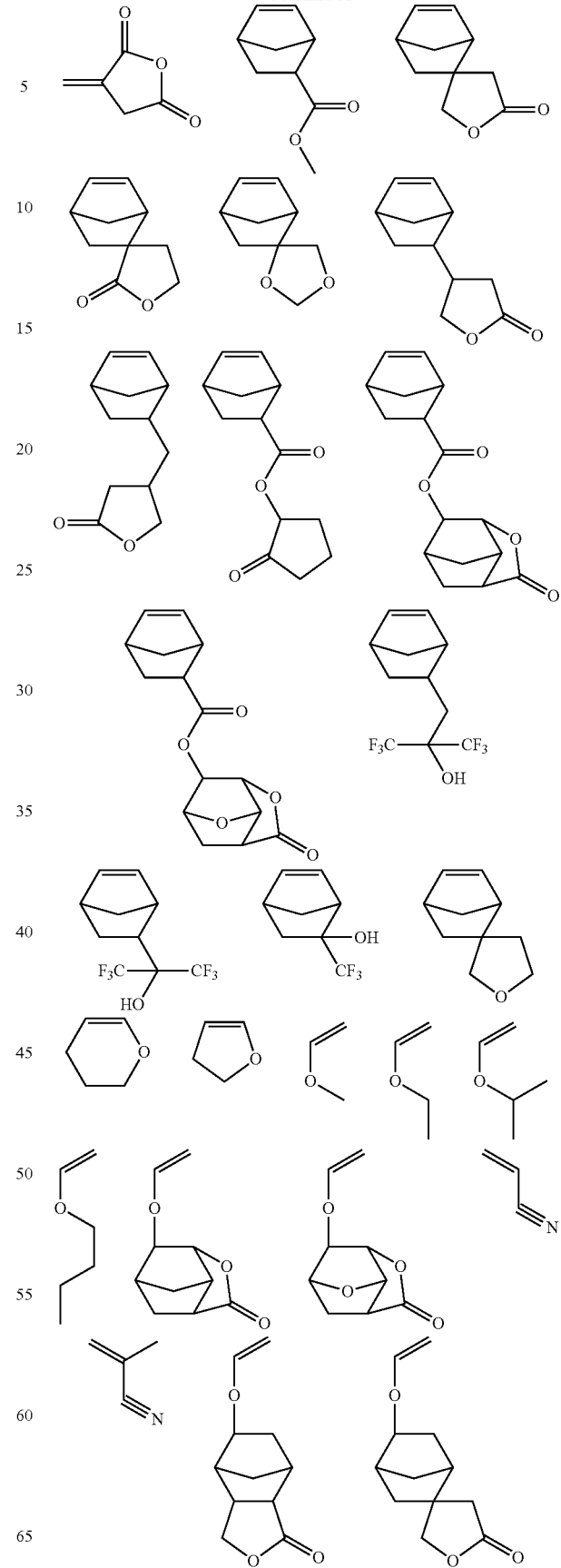

47
-continued
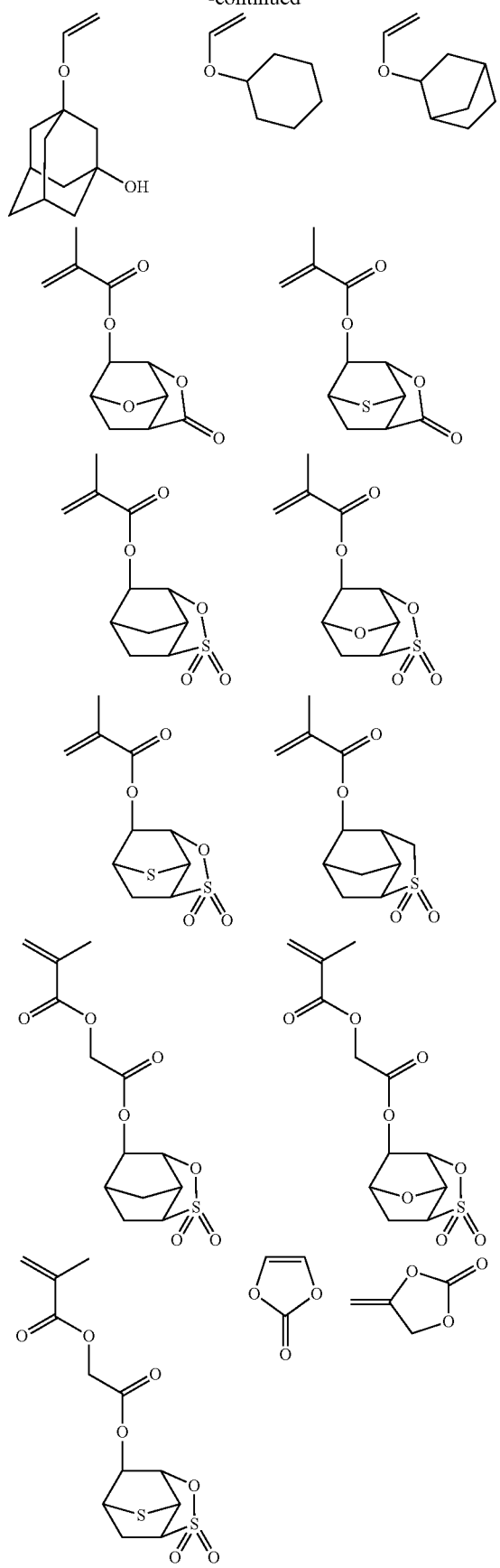
48
-continued
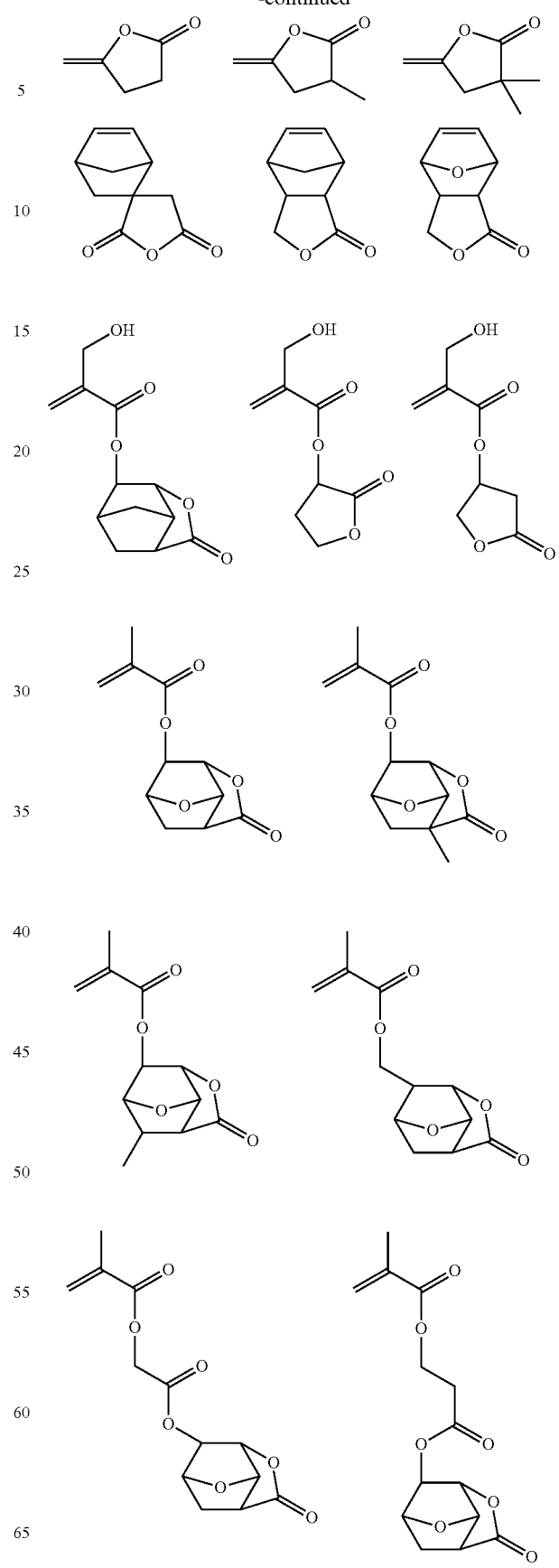

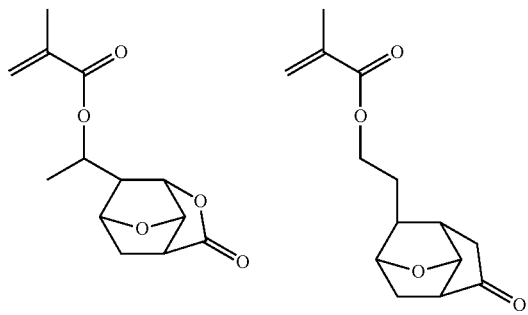
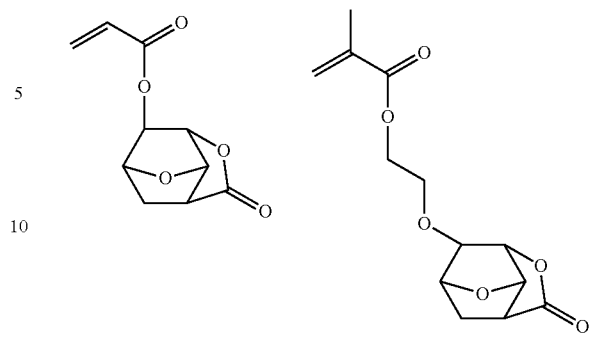
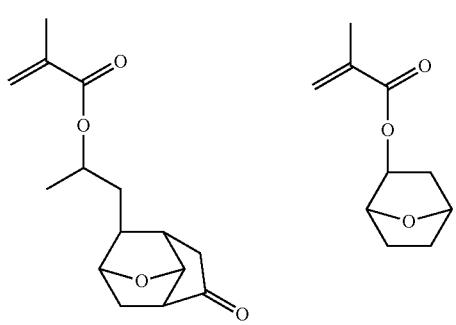
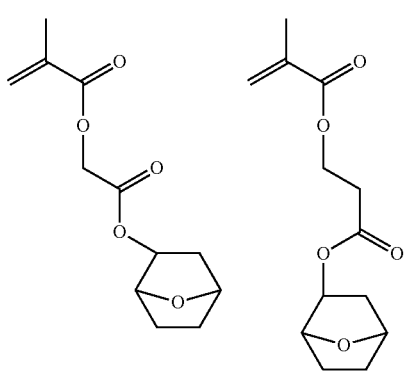
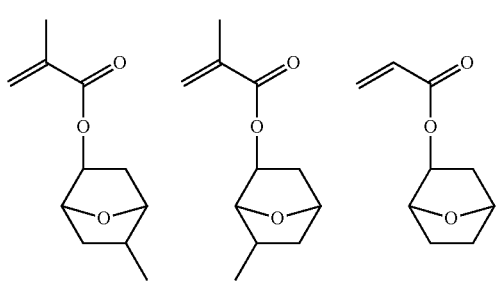
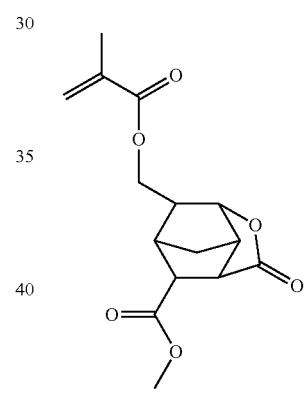
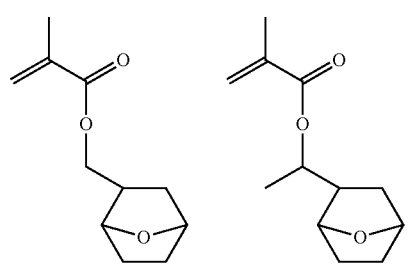
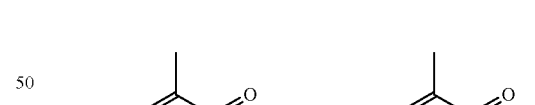
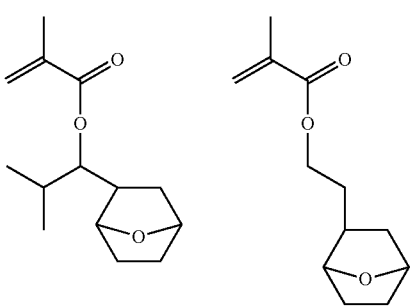
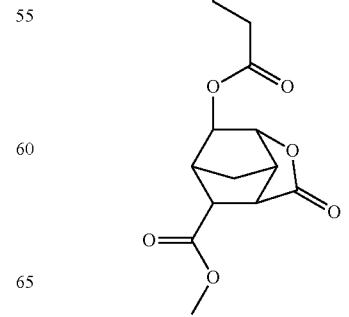

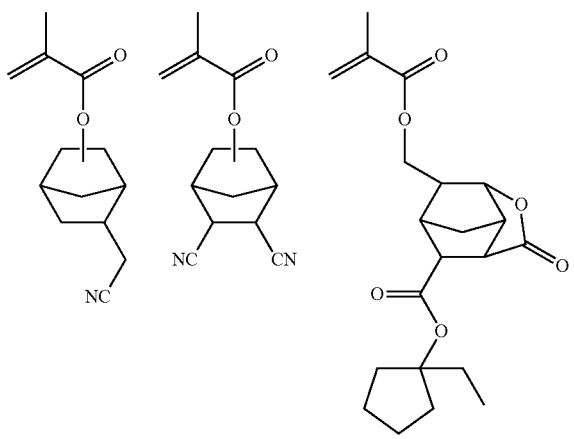
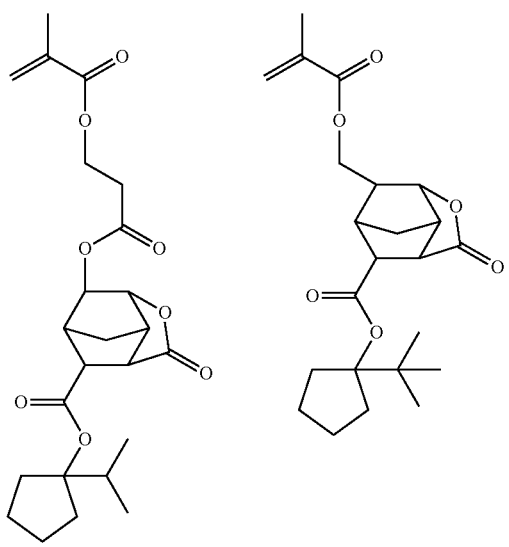
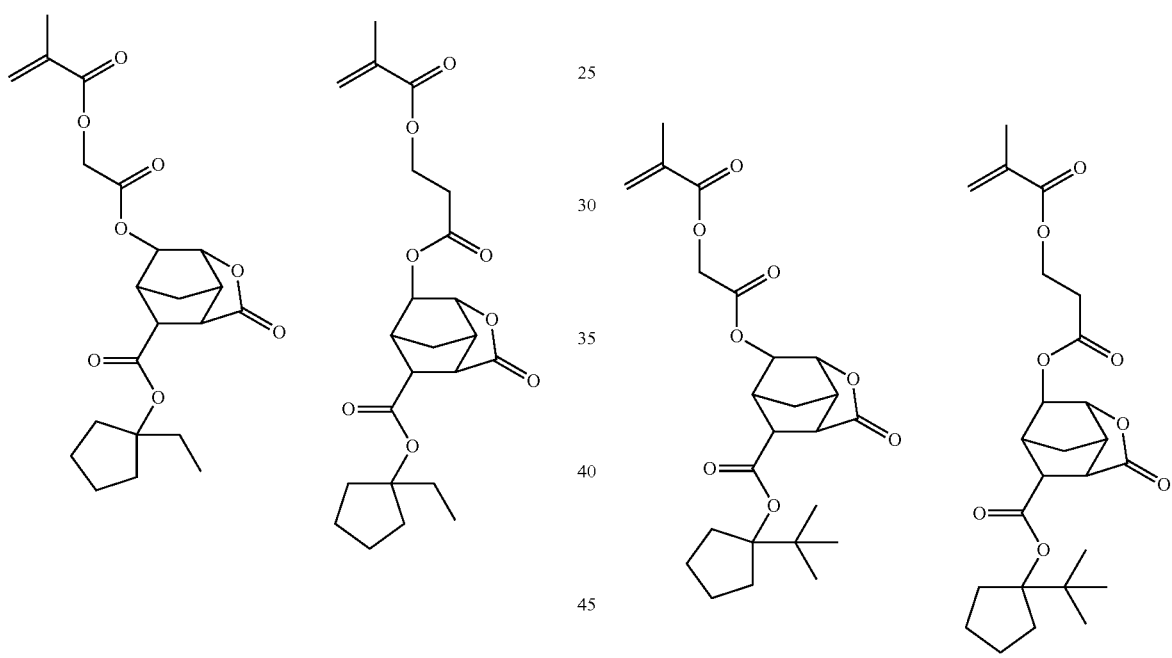
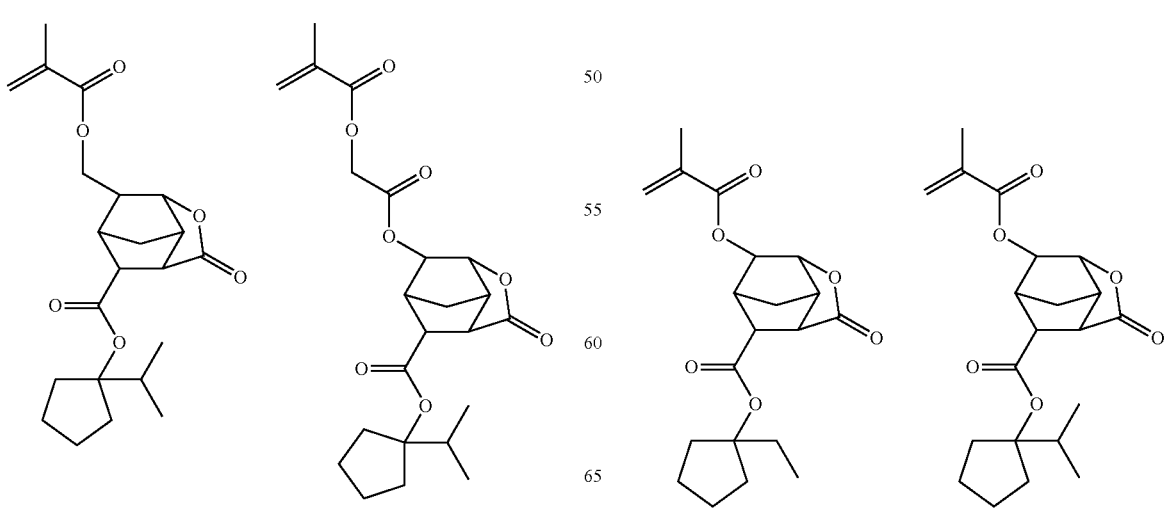

-continued
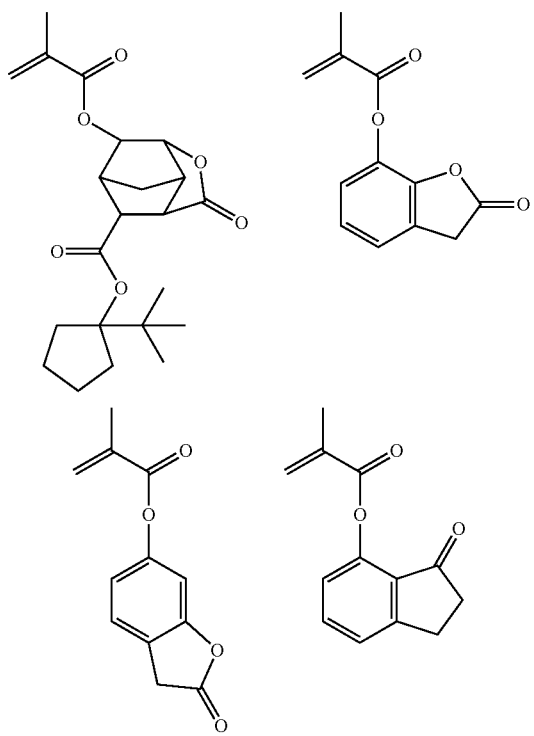
-continued
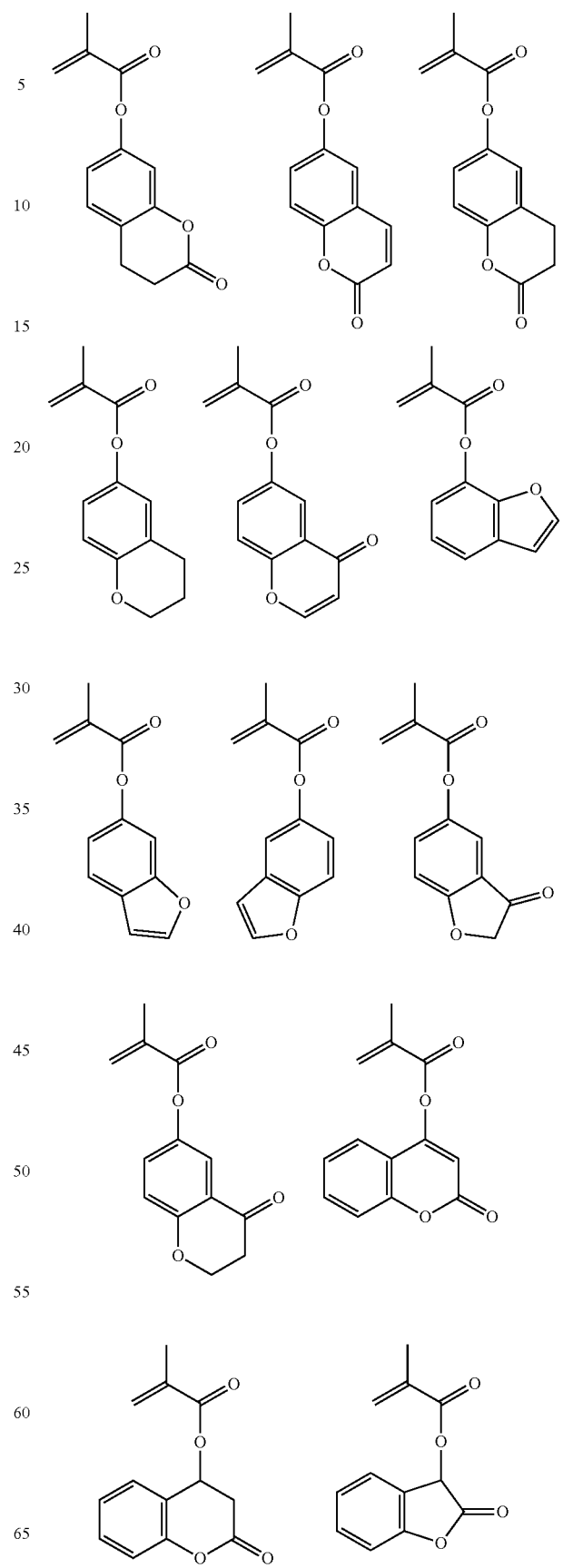

55
-continued
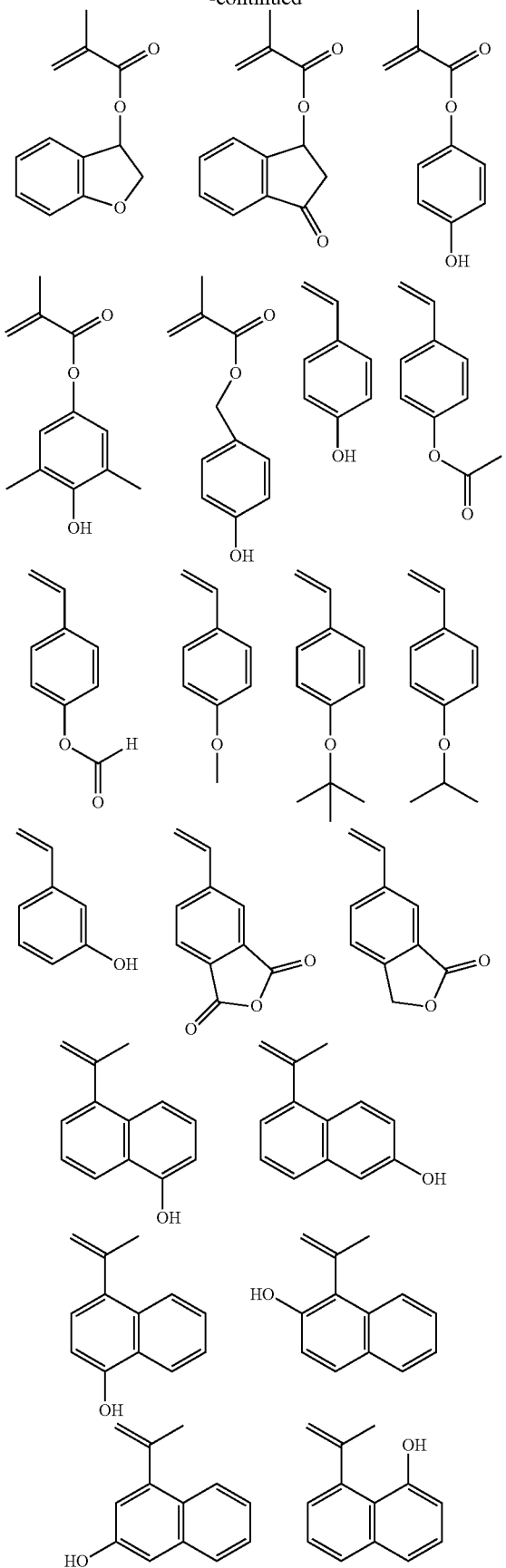
56
-continued
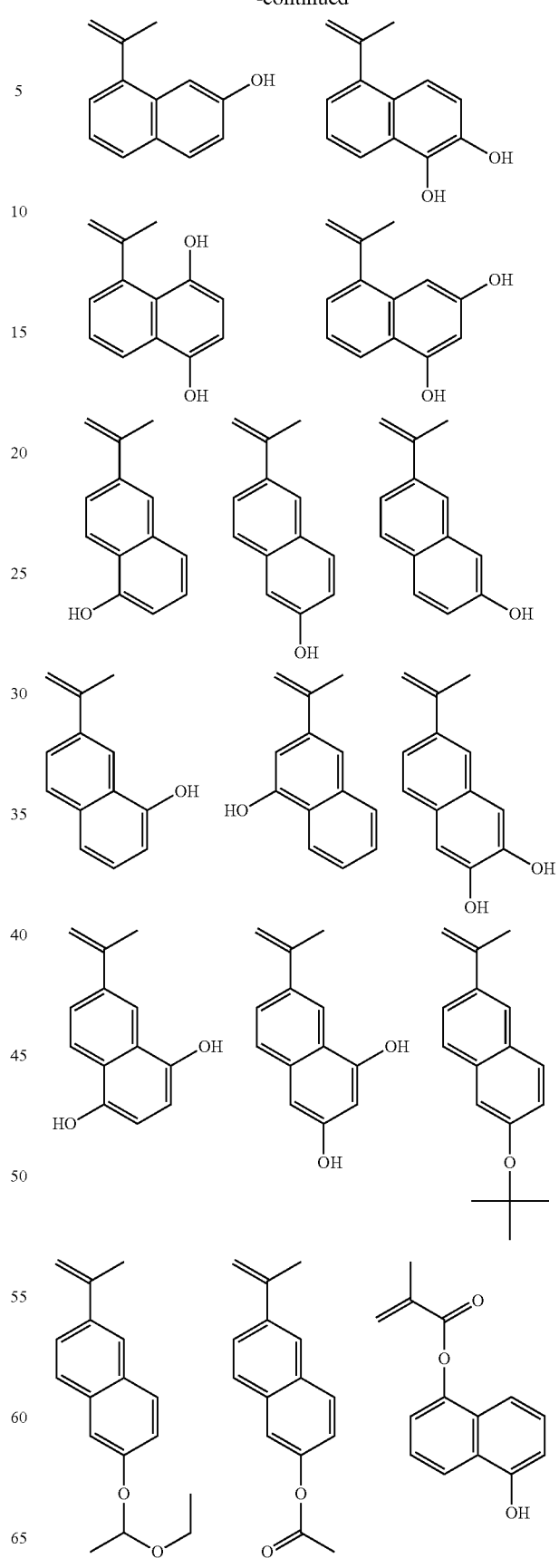

-continued
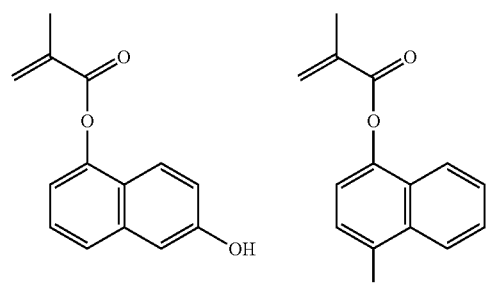
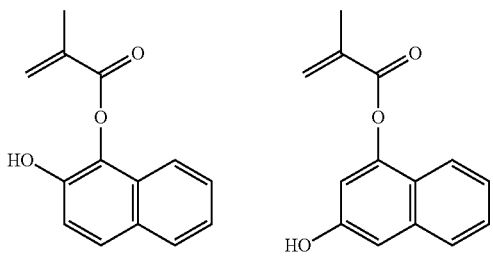
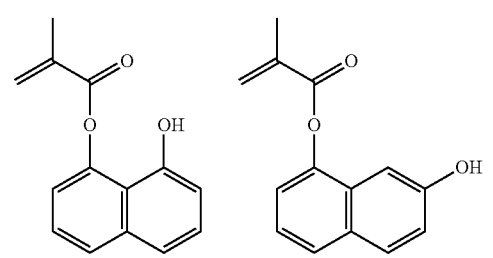
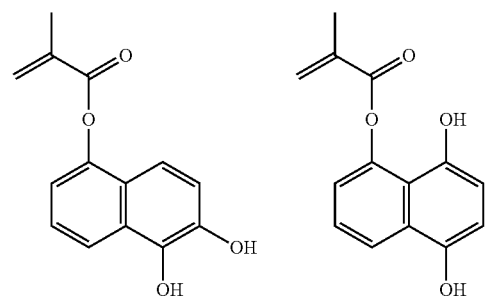
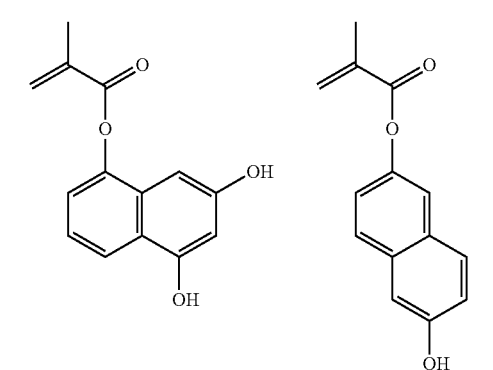
-continued
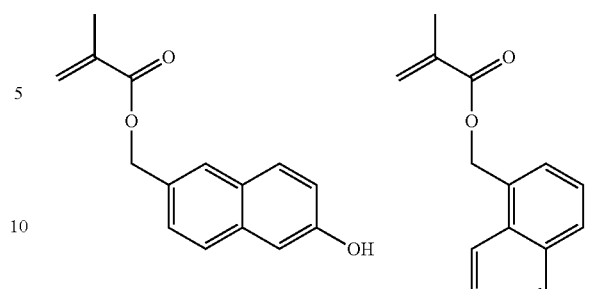
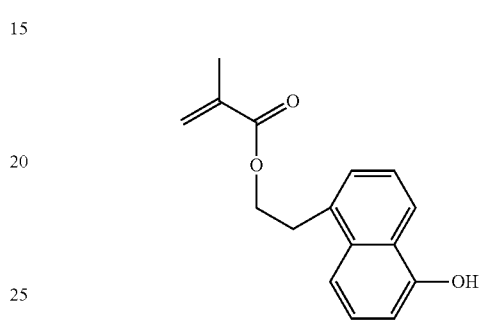
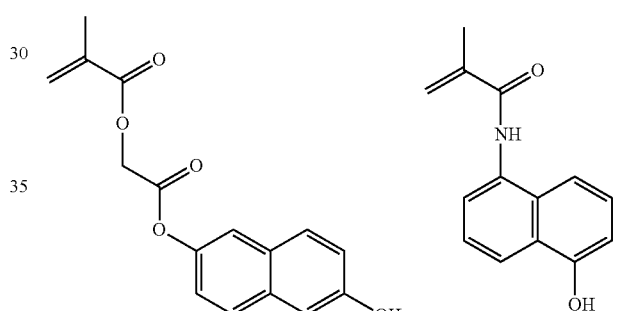
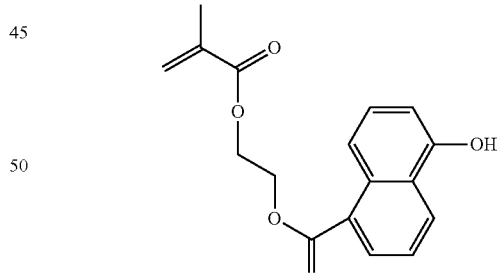
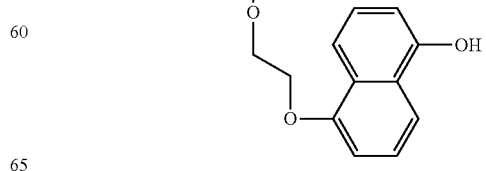

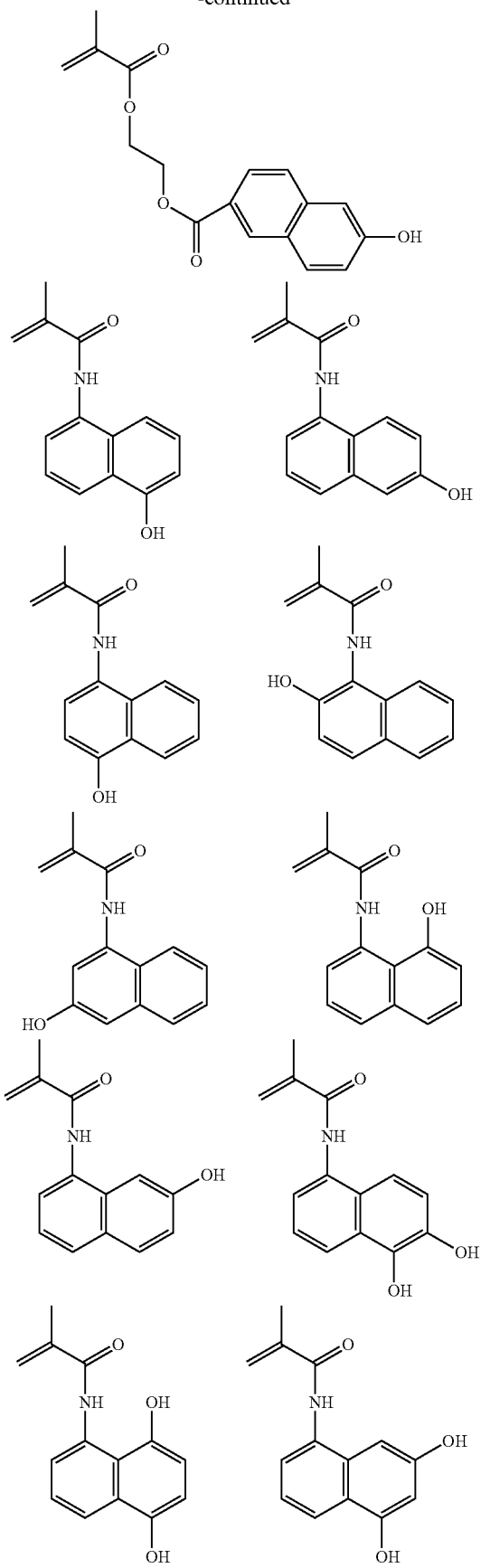
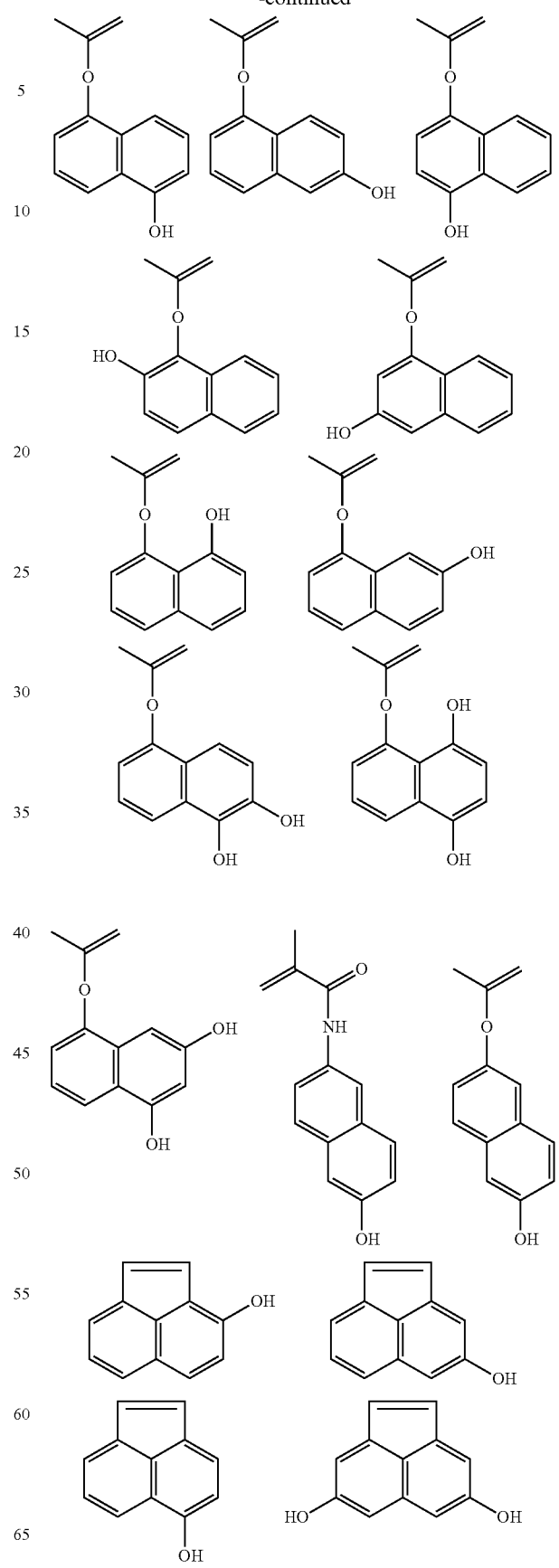

-continued
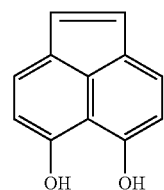 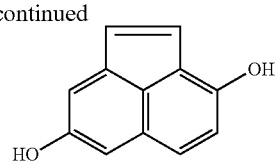
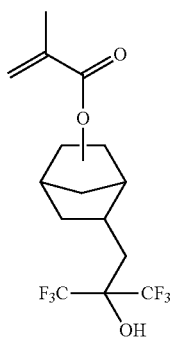 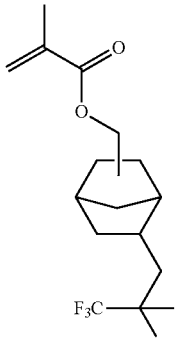
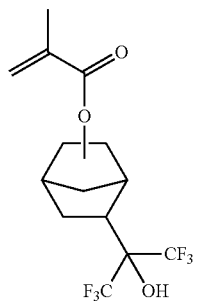 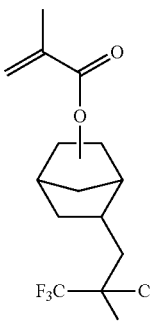 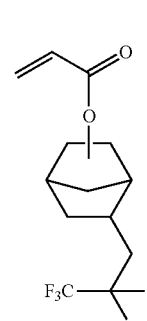
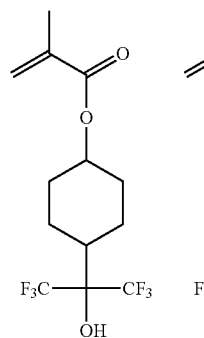 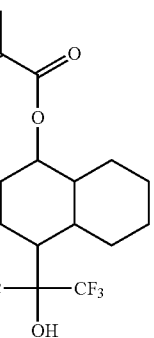
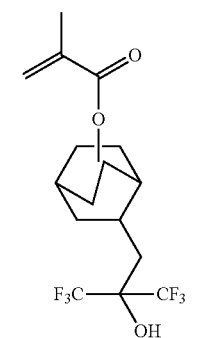 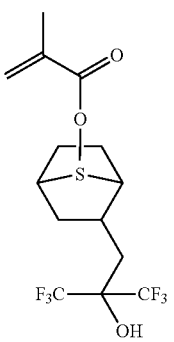 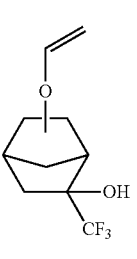
-continued
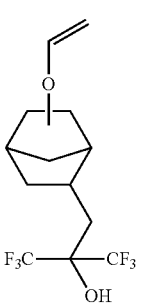 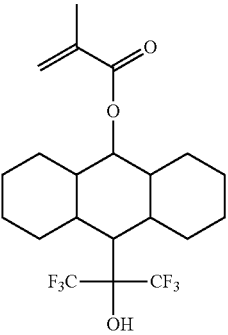
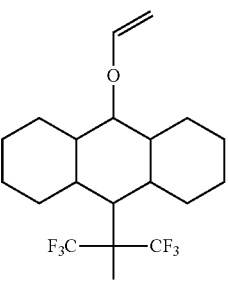 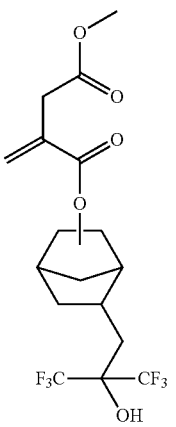
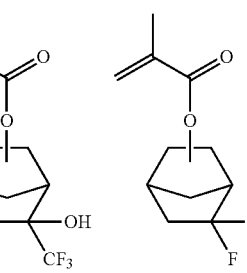 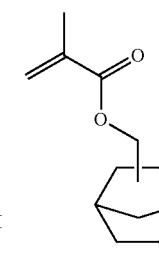
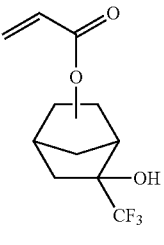 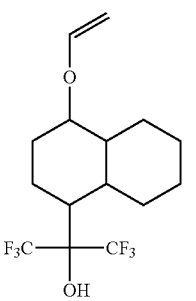

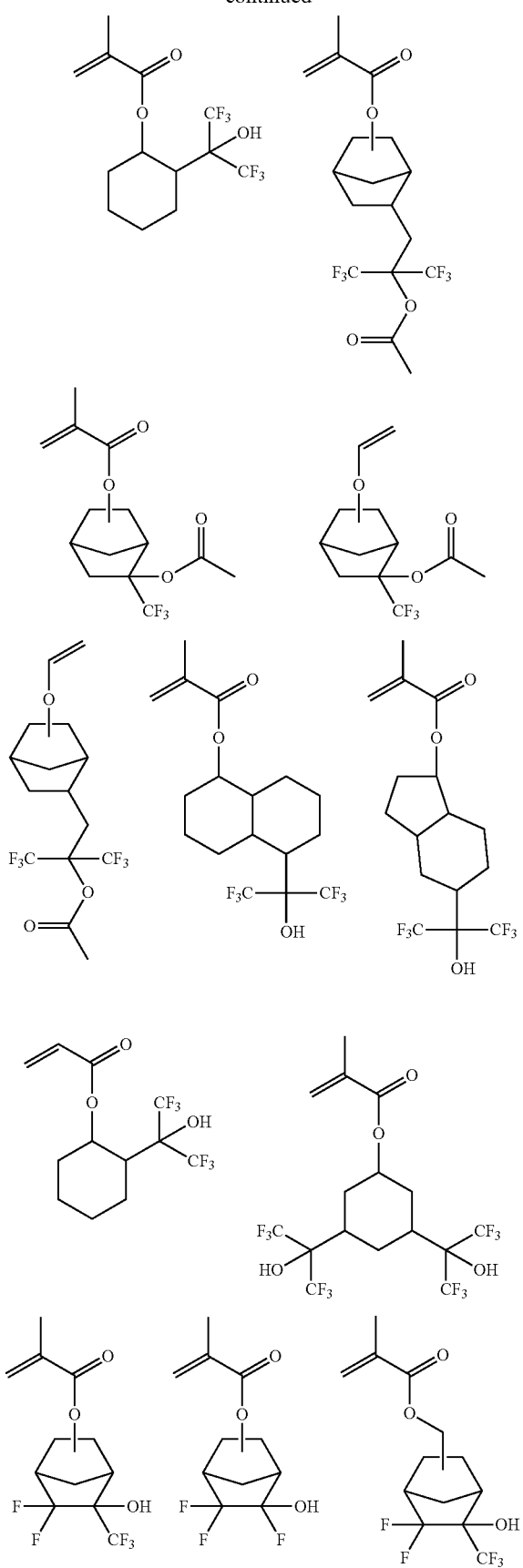
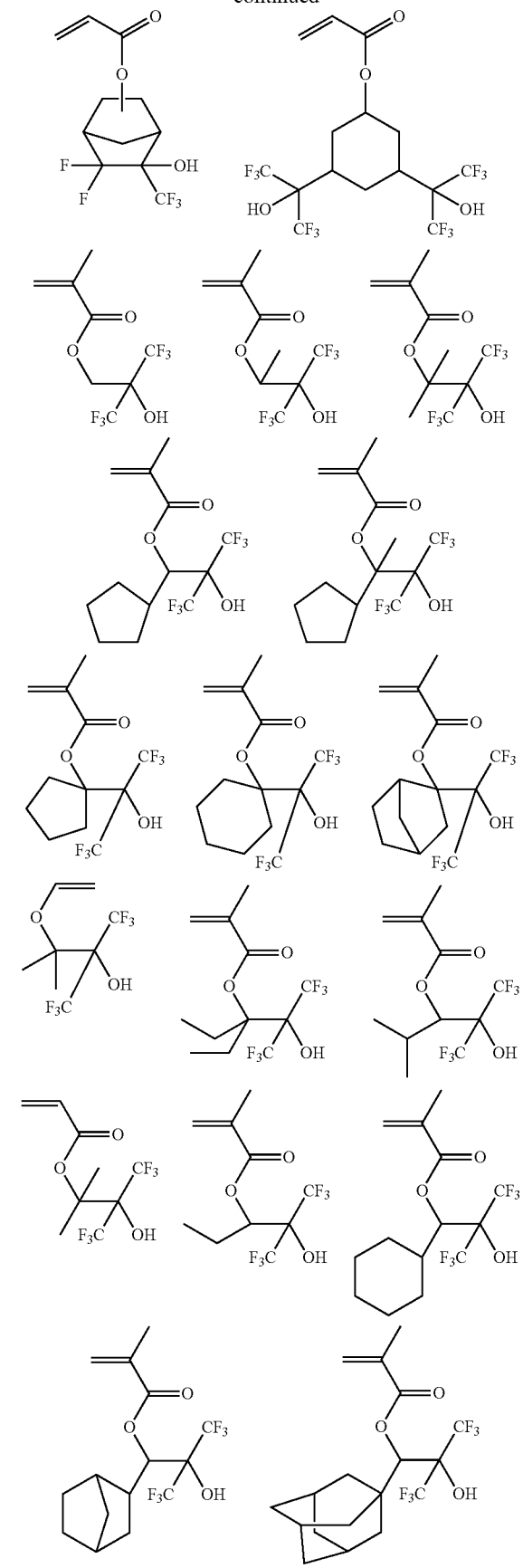

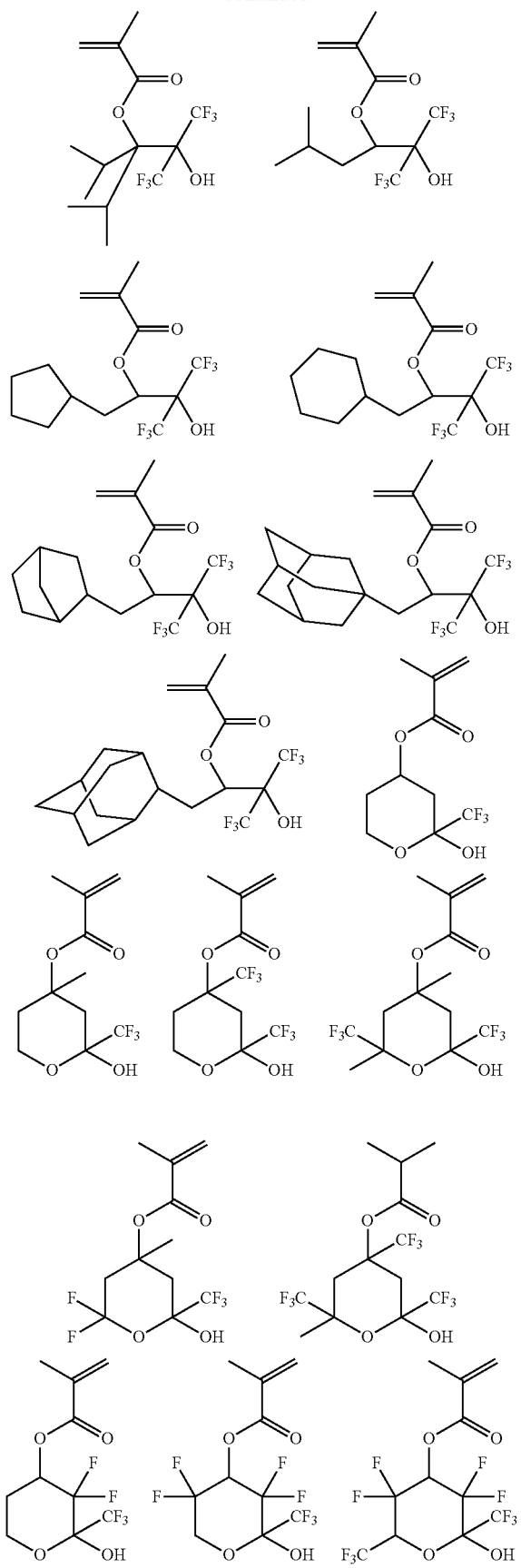
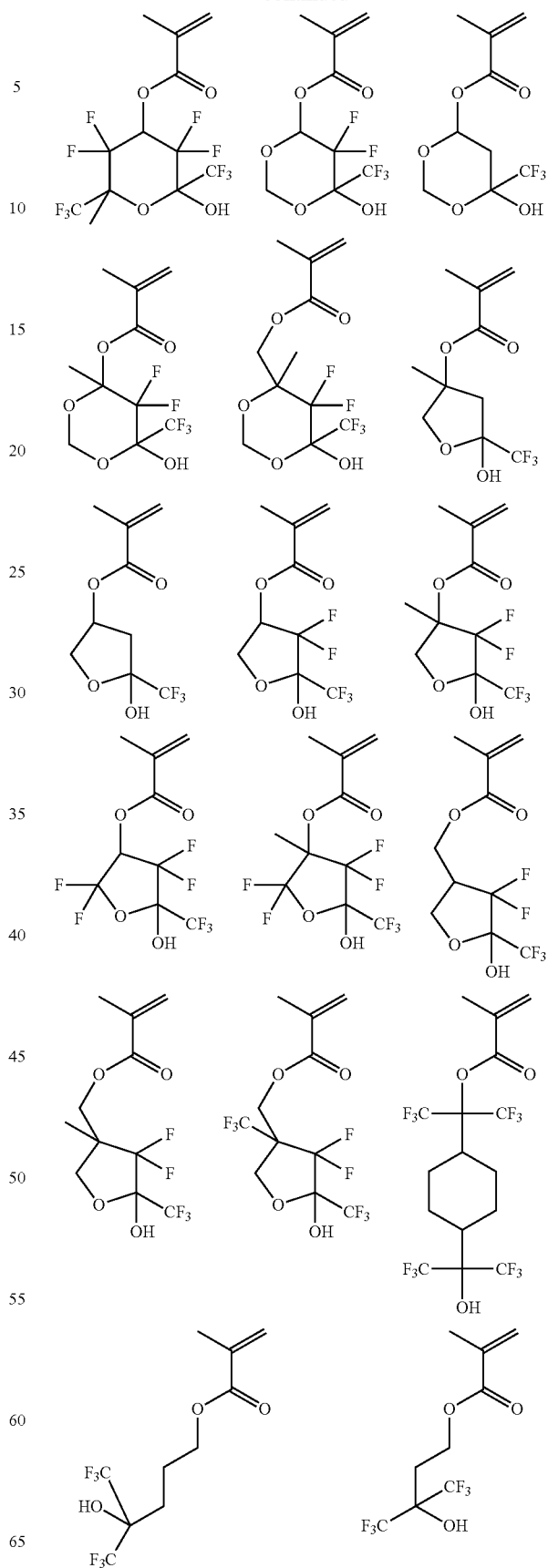

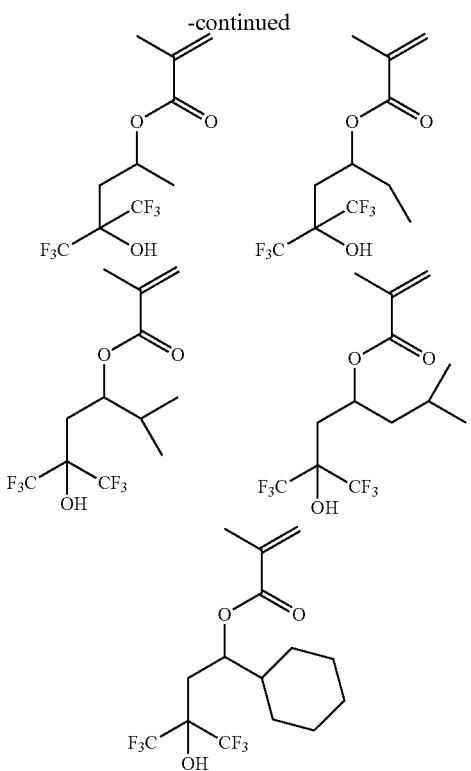

In a preferred embodiment, the copolymer has further copolymerized therein units selected from sulfonium salts (d1) to (d3) represented by the general formulae below.

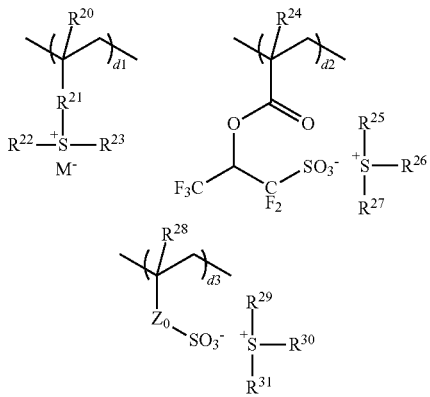

Herein $R^{20}$, $R^{24}$, and $R^{28}$ each are hydrogen or methyl, $R^{21}$ is a single bond, phenylene, —O—$R^{33}$—, or —C(=O)—Y—$R^{33}$—, Y is oxygen or NH, $R^{33}$ is a straight, branched or cyclic $C_1$-$C_6$ alkylene group, alkenylene or phenylene group, which may contain a carbonyl (—CO—), ester (—COO—), ether (—O—) or hydroxyl radical, $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether radical, or a $C_6$-$C_{12}$ aryl, $C_7$-$C_{20}$ aralkyl, or thiophenyl group, $Z_0$ is a single bond, methylene, ethylene, phenylene, fluorophenylene, —O—$R^{32}$—, or —C(=O)—$Z_1$—$R^H$—, $Z_1$ is oxygen or NH, $R^{32}$ is a straight, branched or cyclic $C_1$-$C_6$ alkylene group, alkenylene or phenylene group, which may contain a carbonyl, ester, ether or hydroxyl radical, $M^-$ is a non-nucleophilic counter ion, d1, d2 and d3 are in the range of $0 \le d1 < 0.3$, $0 \le d2 \le 0.3$, $0 \le d3 \le 0.3$, and $0 \le d1+d2+d3 \le 0.3$.

In the copolymer, the recurring units (a), (b), (c), (d1), (d2), and (d3) are preferably present in proportions: $0 < a < 1.0$, $0 \le b < 1.0$, $0 \le c < 1.0$, $0 \le d1 < 0.2$, $0 \le d2 < 0.2$, and $0 \le d3 < 0.2$, and more preferably $0.1 \le a \le 0.8$, $0 \le b \le 0.75$, $0 \le c \le 0.8$, $0 \le d1 < 0.15$, $0 \le d2 < 0.15$, and $0 \le d3 < 0.15$, provided that $a+b+c+d1+d2+d3=1$.

It is noted that the meaning of $a+b=1$, for example, is that in a polymer comprising recurring units (a) and (b), the sum of recurring units (a) and (b) is 100 mol % based on the total amount of entire recurring units. The meaning of $a+b<1$ is that the sum of recurring units (a) and (b) is less than 100 mol % based on the total amount of entire recurring units, indicating the inclusion of other recurring units, for example, units (c), (d1), (d2) and (d3).

The polymer should preferably have a weight average molecular weight (Mw) in the range of 1,000 to 500,000, and more preferably 3,000 to 100,000, as measured in tetrahydrofuran solvent by GPC using polystyrene standards. Outside the range, there may result an extreme drop of etch resistance, and a drop of resolution due to difficulty to gain a dissolution rate difference before and after exposure.

The polymers of the invention are prepared by copolymerization reaction using the compound of formula (1) as a first monomer and polymerizable double bond-bearing compounds as second and subsequent monomers. The copolymerization reaction to produce the inventive polymers may be performed in various modes, preferably radical polymerization, anionic polymerization or coordination polymerization. Preferably the first monomer or acetal compound of formula (1) and the second and subsequent monomers used in copolymerization have an oligomeric or polymeric content of up to 10%, more preferably up to 3%, and even more preferably up to 1% by weight.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction conditions outside the described range may be employed if desired.

A polymer comprising recurring units having formula (2) may also be produced by introducing the desired units by post-protection reaction. Specifically, a polymer may be synthesized by polymerizing a monomer of formula (5) to synthesize an intermediate polymer (6), then effecting post-protection reaction to substitute the desired group for the hydroxyl group in the intermediate polymer as shown below.

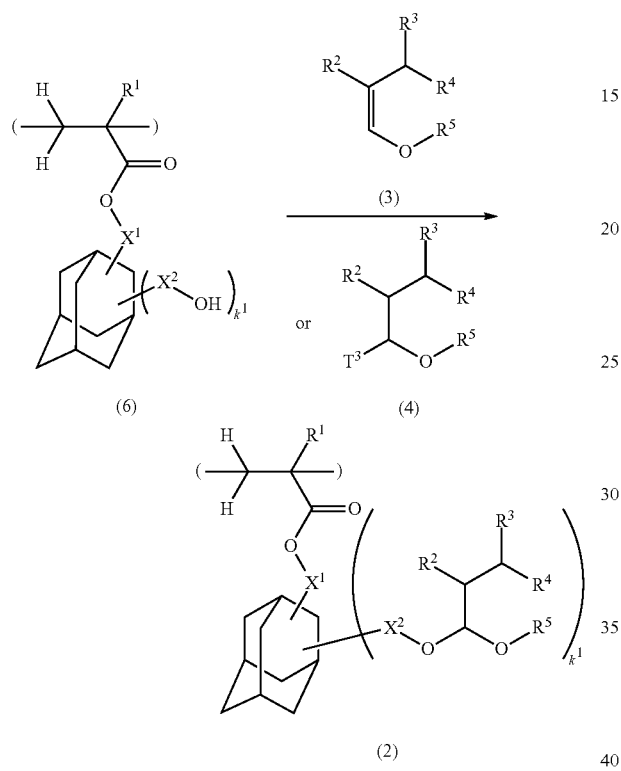

Herein $R^1$ to $R^5$, $X^1$, $X^2$, $k^1$ and $T^3$ are as defined above.

The post-protection reaction may be effected in a similar way to the above-described synthesis of acetal compound (1), but not limited thereto.

Resist Composition

The polymer of the invention is advantageously used as a base resin in a resist composition, specifically a chemically amplified resist composition. The third embodiment of the invention is a resist composition comprising the polymer disclosed herein.

The resist composition is defined herein as comprising (A) a base resin comprising the inventive polymer, (B) an acid generator, (C) an organic solvent, and optionally and preferably (D) a basic compound or quencher and (E) a surfactant.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymerization (ROMP) polymers, and (iv) vinyl ether-maleic anhydride-(meth) acrylic acid derivative copolymers.

Of these, the hydrogenated ROMP polymers are synthesized by the method illustrated in JP-A 2003-66612. Illustrative examples of such hydrogenated polymers include those polymers having the recurring units shown below, but are not limited thereto.

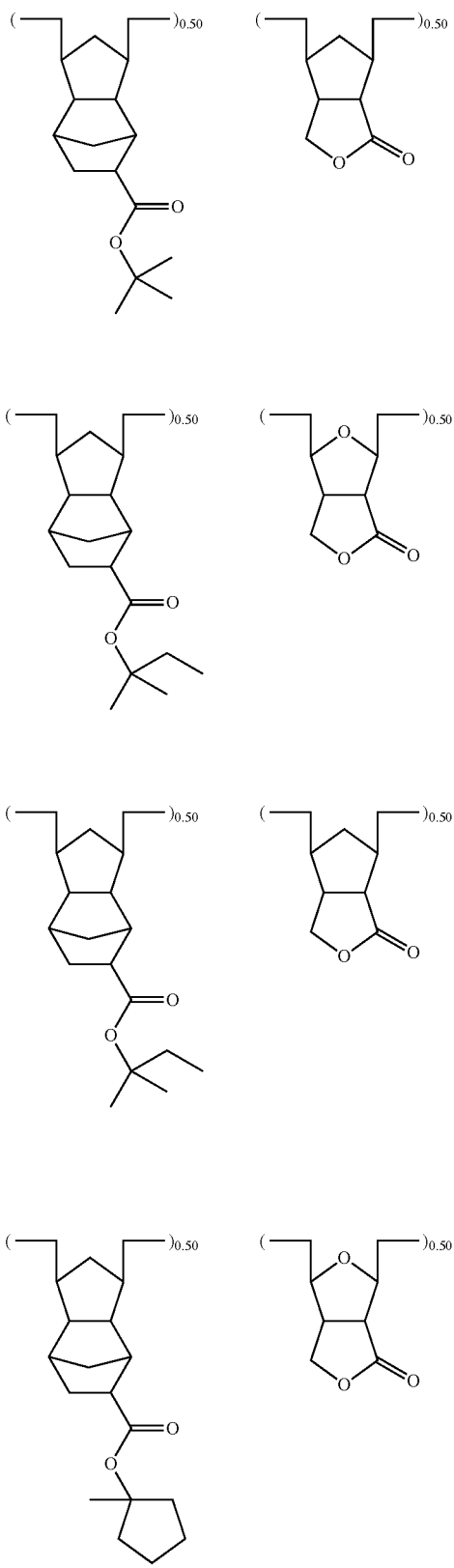

-continued
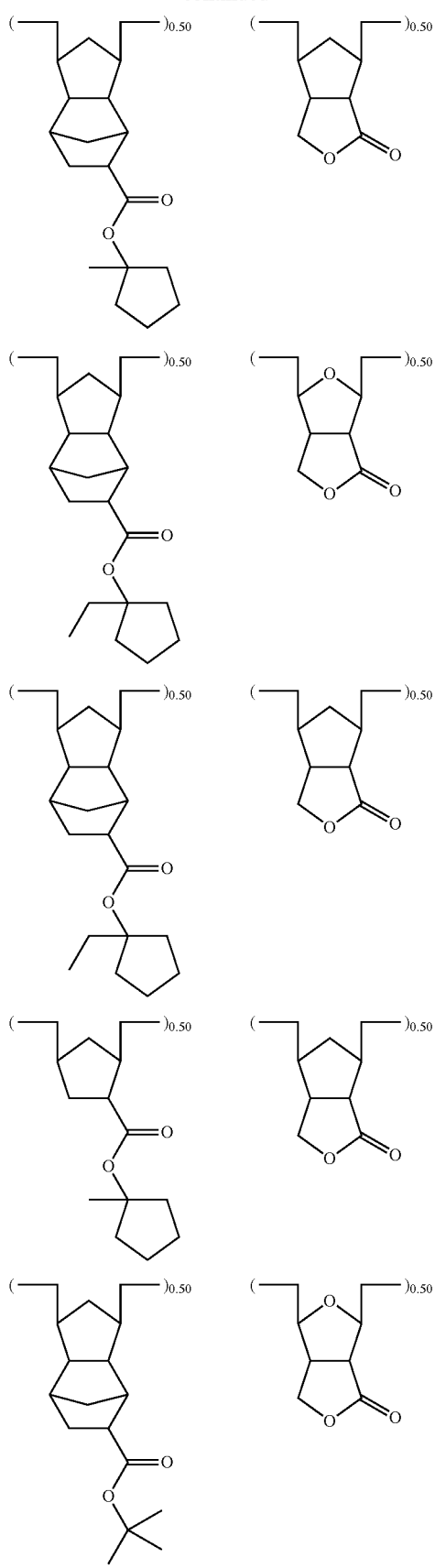
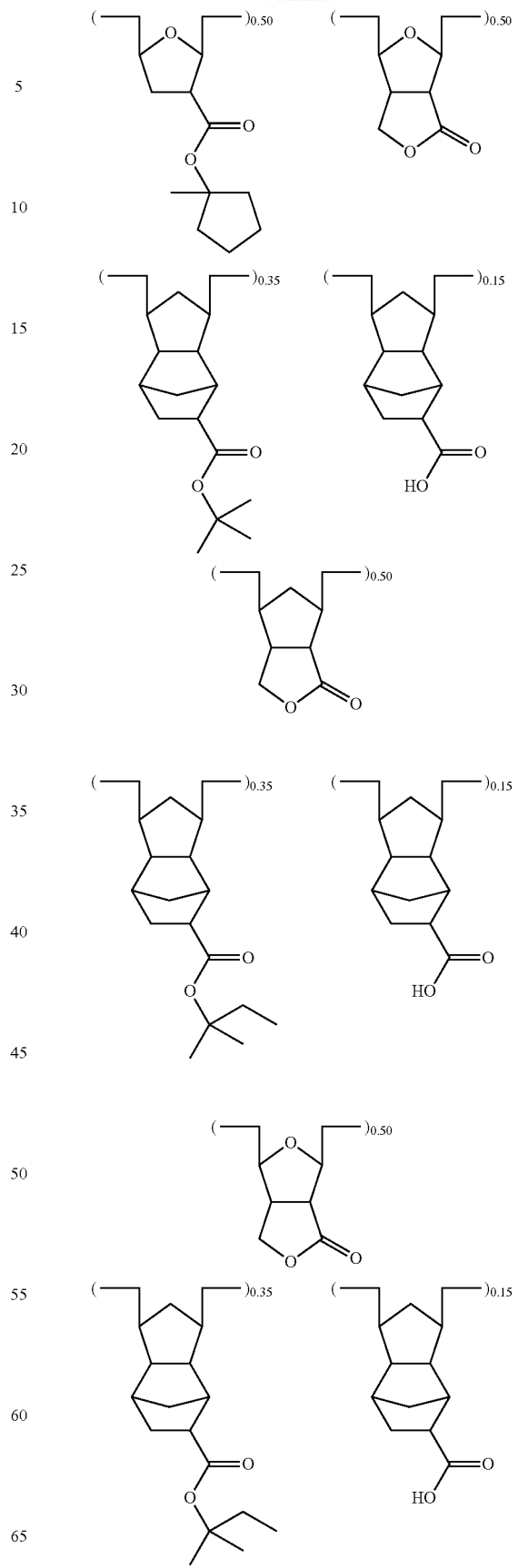

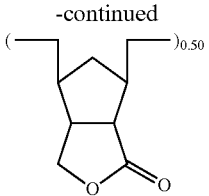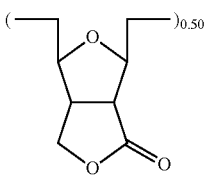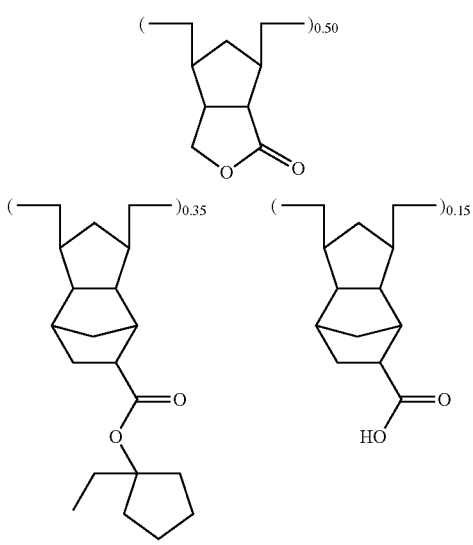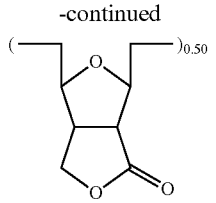

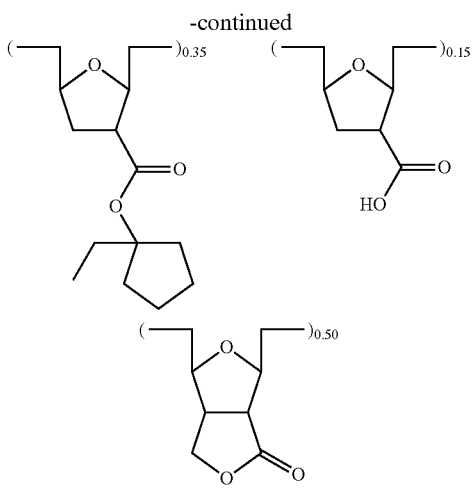

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The polymer is not limited to one type and a mixture of two or more polymers may be added. The use of plural polymers allows for adjustment of resist properties.

Typical of the acid generator (B) used herein is a photoacid generator (PAG). The PAG is any compound capable of generating an acid upon exposure to high-energy radiation. Suitable PAGs include sulfonium salts, iodonium salts, N-sulfonyloxyimide, and oxime-O-sulfonate acid generators. Exemplary acid generators are described in U.S. Pat. No. 7,537,880 (JP-A 2008-111103, paragraphs [0122] to [0142]). The PAGs may be used alone or in admixture of two or more. Where the polymer has a polymerizable acid generator unit selected from recurring units (d1), (d2) and (d3) copolymerized therein, the acid generator need not necessarily be added.

Among others, acid generators having the general formula (7) are more preferred.

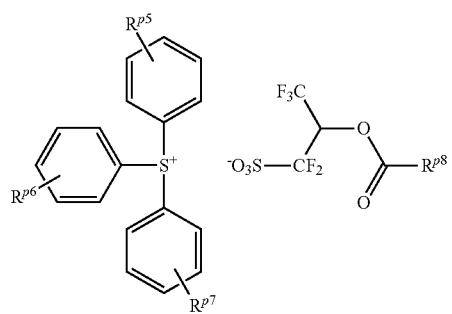

(7)

Herein $R^{P5}$, $R^{P6}$, and $R^{P7}$ are each independently hydrogen or a straight, branched or cyclic, monovalent $C_1$-$C_{20}$ hydrocarbon group which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{P8}$ is a straight, branched or cyclic, monovalent $C_7$-$C_{30}$ hydrocarbon group which may contain a heteroatom, examples of which are exemplified below, but are not limited thereto.

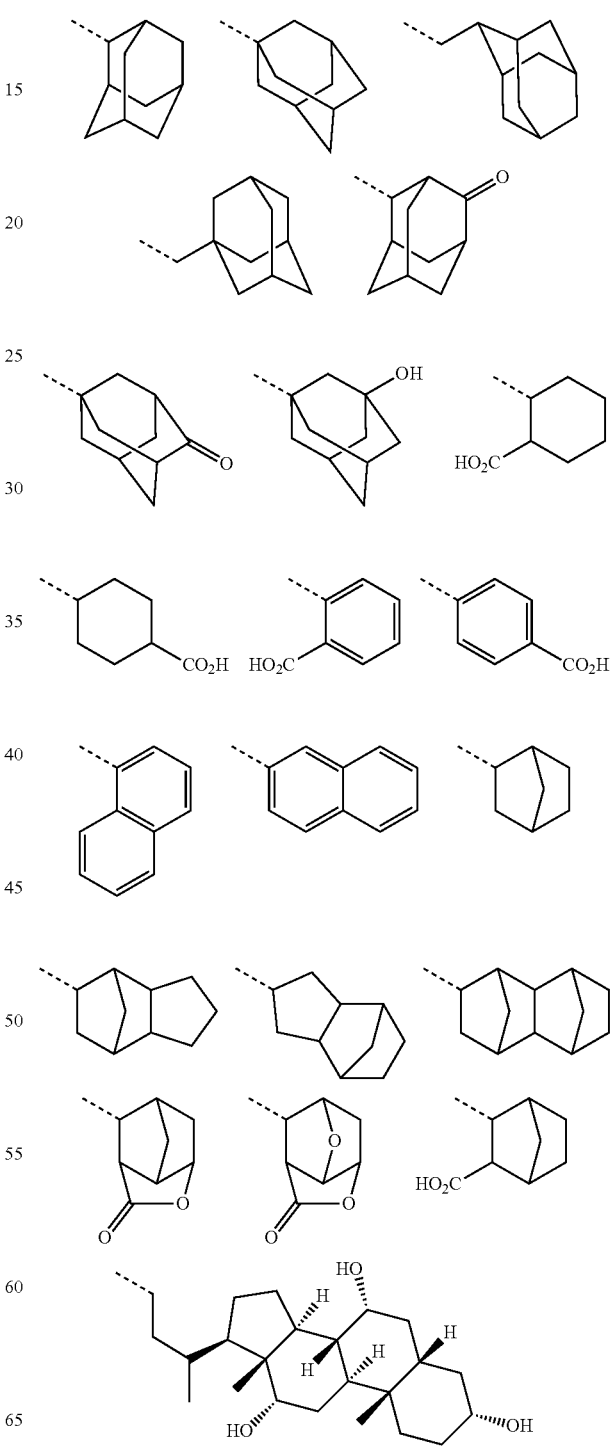

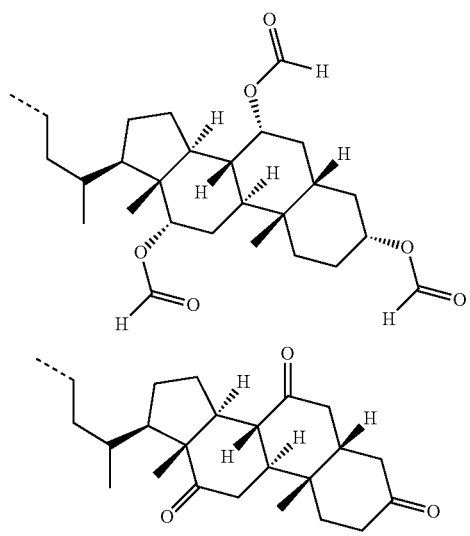
Illustrative examples of acid generators (7) are shown below.
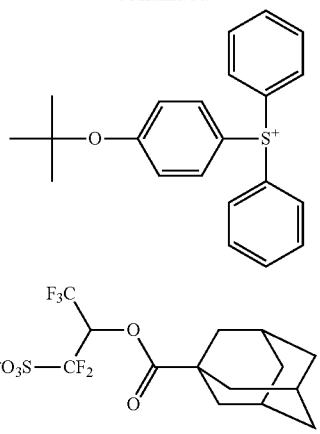
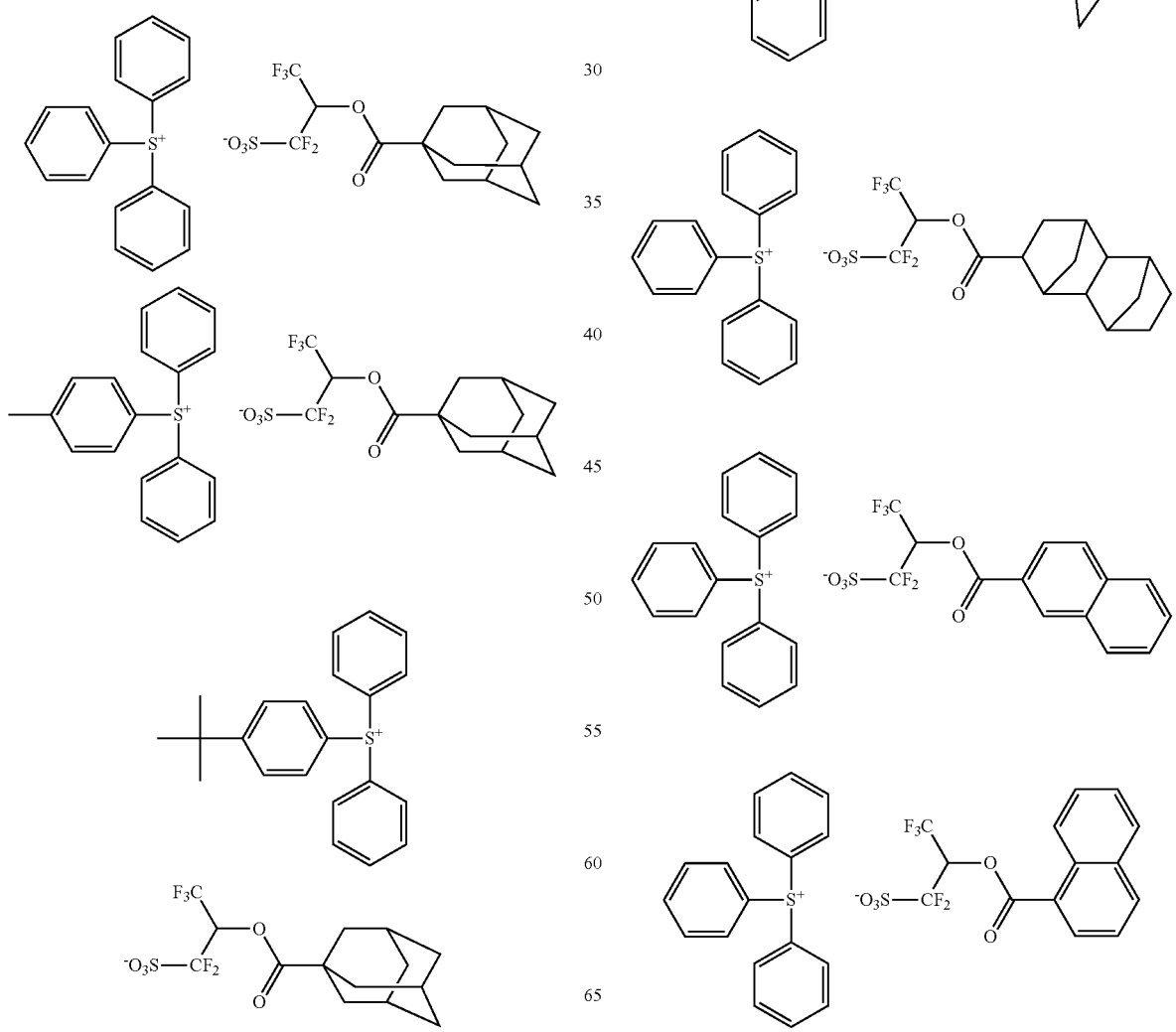

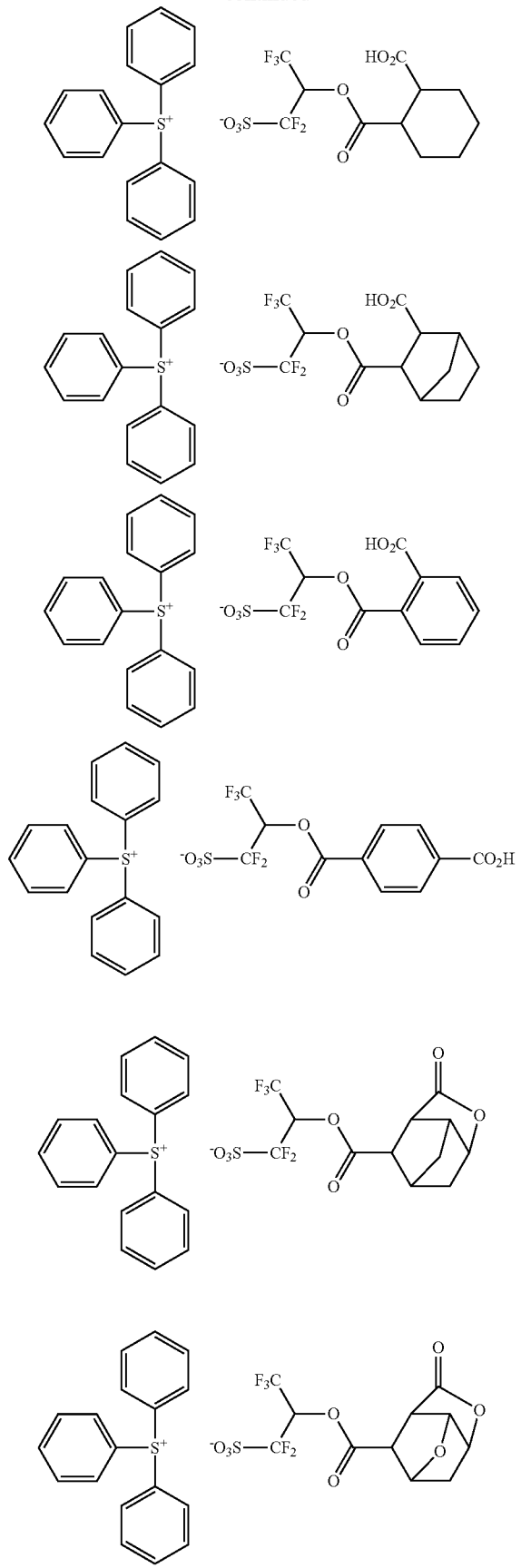
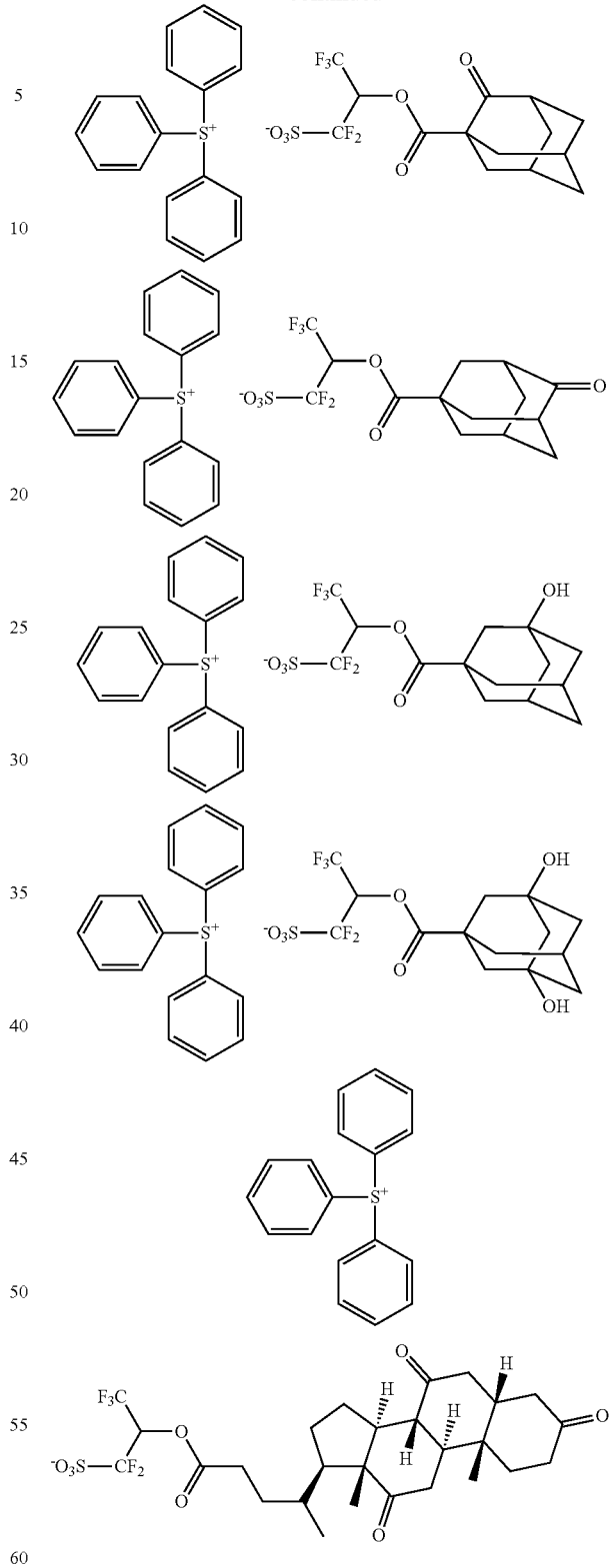
In the chemically amplified resist composition, the PAG (B) may be added in any desired amount as long as the objects of the invention are not compromised. An appropriate amount of the PAG (B) is 0.1 to 30 parts, and more preferably 0.5 to 20 parts by weight per 100 parts by weight of the base resin in the composition. Too high a proportion of the PAG may give rise to problems of degraded resolution and foreign matter upon development and resist film peeling. The PAGs may be used alone or in admixture of two or more. The transmittance of the resist film can be controlled by using a PAG having a low transmittance at the exposure wavelength and adjusting the amount of the PAG added.

It is noted that an acid diffusion controlling function may be provided when two or more PAGs are used in admixture provided that one PAG is an onium salt capable of generating a weak acid. Specifically, in a system using a mixture of a PAG capable of generating a strong acid (e.g., fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid is used, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In the resist composition, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Examples of the organic solvent used herein as component (C) are described in JP-A 2008-111103, paragraphs [0144] to [0145] (U.S. Pat. No. 7,537,880). Specifically, exemplary solvents include ketones such as cyclohexanone and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, and mixtures thereof.

An appropriate amount of the organic solvent used is 100 to 10,000 parts, and especially 300 to 8,000 parts by weight per 100 parts by weight of the base resin.

Examples of the basic compound (or nitrogen-containing organic compound) used herein as component (D) include primary, secondary, and tertiary amine compounds as described in JP-A 2008-111103, paragraphs [0146] to [0164], specifically amine compounds having a hydroxyl, ether, ester, lactone, cyano or sulfonic ester group, and compounds having a carbamate group as described in JP 3790649. An appropriate amount of the basic compound used is 0.0001 to 30 parts, and especially 0.001 to 20 parts by weight per 100 parts by weight of the base resin. Less than 0.0001 phr of the basic compound may achieve no addition effect whereas more than 30 phr may cause an extreme lowering of sensitivity.

The surfactant used herein as component (E) may be typically selected from those described in JP-A 2008-111103, paragraphs [0165] to [0166]. An appropriate amount of the surfactant used is up to 2 parts, and especially up to 1 part by weight per 100 parts by weight of the base resin. When used, the surfactant is preferably added in an amount of at least 0.01 phr.

If desired, other components such as dissolution regulator and acetylene alcohol derivative may be added to the resist composition. The optional components may be added in conventional amounts so long as the objects of the invention are not compromised. Exemplary dissolution regulators are described in JP-A 2008-122932, paragraphs [0155] to [0178], and exemplary acetylene alcohols in paragraphs [0179] to [0182].

Also a polymeric additive may be added for improving the water repellency on surface of a resist film as spin coated. This additive may be used in the topcoatless immersion lithography. These additives have a specific structure with a 1,1,1,3,3,3-hexafluoro-2-propanol residue and are described in JP-A 2007-297590, 2008-111103, 2008-122932, 2009-98638, and 2009-276363. The water repellency improver to be added to the resist should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB and avoiding any hole pattern opening failure after development. The resist composition which can be used herein may comprise a water-repellent polymer having an amino group copolymerized as described in JP-A 2009-31767, a polymer having a sulfonic acid amine salt copolymerized as described in JP-A 2008-107443, and a polymer having carboxylic acid amine salt copolymerized as described in JP-A 2008-239918. An appropriate amount of the water repellency improver is 0.1 to 20 parts, preferably 0.5 to 10 parts by weight per 100 parts by weight of the base resin.

Process

Pattern formation using the resist composition of the invention may be performed by well-known lithography processes. The process generally involves coating, heat treatment (or prebaking), exposure, heat treatment (post-exposure baking, PEB), and development. If necessary, any additional steps may be added.

Now referring to the drawings, the pattern forming process of the invention is illustrated in FIG. 1. First, the positive resist composition is coated on a substrate to form a resist film thereon. Specifically, a resist film 40 of a positive resist composition is formed on a processable substrate 20 disposed on a substrate 10 directly or via an intermediate intervening layer 30 as shown in FIG. 1A. The resist film preferably has a thickness of 10 to 1,000 nm and more preferably 20 to 500 nm. Prior to exposure, the resist film is heated or prebaked, preferably at a temperature of 60 to 180° C., especially 70 to 150° C. for a time of 10 to 300 seconds, especially 15 to 200 seconds.

The substrate 10 used herein is generally a silicon substrate. The processable substrate (or target film) 20 used herein includes $SiO_2$, SiN, SiON, SiOC, p-Si, α-Si, TiN, WSi, BPSG, SOG, Cr, CrO, CrON, MoSi, low dielectric film, and etch stopper film. The intermediate intervening layer 30 includes hard masks of $SiO_2$, SiN, SiON or p-Si, an undercoat in the form of carbon film, a silicon-containing intermediate film, and an organic antireflective coating.

Figure 1B:
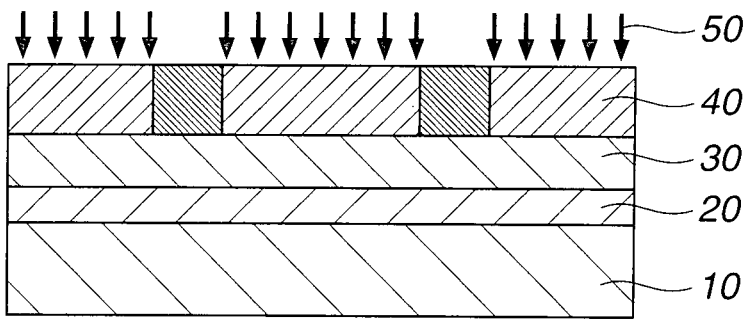
FIG. 1B shows the photoresist film being exposed.

Next comes exposure depicted at 50 in FIG. 1B. For the exposure, preference is given to high-energy radiation having a wavelength of 140 to 250 nm and EUV having a wavelength of 13.5 nm, and especially ArF excimer laser radiation of 193 nm. The exposure may be done either in a dry atmosphere such as air or nitrogen stream or by immersion lithography in water. The ArF immersion lithography uses deionized water or liquids having a refractive index of at least 1 and highly transparent to the exposure wavelength such as alkanes as the immersion solvent. The immersion lithography involves pre-baking a resist film and exposing the resist film to light through a projection lens, with water introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface.

The resist protective film used in the immersion lithography is preferably formed from a solution of a polymer having 1,1,1,3,3,3-hexafluoro-2-propanol residues which is insoluble in water, but soluble in an alkaline developer liquid, in a solvent selected from alcohols of at least 4 carbon atoms, ethers of 8 to 12 carbon atoms, and mixtures thereof. The protective film-forming composition used herein may be based on a polymer comprising recurring units derived from a monomer having a 1,1,1,3,3,3-hexafluoro-2-propanol residue. While the protective film must dissolve in the organic solvent developer, the polymer comprising recurring units derived from a monomer having a 1,1,1,3,3,3-hexafluoro-2-propanol residue dissolves in organic solvent developers. In particular, protective film-forming materials having 1,1,1,3,3,3-hexafluoro-2-propanol residues as described in JP-A 2007-025634, 2008-003569, 2008-81716, and 2008-111089 readily dissolve in organic solvent developers.

In the protective film-forming composition, an amine compound or amine salt or a polymer having copolymerized therein recurring units containing an amine group or amine salt may be used. This component is effective for controlling diffusion of the acid generated in the exposed region of the photoresist film to the unexposed region for thereby preventing any hole opening failure. Useful protective film materials having an amine compound added thereto are described in JP-A 2008-003569, and useful protective film materials having an amino group or amine salt copolymerized are described in JP-A 2007-316448. The amine compound or amine salt may be selected from the compounds enumerated as the basic compound to be added to the resist composition. An appropriate amount of the amine compound or amine salt added is 0.01 to 10 parts, preferably 0.02 to 8 parts by weight per 100 parts by weight of the base resin.

After formation of the photoresist film, deionized water rinsing (or post-soaking) may be carried out for extracting the acid generator and the like from the film surface or washing away particles, or after exposure, rinsing (or post-soaking) may be carried out for removing water droplets left on the resist film. If the acid evaporating from the exposed region during PEB deposits on the unexposed region to deprotect the protective group on the surface of the unexposed region, there is a possibility that the surface edges of holes after development are bridged to close the holes. Particularly in the case of negative development, regions surrounding the holes receive light so that acid is generated therein. There is a possibility that the holes are not opened if the acid outside the holes evaporates and deposits inside the holes during PEB. Provision of a protective film is effective for preventing evaporation of acid and for avoiding any hole opening failure. A protective film having an amine compound or amine salt added thereto is more effective for preventing acid evaporation. On the other hand, a protective film to which an acid compound such as a carboxyl or sulfo group is added or which is based on a polymer having copolymerized therein monomeric units containing a carboxyl or sulfo group is undesirable because of a potential hole opening failure.

The other embodiment of the invention is a process for forming a pattern by applying a resist composition comprising a polymer comprising recurring units having formula (2), an acid generator, and an organic solvent onto a substrate, baking the composition to form a resist film, forming a protective film on the resist film, exposing the resist film to high-energy radiation to define exposed and unexposed regions, baking, and applying a developer to the coated substrate to form a negative pattern wherein the unexposed region of resist film and the protective film are dissolved and the exposed region of resist film is not dissolved. The protective film is preferably formed from a composition comprising a polymer bearing a 1,1,1,3,3,3-hexafluoro-2-propanol residue and an amino group or amine salt-containing compound, or a composition comprising a polymer bearing a 1,1,1,3,3,3-hexafluoro-2-propanol residue and having amino group or amine salt-containing recurring units copolymerized, the composition further comprising an alcohol solvent of at least 4 carbon atoms, an ether solvent of 8 to 12 carbon atoms, or a mixture thereof.

With respect to the recurring units having a 1,1,1,3,3,3-hexafluoro-2-propanol residue, those monomers having a $—C(CF_3)(OH)$ group, i.e., a carbon atom having $CF_3$ and OH radicals bonded thereto are preferably selected among the exemplary monomers listed for the recurring unit (c) (some monomers in the last but one and two lists, and all monomers in the last list). The amino group-containing compound may be selected from the exemplary amine compounds (to be added to photoresist compositions) described in JP-A 2008-111103, paragraphs [0146] to [0164]. As the amine salt-containing compound, salts of the foregoing amine compounds with carboxylic acid or sulfonic acid may be used.

Suitable alcohols of at least 4 carbon atoms include 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether solvents of 8 to 12 carbon atoms include di-n-butyl ether, diisobutyl ether, di-sec-butyl ether, di-n-pentyl ether, diisopentyl ether, di-sec-pentyl ether, di-t-amyl ether, and di-n-hexyl ether.

Exposure is preferably performed in an exposure dose of about 1 to 200 mJ/cm², more preferably about 10 to 100 mJ/cm². This is followed by baking (PEB) on a hot plate at 60 to 150° C. for 1 to 5 minutes, preferably at 80 to 120° C. for 1 to 3 minutes.

Figure 1C:
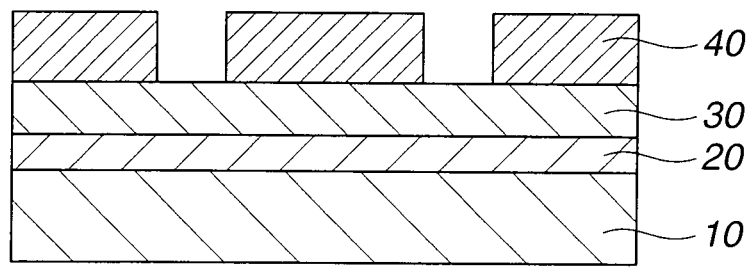
FIG. 1C shows the photoresist film being developed with organic solvent.

Thereafter the exposed resist film is developed with a developer consisting of an organic solvent for 0.1 to 3 minutes, preferably 0.5 to 2 minutes by any conventional techniques such as dip, puddle and spray techniques. In this way, the unexposed region of resist film was dissolved away, leaving a negative resist pattern 40 on the substrate 10 as shown in FIG. 1C. The developer used herein is preferably selected from among ketones such as 2-octanone, 2-nonanone, 2-heptanone, 3-heptanone, 4-heptanone, 2-hexanone, 3-hexanone, diisobutyl ketone, methylcyclohexanone, acetophenone, and methylacetophenone, and esters such as propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-t-amyl ether, and di-n-hexyl ether. Suitable aromatic solvents include toluene, xylene, ethylbenzene, isopropylbenzene, t-butylbenzene, and mesitylene. The solvents may be used alone or in admixture.

Where a hole pattern is formed by negative tone development, exposure by double dipole illuminations of X- and Y-direction line patterns provides the highest contrast light. The contrast may be further increased by combining dipole illumination with s-polarized illumination.

In a preferred embodiment, a halftone phase shift mask bearing a lattice-like shifter pattern is used, whereby a pattern of holes is formed at the intersections between gratings of the lattice-like shifter pattern after development. More preferably the halftone phase shift mask bearing a lattice-like shifter pattern has a transmittance of 3% to 15%.

In a more preferred embodiment, a phase shift mask including a lattice-like first shifter having a line width equal to or less than a half pitch and a second shifter arrayed on the first shifter and consisting of lines whose on-wafer size is 2 to 30 nm thicker than the line width of the first shifter is used, whereby a pattern of holes is formed only where the thick shifter is arrayed. Alternatively, a phase shift mask including a lattice-like first shifter having a line width equal to or less than a half pitch and a second shifter arrayed on the first shifter and consisting of dots whose on-wafer size is 2 to 100 nm thicker than the line width of the first shifter is used, whereby a pattern of holes is formed only where the thick shifter is arrayed.

Figure 2:
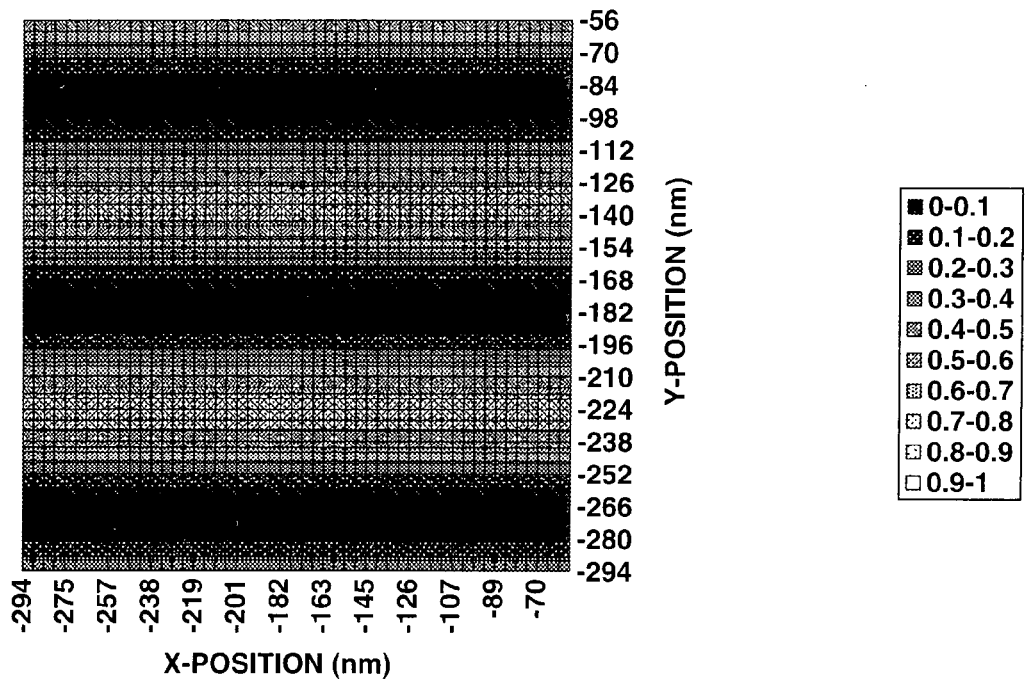
FIG. 2 is an optical image of X-direction lines having a pitch of 90 nm and a line size of 45 nm printed under conditions: ArF excimer laser of wavelength 193 nm, NA 1.3 lens, dipole illumination, 6% halftone phase shift mask, and s-polarization.

FIG. 2 is an optical image of X-direction lines having a pitch of 90 nm and a line size of 45 nm printed under conditions: ArF excimer laser of wavelength 193 nm, NA 1.3 lens, dipole illumination, 6% halftone phase shift mask, and s-polarization.

Figure 3:
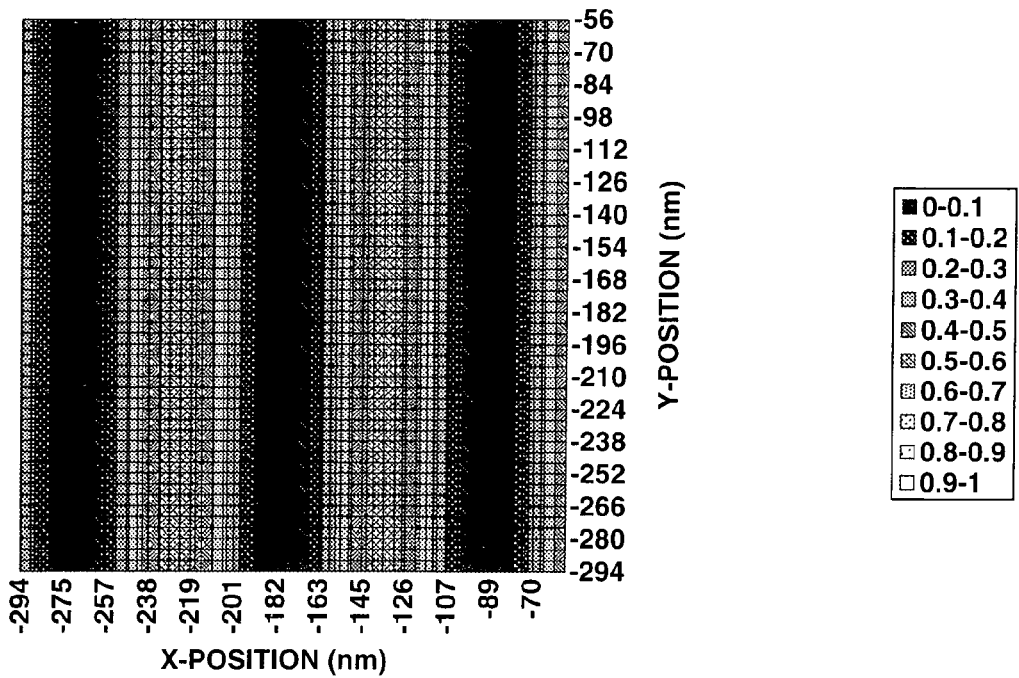
FIG. 3 is an optical image of Y-direction lines like FIG. 2.

FIG. 3 is an optical image of Y-direction lines having a pitch of 90 nm and a line size of 45 nm printed under conditions: ArF excimer laser of wavelength 193 nm, NA 1.3 lens, dipole illumination, 6% halftone phase shift mask, and s-polarization. A black area is a light shielded area while a white area is a high light intensity area. A definite contrast difference is recognized between white and black, indicating the presence of a fully light shielded area.

Figure 4:
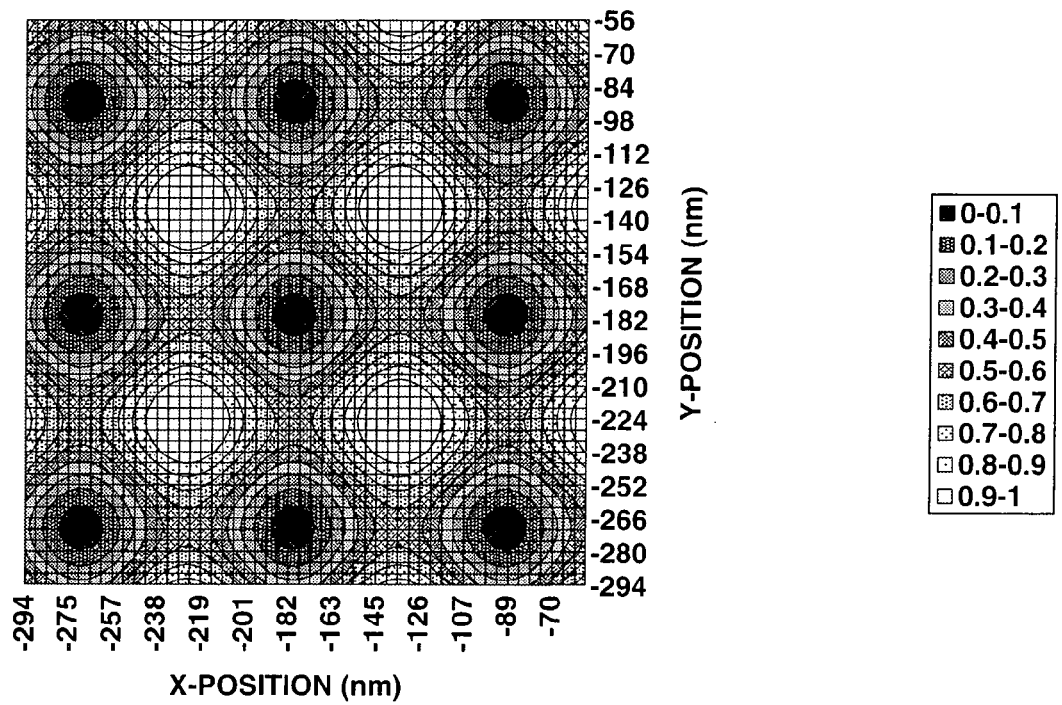
FIG. 4 shows a contrast image obtained by overlaying the optical image of X-direction lines in FIG. 2 with the optical image of Y-direction lines in FIG. 3.

FIG. 4 shows a contrast image obtained by overlaying the optical image of X-direction lines in FIG. 2 with that of Y-direction lines in FIG. 3. Against the expectation that a combination of X and Y lines may form a lattice-like image, weak light black areas draw circular shapes. As the pattern (circle) size becomes larger, the circular shape changes to a rhombic shape to merge with adjacent ones. As the circle size becomes smaller, circularity is improved, which is evidenced by the presence of a fully light shielded small circle.

Figure 21:
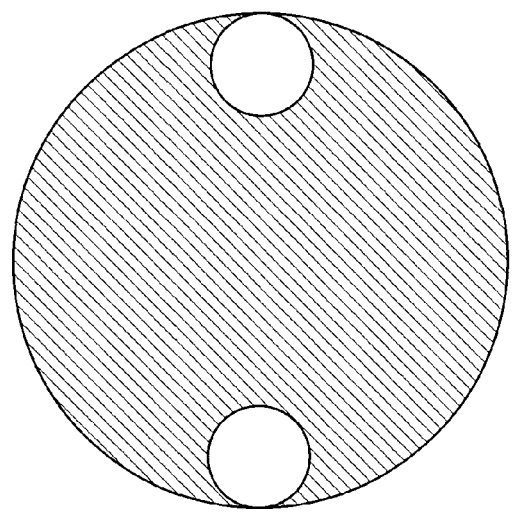
FIG. 21 illustrates an aperture configuration in an exposure tool of dipole illumination for improving the contrast of X-direction lines.
Figure 22:
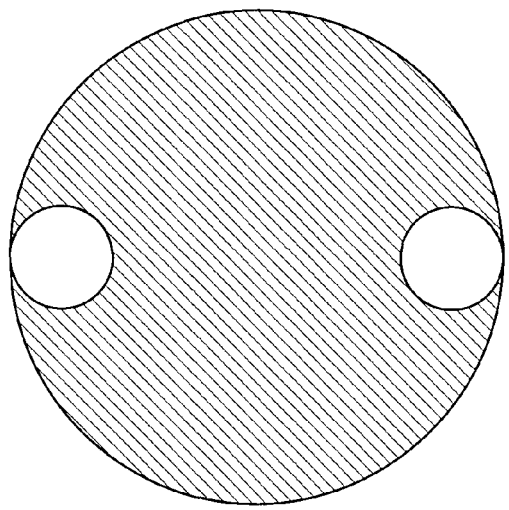
FIG. 22 illustrates an aperture configuration in an exposure tool of dipole illumination for improving the contrast of Y-direction lines.

Exposure by double dipole illuminations of X- and Y-direction lines combined with polarized illumination presents a method of forming light of the highest contrast. This method, however, is not regarded practical because of the drawback that the throughput is substantially reduced by double exposures and mask exchange therebetween. It is then proposed in Non-Patent Document 1 to carry out two exposures by dipole illuminations in X- and Y-directions using a mask having a lattice-like pattern. Specifically, the method of Non-Patent Document 1 involves forming X-direction lines in a first photoresist film by X-direction dipole illumination using a mask having a lattice-like pattern, insolubilizing the X-direction lines by light irradiation, coating a second photoresist film thereon, and forming Y-direction lines by Y-direction dipole illumination, thereby forming holes at the interstices between X- and Y-direction lines. Although only a single mask is needed, this method includes additional steps of insolubilizing the first photoresist pattern between the two exposures, and coating and developing the second photoresist film. Then the wafer must be removed from the exposure stage between the two exposures to give rise to the problem of an increased alignment error. To minimize the alignment error between two exposures, two exposures must be continuously carried out without removing the wafer from the exposure stage. FIG. 21 shows the shape of apertures for dipole illumination for forming X-direction or horizontal lines using a mask having a lattice-like pattern, and FIG. 22 shows the shape of apertures for dipole illumination for forming Y-direction or vertical lines. The addition of s-polarized illumination to dipole illumination provides a further improved contrast and is thus preferably employed. After two exposures for forming X- and Y-direction lines using a lattice-like mask are performed in an overlapping manner, negative tone development is performed whereupon a hole pattern is formed.

Figure 23:
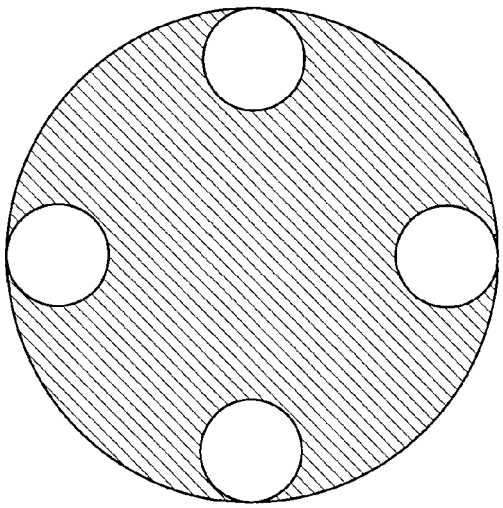
FIG. 23 illustrates an aperture configuration in an exposure tool of cross-pole illumination for improving the contrast of both X and Y-direction lines.

When it is desired to form a hole pattern via a single exposure using a lattice-like mask, a quadra-pole illumination or cross-pole illumination in the aperture configuration shown in FIG. 23 is used. The contrast may be improved by combining it with X-Y polarized illumination or azimuthally polarized illumination of circular polarization.

In the hole pattern forming process of the invention, when two exposures are involved, continuous exposures are carried out by changing the illumination for the second exposure from that for the first exposure, whereby the alignment error is minimized. Of course, a single exposure can make an alignment error smaller than two continuous exposures.

Figure 5:
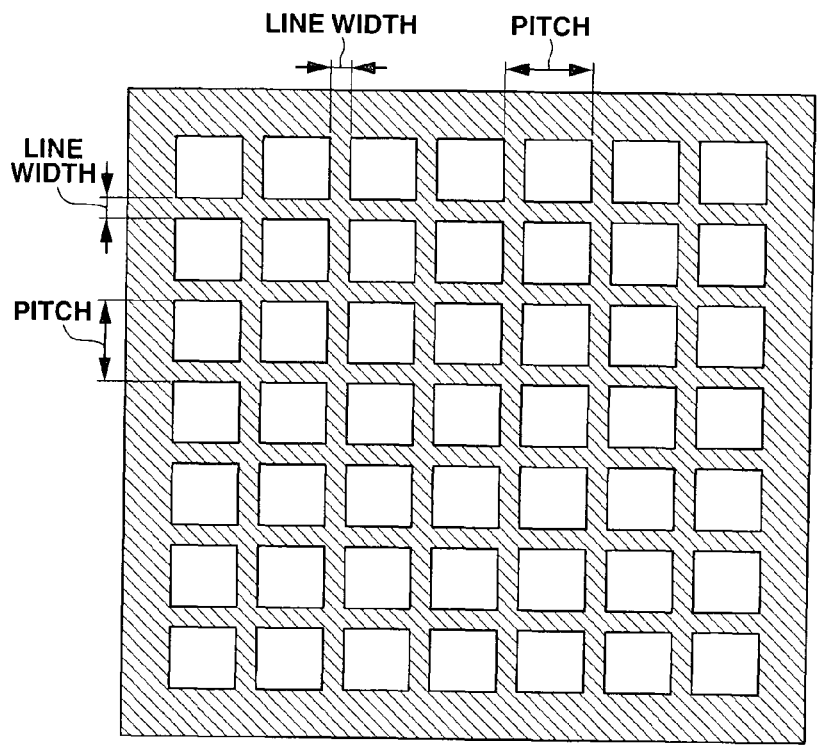
FIG. 5 illustrates a mask bearing a lattice-like pattern.
Figure 7:
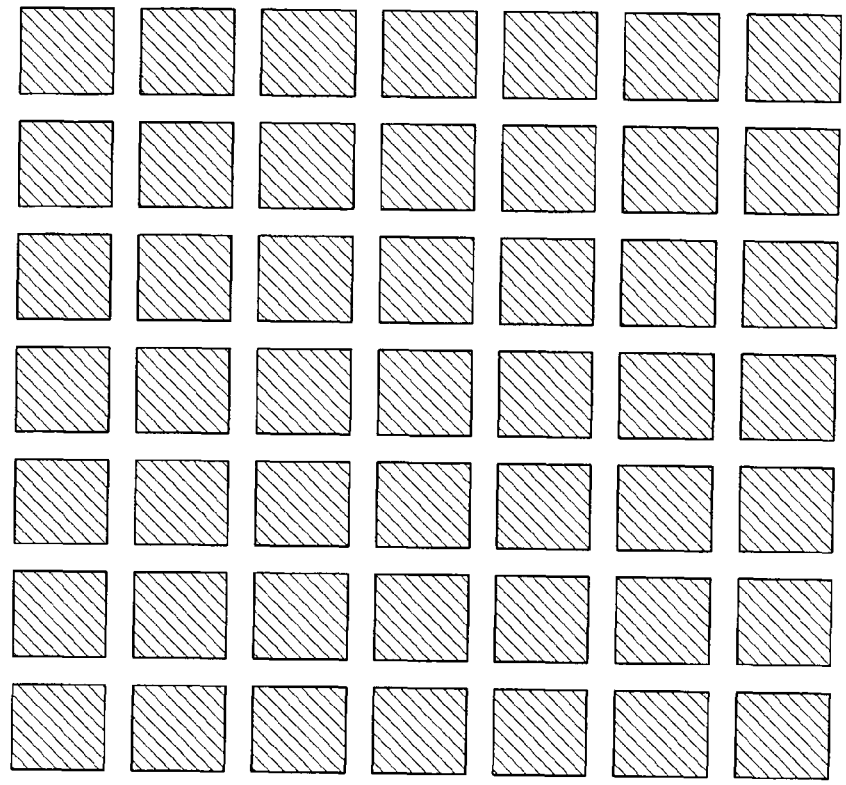
FIG. 7 illustrates a mask bearing a dot pattern of square dots having a pitch of 90 nm and a side width of 60 nm under conditions: NA 1.3 lens, cross-pole illumination, 6% halftone phase shift mask, and azimuthally polarized illumination.
Figure 11:
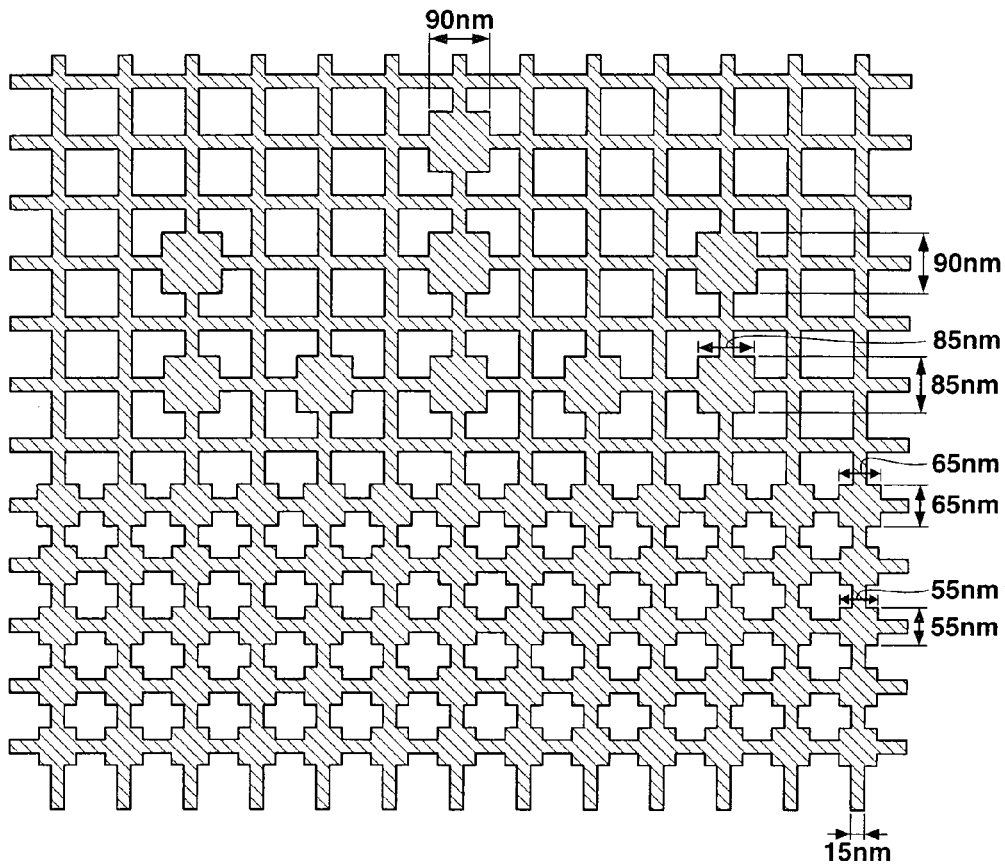
FIG. 11 illustrates a mask bearing a lattice-like pattern having a pitch of 90 nm and a line width of 15 nm on which thick dots are disposed where dots are to be formed.

The mask pattern used herein may be a lattice-like pattern as shown in FIG. 5, a dot pattern as shown in FIG. 7, or a combination of a dot pattern and a lattice-like pattern as shown in FIG. 11. The use of a lattice-like pattern contributes to the most improved light contrast, but has the drawback of a reduced resist sensitivity due to a lowering of light intensity. On the other hand, the use of a dot pattern suffers a lowering of light contrast, but provides the merit of an improved resist sensitivity.

Where holes are arrayed in horizontal and vertical directions, the above-described illumination and mask pattern are used. Where holes are arrayed at a different angle, for example, at an angle of 45°, a mask of a 45° arrayed pattern is combined with dipole illumination or cross-pole illumination.

Where two exposures are performed, a first exposure by a combination of dipole illumination with polarized illumination for enhancing the contrast of X-direction lines is followed by a second exposure by a combination of dipole illumination with polarized illumination for enhancing the contrast of Y-direction lines. Two continuous exposures with the X- and Y-direction contrasts emphasized through a single mask can be performed on a currently commercially available scanner.

The method of combining X and Y polarized illuminations with cross-pole illumination using a mask having a lattice-like pattern can form a hole pattern through a single exposure, despite a slight lowering of light contrast as compared with two exposures of dipole illumination. The method is estimated to attain a substantial improvement in throughput and avoids the problem of misalignment between two exposures. Using such a mask and illumination, a hole pattern of the order of 40 nm can be formed at a practically acceptable cost.

Figure 6:
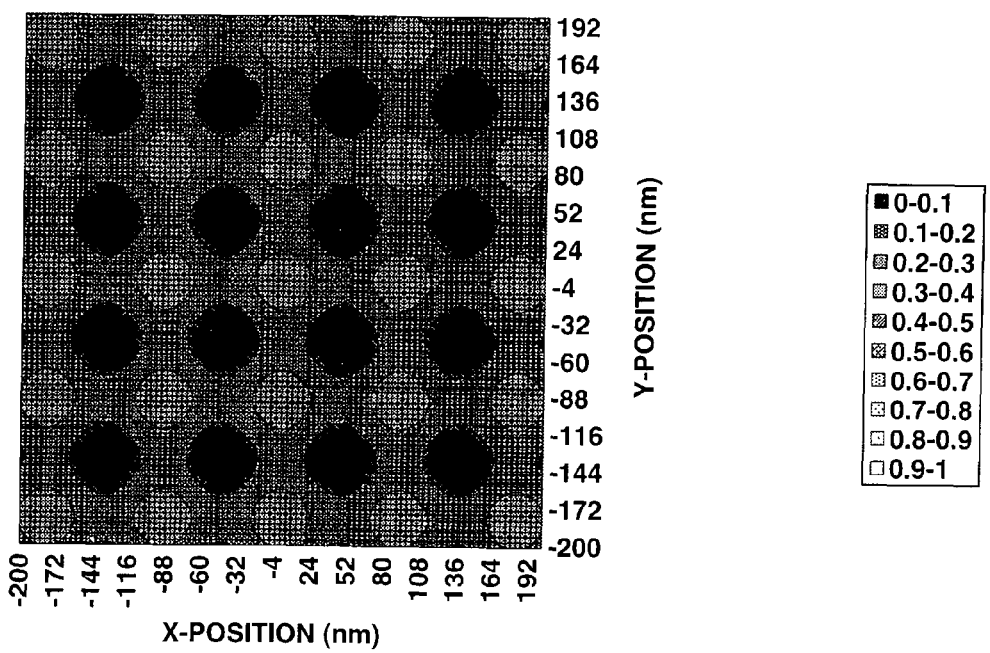
FIG. 6 is an optical image of a lattice-like pattern having a pitch of 90 nm and a line width of 30 nm printed under conditions: NA 1.3 lens, cross-pole illumination, 6% halftone phase shift mask, and azimuthally polarized illumination.

On use of a mask bearing a lattice-like pattern as shown in FIG. 5 where light is fully shielded at intersections between gratings, black spots having a very high degree of light shielding appear as shown in FIG. 6. FIG. 6 is an optical image of a lattice-like line pattern having a pitch of 90 nm and a line width of 30 nm printed under conditions: NA 1.3 lens, cross-pole illumination, 6% halftone phase shift mask, and azimuthally polarized illumination. A fine hole pattern may be formed by performing exposure through a mask bearing such a pattern and organic solvent development entailing positive/negative reversal.

Figure 8:
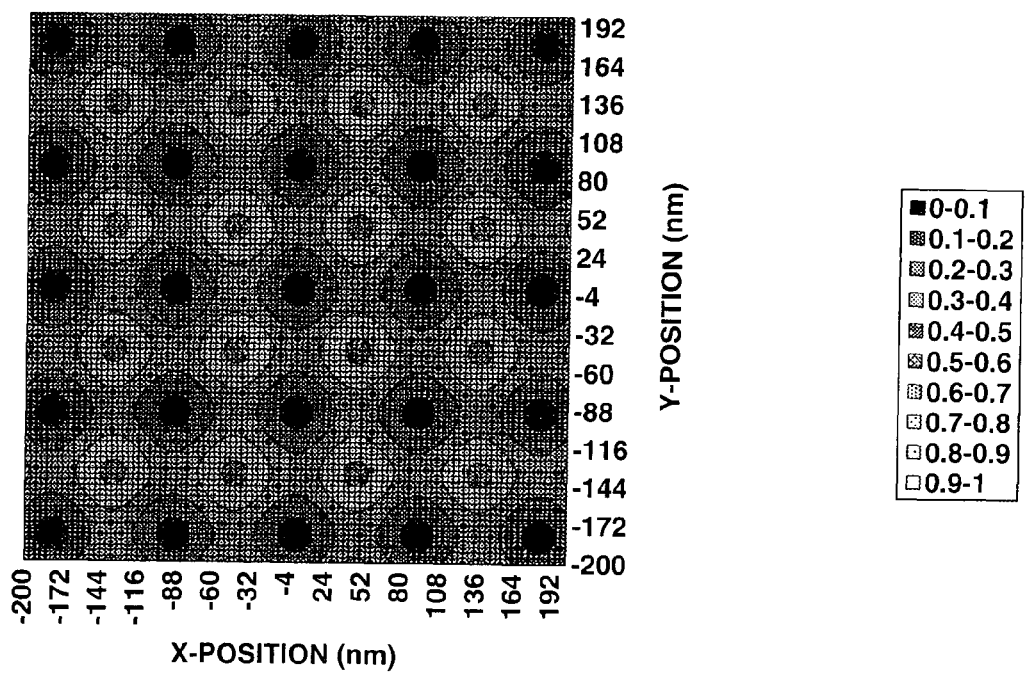
FIG. 8 is an optical image resulting from the mask of FIG. 7, showing its contrast.

On use of a mask bearing a dot pattern of square dots having a pitch of 90 nm and a side width of 60 nm as shown in FIG. 7, under conditions: NA 1.3 lens, cross-pole illumination, 6% halftone phase shift mask, and azimuthally polarized illumination, an optical image is obtained as shown in FIG. 8 that depicts the contrast thereof. Although the circle of fully light shielded spot in FIG. 8 has a smaller area than in FIG. 6, which indicates a low contrast as compared with the lattice-like pattern mask, the formation of a hole pattern is possible owing to the presence of black or light shielded spots.

It is difficult to form a fine hole pattern that holes are randomly arrayed at varying pitch and position. The super-resolution technology using off-axis illumination (such as dipole or cross-pole illumination) in combination with a phase shift mask and polarization is successful in improving the contrast of dense (or grouped) patterns, but not so the contrast of isolated patterns.

When the super-resolution technology is applied to repeating dense patterns, the pattern density bias between dense and isolated patterns, known as proximity bias, becomes a problem. As the super-resolution technology used becomes stronger, the resolution of a dense pattern is more improved, but the resolution of an isolated pattern remains unchanged. Then the proximity bias is exaggerated. In particular, an increase of proximity bias in a hole pattern resulting from further miniaturization poses a serious problem. One common approach taken to suppress the proximity bias is by biasing the size of a mask pattern. Since the proximity bias varies with properties of a photoresist composition, specifically dissolution contrast and acid diffusion, the proximity bias of a mask varies with the type of photoresist composition. For a particular type of photoresist composition, a mask having a different proximity bias must be used. This adds to the burden of mask manufacturing. Then the pack and unpack (PAU) method is proposed in Proc. SPIE Vol. 5753, p 171 (2005), which involves strong super-resolution illumination of a first positive resist to resolve a dense hole pattern, coating the first positive resist pattern with a negative resist film material in alcohol solvent which does not dissolve the first positive resist pattern, exposure and development of an unnecessary hole portion to close the corresponding holes, thereby forming both a dense pattern and an isolated pattern. One problem of the PAU method is misalignment between first and second exposures, as the authors point out in the report. The hole pattern which is not closed by the second development experiences two developments and thus undergoes a size change, which is another problem.

Figure 9:
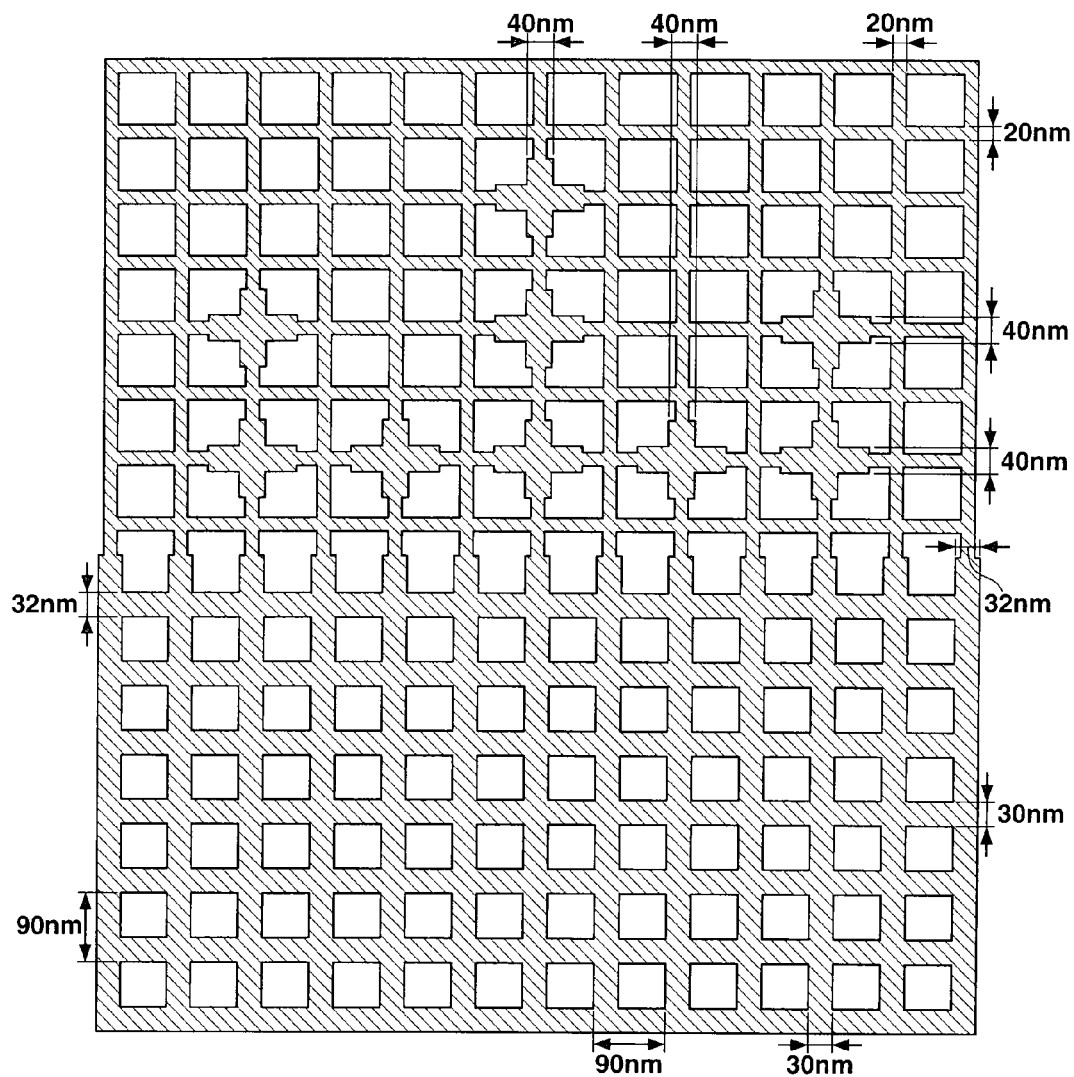
FIG. 9 illustrates a mask bearing a lattice-like pattern having a pitch of 90 nm and a line width of 20 nm on which thick crisscross or intersecting line segments are disposed where dots are to be formed.
Figure 10:
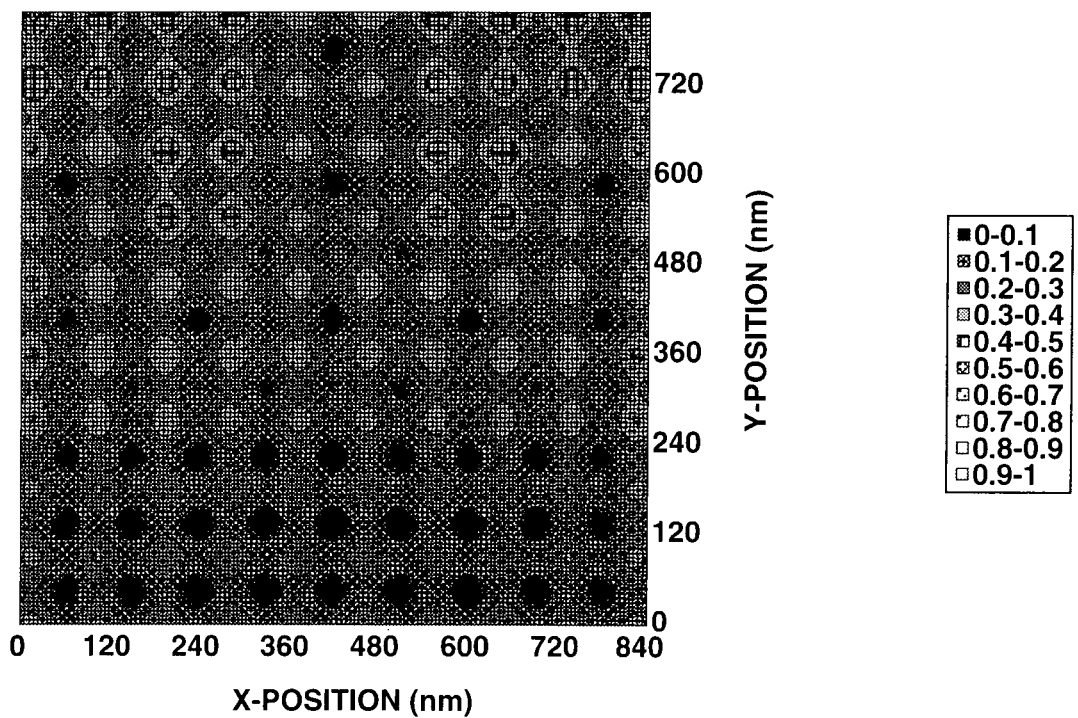
FIG. 10 is an optical image resulting from the mask of FIG. 9, showing its contrast.

To form a random pitch hole pattern by organic solvent development entailing positive/negative reversal, a mask is used in which a lattice-like pattern is arrayed over the entire surface and the width of gratings is thickened only where holes are to be formed. As shown in FIG. 9, on a lattice-like pattern having a pitch of 90 nm and a line width of 20 nm, thick crisscross or intersecting line segments are disposed where dots are to be formed. A black area corresponds to the halftone shifter portion. Line segments with a width of 30 nm are disposed in the dense pattern portion whereas thicker line segments (width 40 nm in FIG. 9) are disposed in more isolated pattern portions. Since the isolated pattern provides light with a lower intensity than the dense pattern, thicker line segments are used. Since the peripheral area of the dense pattern provides light with a relatively low intensity, line segments having a width of 32 nm are assigned to the peripheral area which width is slightly greater than that in the internal area of the dense pattern. FIG. 10 shows an optical image from the mask of FIG. 9, indicating the contrast thereof. Black or light shielded areas are where holes are formed via positive/negative reversal. Black spots are found at positions other than where holes are formed, but few are transferred in practice because they are of small size. Optimization such as reduction of the width of grating lines corresponding to unnecessary holes can inhibit transfer of unnecessary holes.

Also useful is a mask in which a lattice-like pattern is arrayed over the entire surface and thick dots are disposed only where holes are to be formed. As shown in FIG. 11, on a lattice-like pattern having a pitch of 90 nm and a line width of 15 nm, thick dots are disposed where dots are to be formed. A black area corresponds to the halftone shifter portion. Square dots having one side with a size of 55 nm are disposed in the dense pattern portion whereas larger square dots (side size 90 nm in FIG. 11) are disposed in more isolated pattern portions. Although square dots are shown in the figure, the dots may have any shape including rectangular, rhombic, pentagonal, hexagonal, heptagonal, octagonal, and polygonal shapes and even circular shape.

Figure 12:
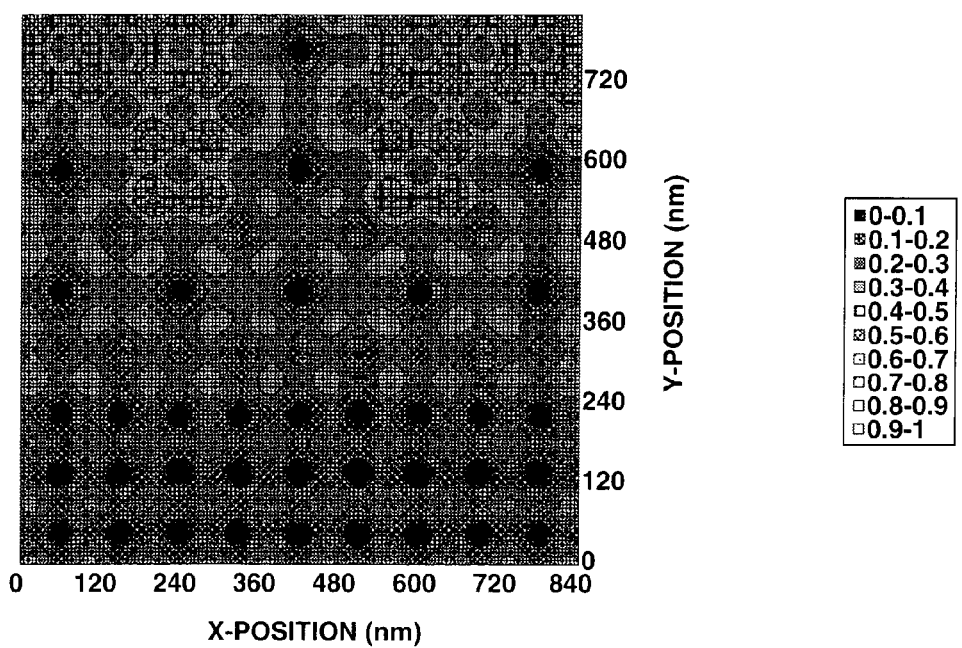
FIG. 12 is an optical image resulting from the mask of FIG. 11, showing its contrast.

FIG. 12 shows an optical image from the mask of FIG. 11, indicating the contrast thereof. The presence of black or light shielded spots substantially equivalent to those of FIG. 10 indicates that holes are formed via positive/negative reversal.

Figure 13:
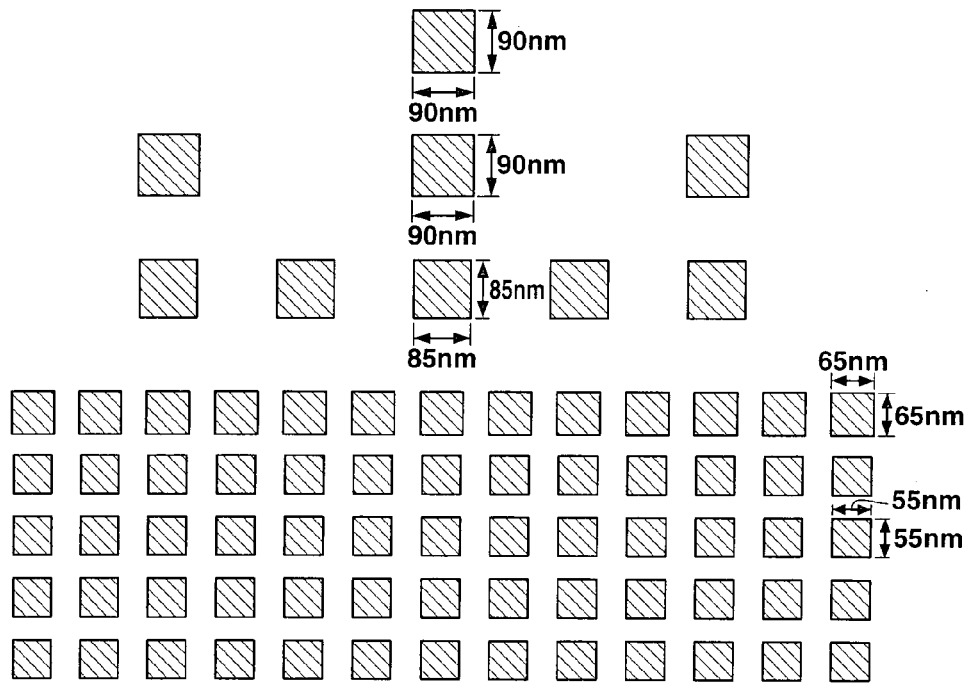
FIG. 13 illustrates a mask without a lattice-like pattern.
Figure 14:
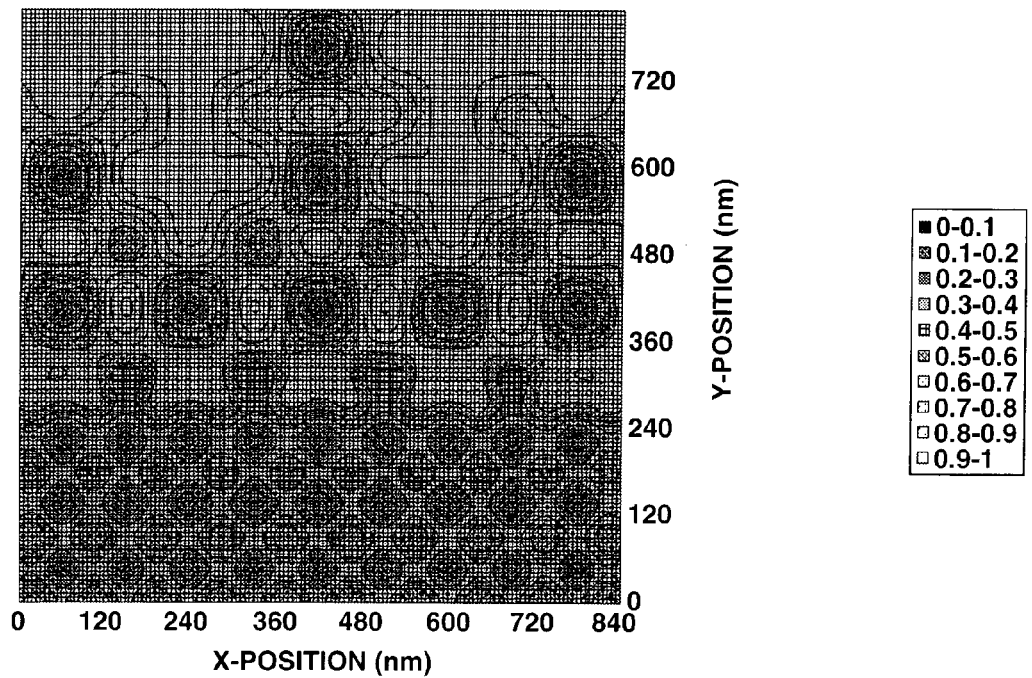
FIG. 14 is an optical image resulting from the mask of FIG. 13, showing its contrast.

On use of a mask bearing no lattice-like pattern arrayed as shown in FIG. 13, black or light shielded spots do not appear as shown in FIG. 14. In this case, holes are difficult to form, or even if holes are formed, a variation of mask size is largely reflected by a variation of hole size because the optical image has a low contrast.

EXAMPLE

Examples of the invention are given below by way of illustration and not by way of limitation. The abbreviation "pbw" is parts by weight. Me stands for methyl, Et for ethyl, and t-Bu for tertiary butyl. For all polymers, Mw and Mn are determined by GPC versus polystyrene standards. For pattern profile observation, a top-down scanning electron microscope (TDSEM) S-9380 (Hitachi Hitechnologies, Ltd.) was used.

Synthesis Example 1

Acetal compounds within the scope of the invention were synthesized in accordance with the formulation shown below.

Synthesis Example 1-1

Synthesis of Monomer 1

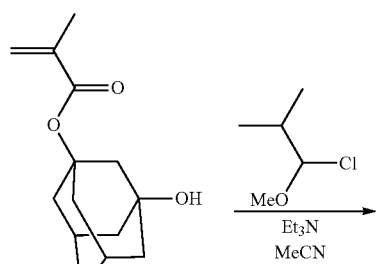

Starting Monomer 1

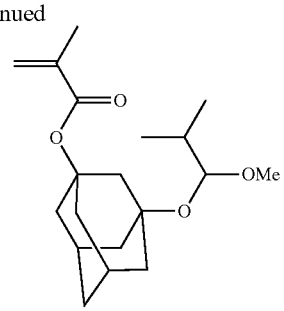

Monomer 1

In 200 ml of acetonitrile, 50.0 g of Starting Monomer 1 was mixed with 34.3 g of triethylamine and 0.05 g of 2,2'-methylenebis(6-t-butyl-p-cresol). To the mixture below 20° C., 36.3 g of methyl 1-chloro-2-methylpropyl ether was added dropwise, followed by stirring at room temperature for 4 hours. 300 ml of water was added to quench the reaction, followed by standard workup. Purification by distillation gave 62.2 g (yield 91%) of the end compound.

Boiling point: 110-111° C./15 Pa $^1$H-NMR (600 MHz in DMSO-$d_6$): δ=0.80 (6H, dd), 1.48 (2H, s), 1.64-1.75 (4H, m), 1.77 (1H, sept), 1.81 (3H, s), 1.94-2.04 (4H, m), 2.09 (2H, app dt), 2.26 (2H, t), 3.10 (3H, s), 4.42 (1H, d), 5.59 (1H, m), 5.92 (1H, s) ppm

Synthesis Example 1-2

Synthesis of Monomer 2

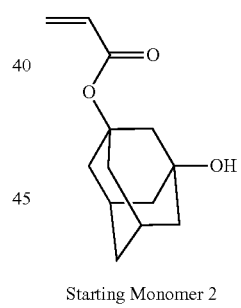 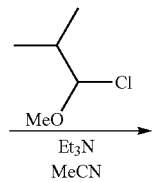

Starting Monomer 2

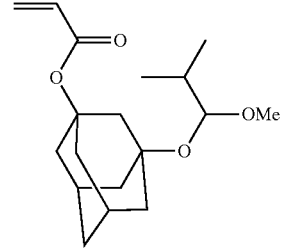

Monomer 2

Monomer 2 was prepared by the same procedure as Synthesis Example 1-1 except that Starting Monomer 2 was used instead of Starting Monomer 1. Yield 89%.

Synthesis Example 1-3

Synthesis of Monomer 3

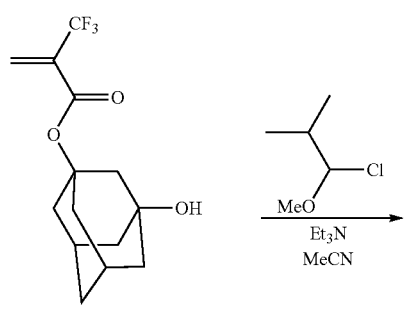

Starting Monomer 3

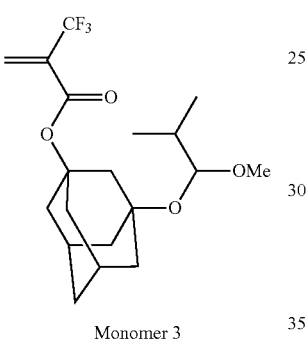

Monomer 3

Monomer 3 was prepared by the same procedure as Synthesis Example 1-1 except that Starting Monomer 3 was used instead of Starting Monomer 1. Yield 89%.

Synthesis Example 1-4

Synthesis of Monomer 4

Monomer 4 was prepared by the same procedure as Synthesis Example 1-1 except that neopentyl 1-chloro-2-methylpropyl ether was used instead of methyl 1-chloro-2-methylpropyl ether. Yield 90%.

Synthesis Example 1-5

Synthesis of Monomer 5

Monomer 5 was prepared by the same procedure as Synthesis Example 1-1 except that 2-tricyclodecanyl 1-chloro-2-methylpropyl ether was used instead of methyl 1-chloro-2-methylpropyl ether. Yield 82%.

Synthesis Example 1-6

Synthesis of Monomer 6

Monomer 6 was prepared by the same procedure as Synthesis Example 1-1 except that (1-adamantyl)methyl 1-chloro-2-methylpropyl ether was used instead of methyl 1-chloro-2-methylpropyl ether. Yield 84%.

Synthesis Example 1-7

Synthesis of Monomer 7

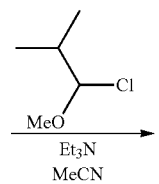

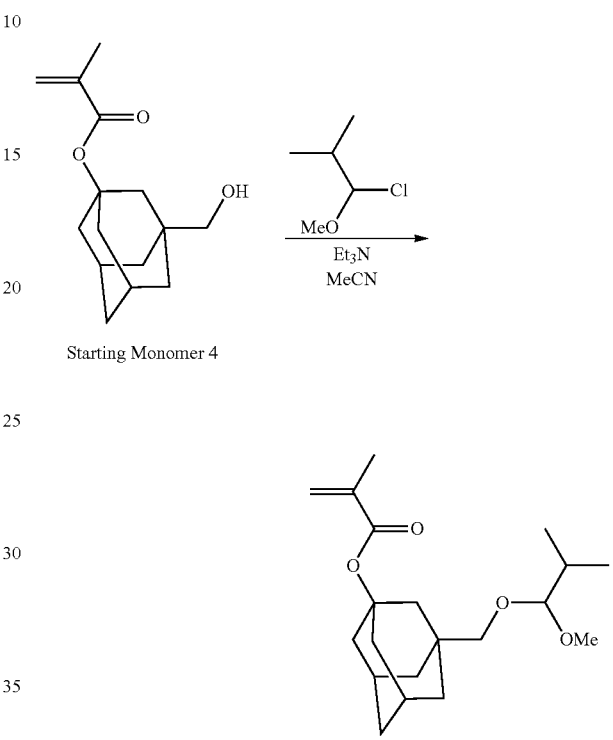

Starting Monomer 4

Monomer 7

Monomer 7 was prepared by the same procedure as Synthesis Example 1-1 except that Starting Monomer 4 was used instead of Starting Monomer 1. Yield 92%.

Synthesis Example 1-8

Synthesis of Monomer 8

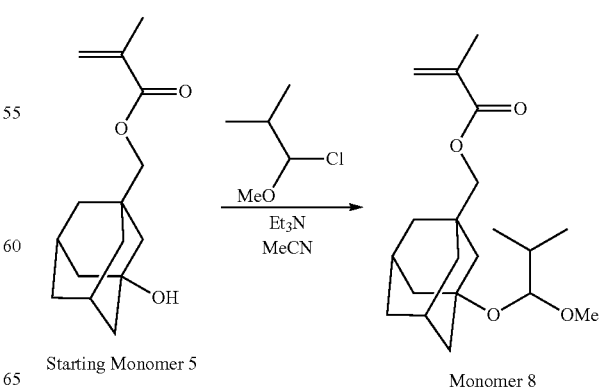

Starting Monomer 5

Monomer 8

Monomer 8 was prepared by the same procedure as Synthesis Example 1-1 except that Starting Monomer 5 was used instead of Starting Monomer 1. Yield 88%.

Synthesis Example 1-9

Synthesis of Monomer 9

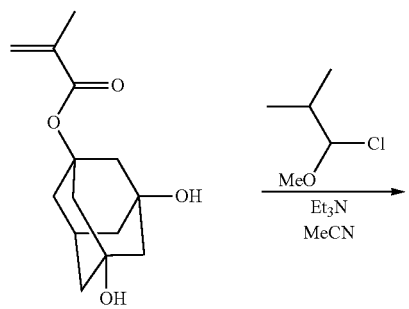

Starting Monomer 6

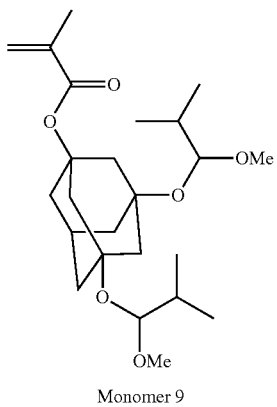

Monomer 9

Monomer 9 was prepared by the same procedure as Synthesis Example 1-1 except that Starting Monomer 6 was used instead of Starting Monomer 1. Yield 93%.

IR (D-ATR): ν=2956, 2932, 2872, 2827, 1716, 1637, 1470, 1455, 1388, 1362, 1331, 1321, 1295, 1250, 1167, 1098, 1039 cm$^{-1}$ $^{1}$H-NMR (600 MHz in DMSO-d$_{6}$): δ=0.80 (12H, dd), 1.56-1.61 (2H, m), 1.62-1.67 (2H, m), 1.71-1.87 (7H, m), 1.93 (2H, s), 2.04-2.12 (4H, m), 2.32 (1H, t), 3.11 (6H, s), 4.44 (2H, d), 5.61 (1H, m), 5.94 (1H, s) ppm

Synthesis Example 1-10

Synthesis of Monomer 10

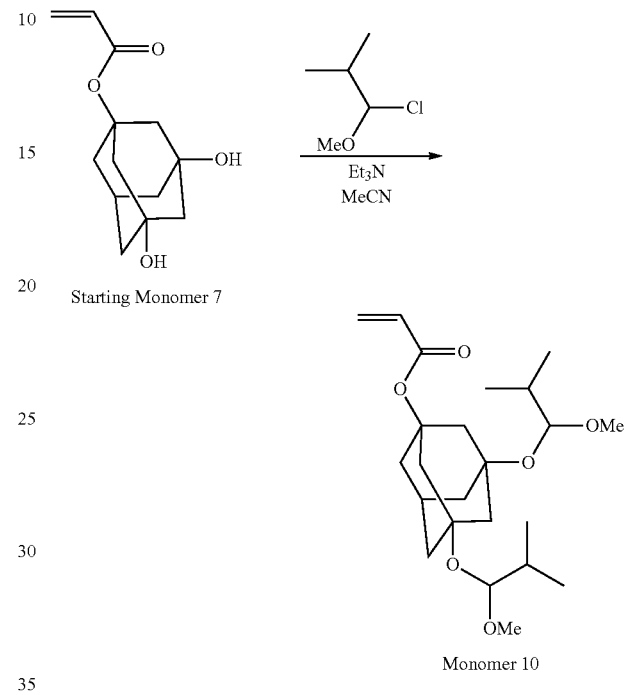

Monomer 10 was prepared by the same procedure as Synthesis Example 1-1 except that Starting Monomer 7 was used instead of Starting Monomer 1. Yield 90%.

Synthesis Example 1-11

Synthesis of Monomer 11

Monomer 11 was prepared by the same procedure as Synthesis Example 1-1 except that Starting Monomer 6 was used instead of Starting Monomer 1 and neopentyl 1-chloro-2-methylpropyl ether was used instead of methyl 1-chloro-2-methylpropyl ether. Yield 86%.

Synthesis Example 1-12

Synthesis of Monomer 12

Monomer 12 was prepared by the same procedure as Synthesis Example 1-1 except that Starting Monomer 6 was used instead of Starting Monomer 1 and 2-tricyclodecanyl 1-chloro-2-methylpropyl ether was used instead of methyl 1-chloro-2-methylpropyl ether. Yield 84%.

Synthesis Example 1-13

Synthesis of Monomer 13

Monomer 13 was prepared by the same procedure as Synthesis Example 1-1 except that Starting Monomer 6 was used instead of Starting Monomer 1 and (1-adamantyl)methyl 1-chloro-2-methylpropyl ether was used instead of methyl 1-chloro-2-methylpropyl ether. Yield 85%.
Monomers 1 to 13 obtained in Synthesis Example 1 have the structural formulae shown below.
Monomer 1
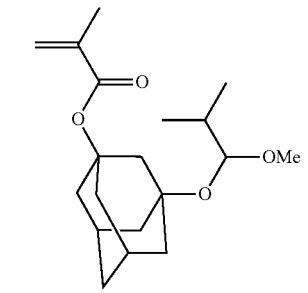
Monomer 2
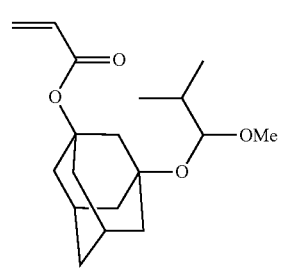
Monomer 3
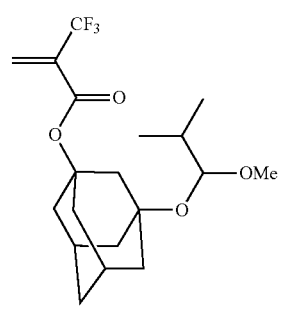
Monomer 4
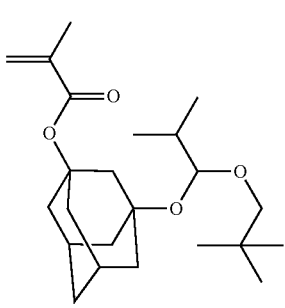
Monomer 5
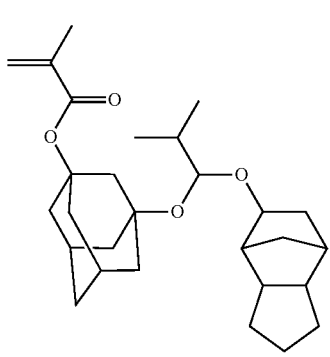
Monomer 6
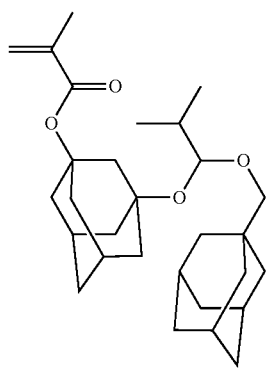
Monomer 7
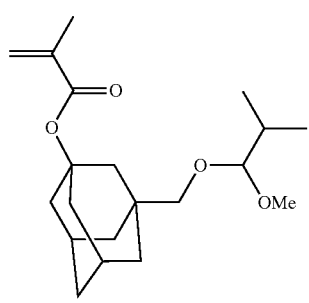
Monomer 8
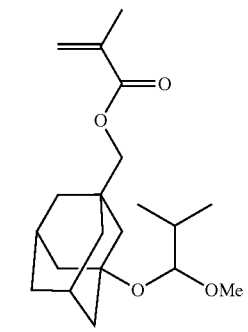
Monomer 9
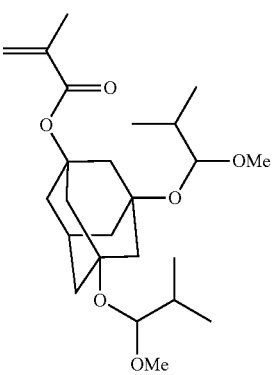

Monomer 10

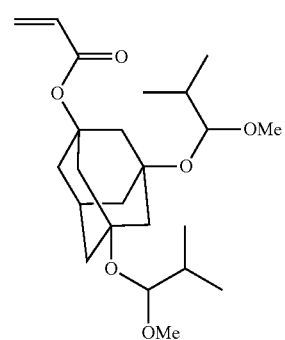

Monomer 11

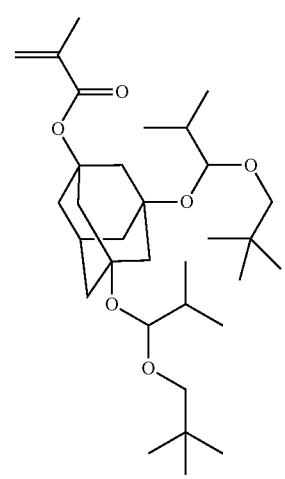

Monomer 12

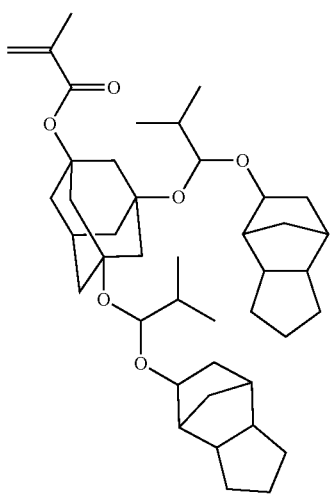

Monomer 13

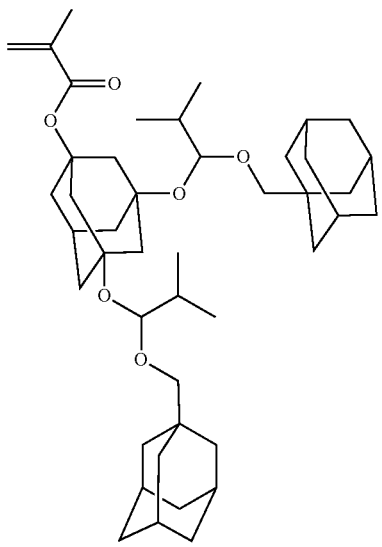

Synthesis Example 2

Polymers within the scope of the invention were synthesized in accordance with the formulation shown below.

Synthesis Example 2-1

Synthesis of Resist Polymer 1

In a nitrogen atmosphere, 23.6 g of Monomer 1, 16.4 g of 4,8-dioxatricyclo[4.2.1.0$^{3,7}$]nonan-5-on-2-yl methacrylate, and 1.69 g of dimethyl 2,2'-azobisisobutyrate were dissolved in 70.0 g of methyl ethyl ketone. With stirring under a nitrogen atmosphere, the solution was added dropwise to 23.3 g of methyl ethyl ketone at 80° C. over 4 hours. After the completion of dropwise addition, the reaction solution was stirred at 80° C. for 2 hours and cooled to room temperature. The polymerization solution was added dropwise to 400 g of n-hexane. The thus precipitated solids were filtered and dried in vacuum at 50° C. for 16 hours, obtaining a polymer in white powder solid form, designated Resist Polymer 1. The amount was 45.5 g, and the yield was 91%.

Resist Polymer 1

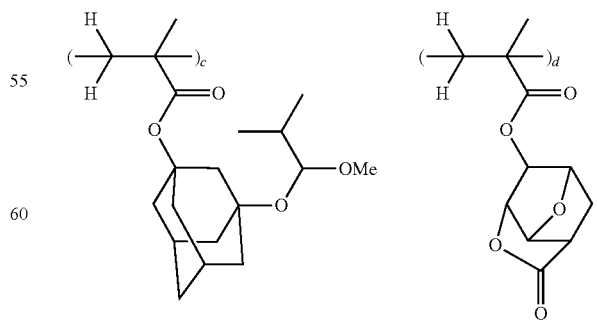

(c = 0.50, d = 0.50, Mw = 6,600)

Synthesis Example 3

Resist Polymers 2 to 15 and Comparative Polymers 1 to 4 were synthesized by the same procedure as Synthesis Example 2-1 except that the type and proportion of monomers were changed. Blend Resist Polymer 1 was synthesized by ring-opening metathesis polymerization. The structure of these polymers is identified below wherein a proportion of units incorporated is in a molar ratio.

Resist Polymer 2

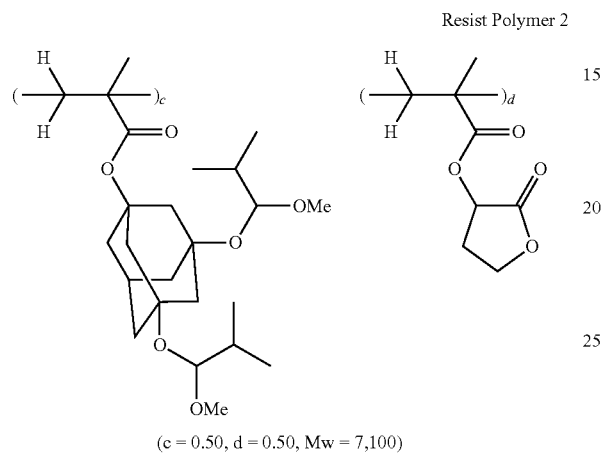

(c = 0.50, d = 0.50, Mw = 7,100)

Resist Polymer 4

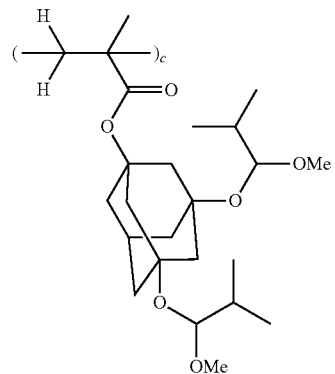

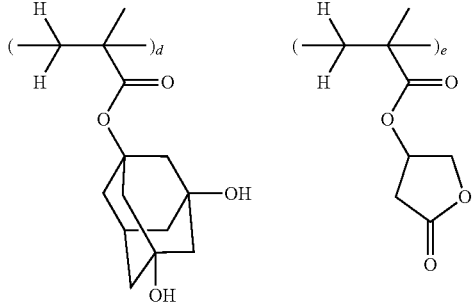

(c = 0.50, d = 0.20, e = 0.30, Mw = 7,500)

Resist Polymer 3

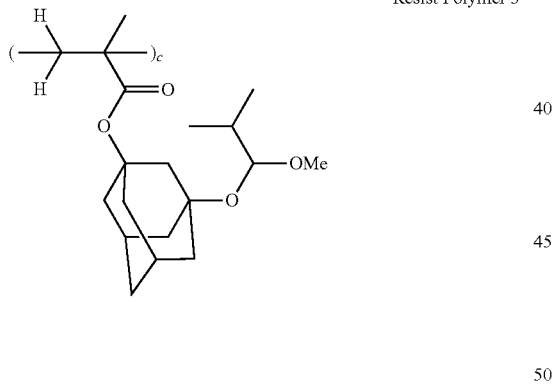

(c = 0.50, d = 0.20, e = 0.30, Mw = 6,900)

Resist Polymer 5

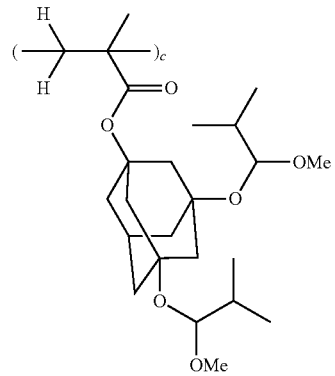

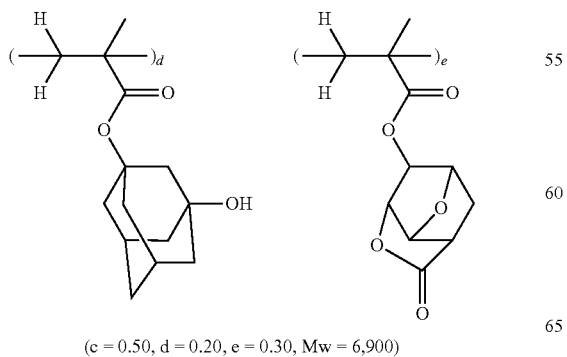

(c = 0.20, d = 0.20, e = 0.60, Mw = 7,100)

101
-continued
Resist Polymer 6
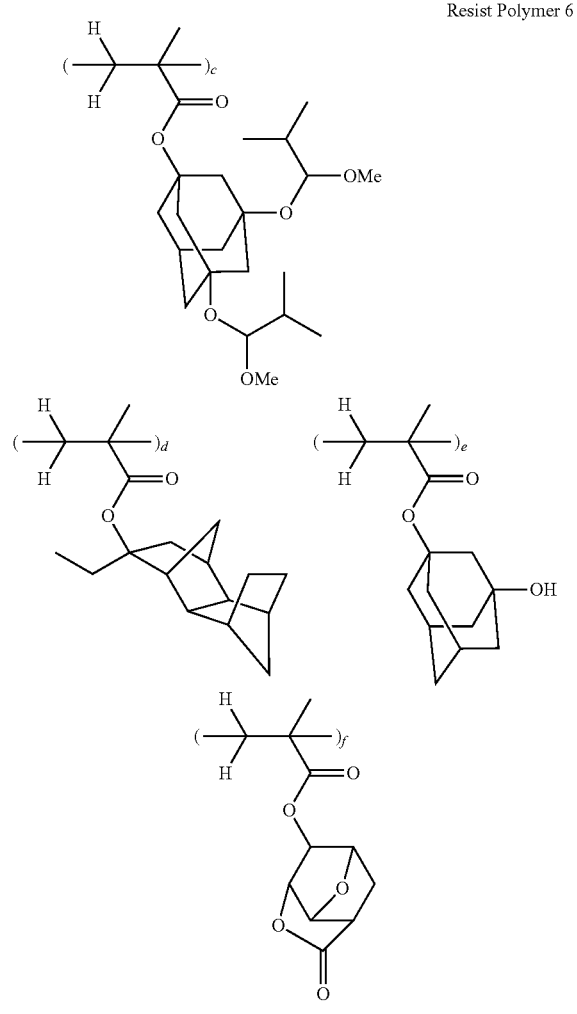
(c = 0.20, d = 0.20, e = 0.20, f = 0.40, Mw = 7,300)
Resist Polymer 7
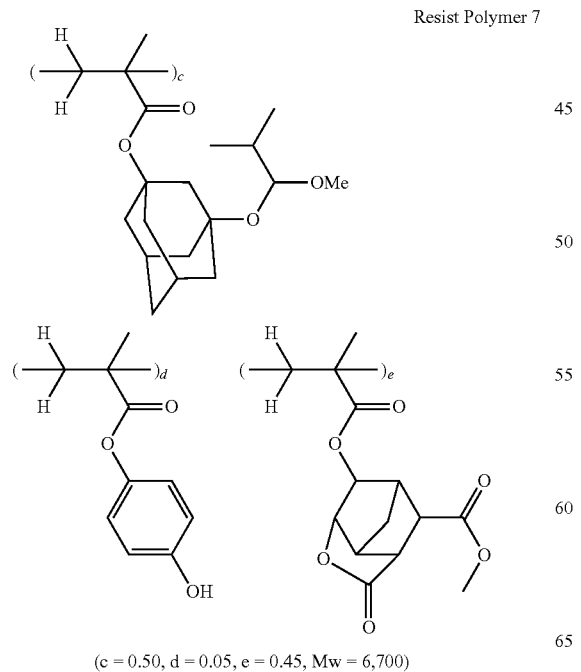
(c = 0.50, d = 0.05, e = 0.45, Mw = 6,700)
102
-continued
Resist Polymer 8
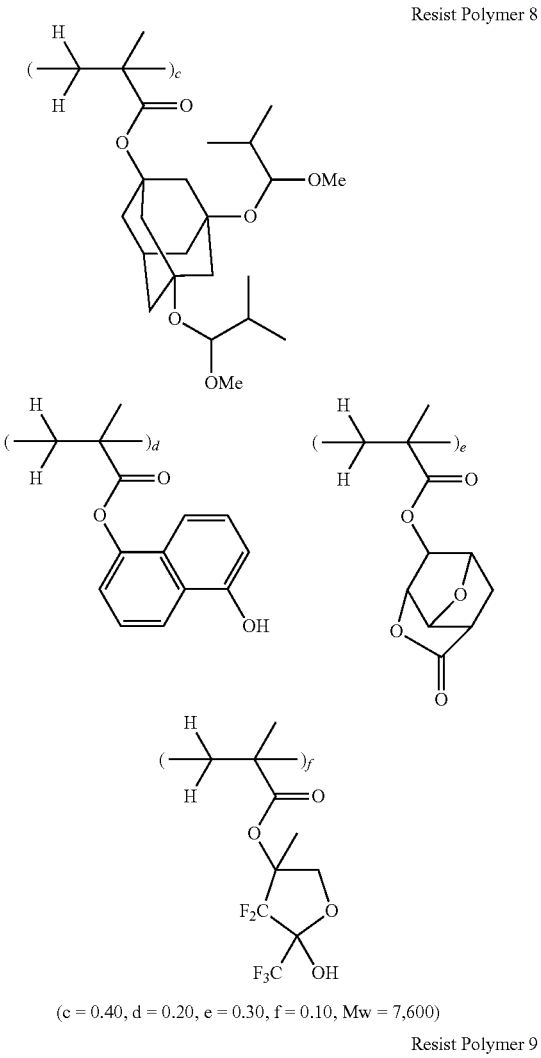
(c = 0.40, d = 0.20, e = 0.30, f = 0.10, Mw = 7,600)
Resist Polymer 9
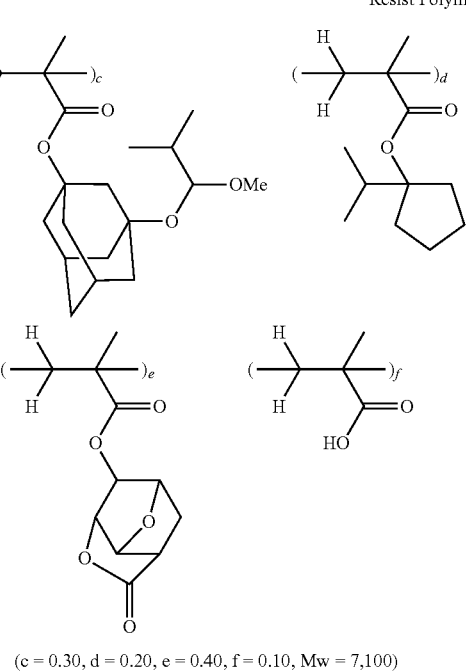
(c = 0.30, d = 0.20, e = 0.40, f = 0.10, Mw = 7,100)

-continued
Resist Polymer 10
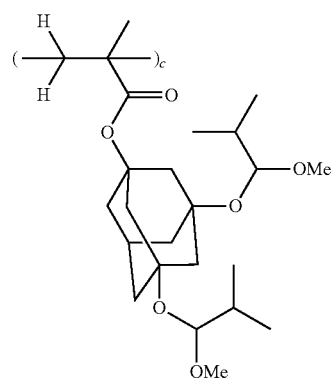
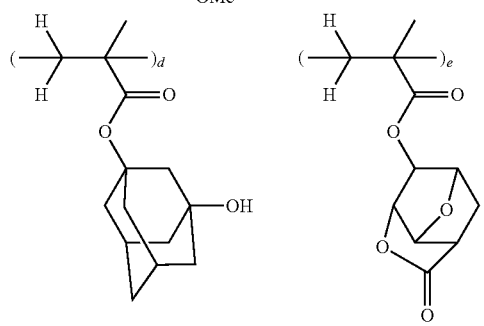
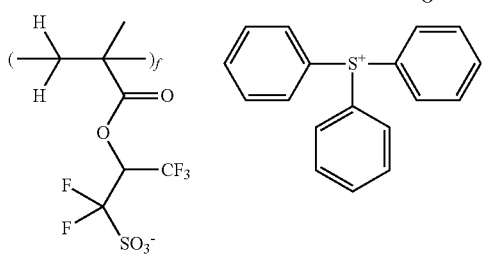
(c = 0.45, d = 0.20, e = 0.30, f = 0.05, Mw = 7,600)
Resist Polymer 11
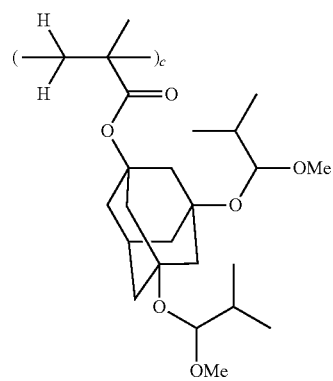
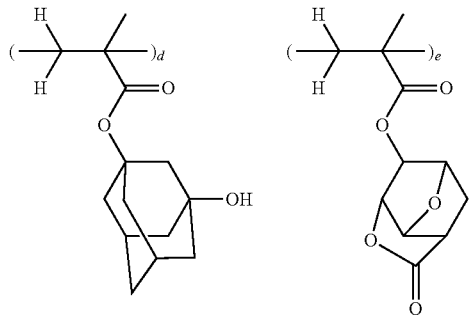
-continued
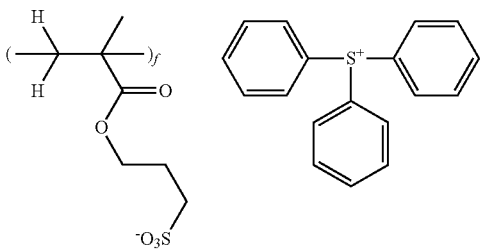
(c = 0.30, d = 0.20, e = 0.45, f = 0.05, Mw = 7,400)
Resist Polymer 12
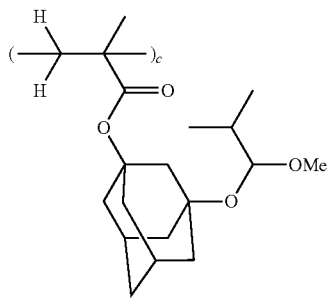
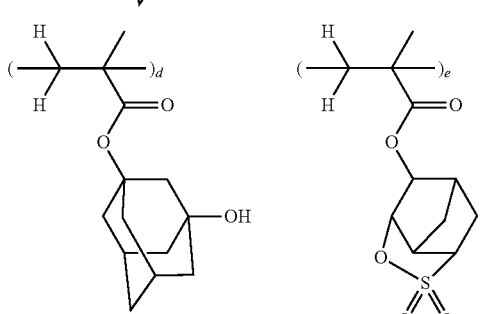
(c = 0.50, d = 0.20, e = 0.30, Mw = 7,800)
Resist Polymer 13
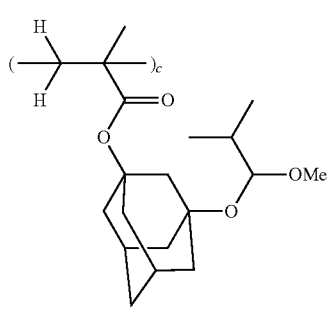
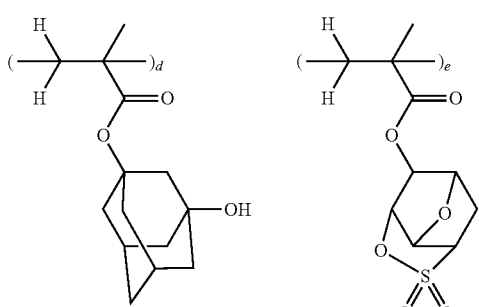
(c = 0.50, d = 0.20, e = 0.30, Mw = 7,800)

Resist Polymer 14
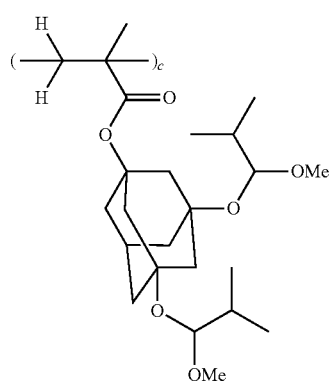
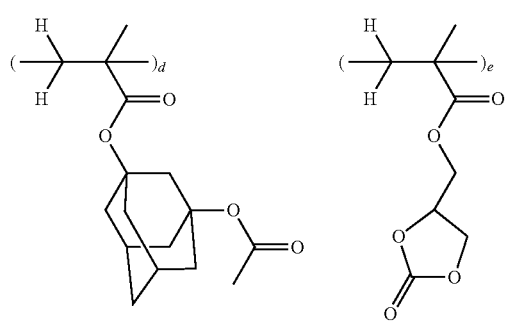
(c = 0.35, d = 0.25, e = 0.40, Mw = 7,300)
Resist Polymer 15
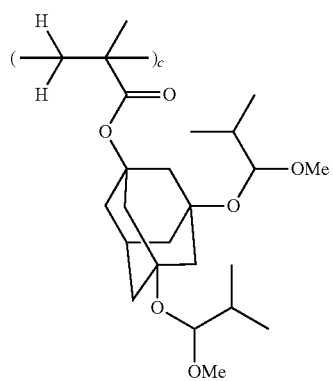
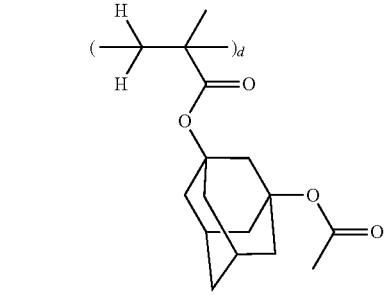
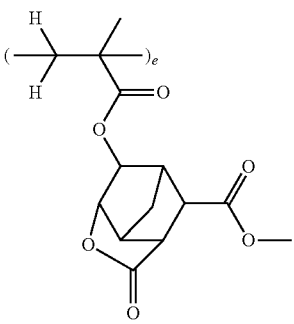
(c = 0.35, d = 0.25, e = 0.40, Mw = 9,800)
Blend Resist Polymer 1
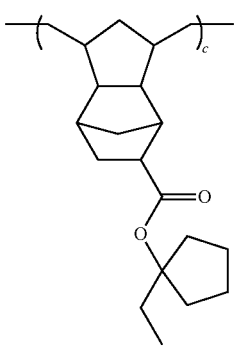
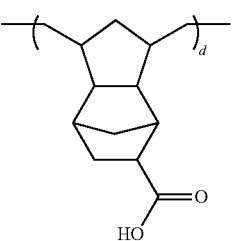
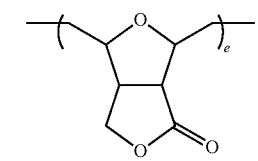
(c = 0.35, d = 0.15, e = 0.50, Mw = 8,800)
Comparative Polymer 1
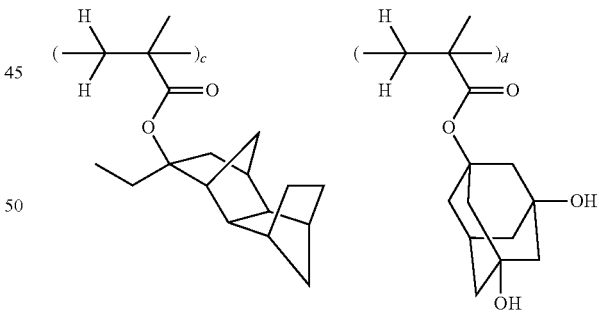
(c = 0.50, d = 0.20, e = 0.30, Mw = 7,000)

-continued

Comparative Polymer 2

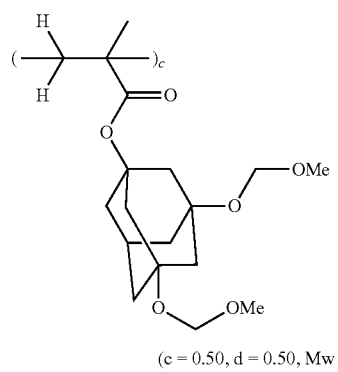

(c = 0.50, d = 0.50, Mw = 7,000)

Comparative Polymer 3

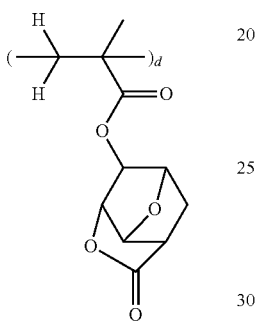

(c = 0.50, d = 0.50, Mw = 5,900)

Comparative Polymer 4

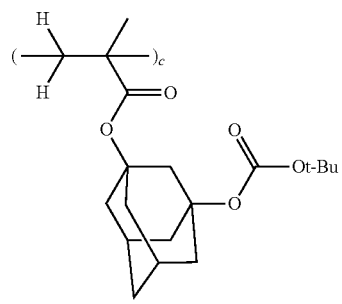

(c = 0.50, d = 0.50, Mw = 6,500)

EXAMPLES AND COMPARATIVE EXAMPLES

Preparation of Positive Resist Composition and Alkali-Soluble Protective Film-Forming Composition A resist composition in solution form was prepared by dissolving polymers (Resist Polymer) and components in solvents in accordance with the formulation of Tables 2 and 3. A protective film-forming composition in solution form was prepared by dissolving polymers (TC Polymer) and components in solvents in accordance with the formulation of Table 4. The solutions were filtered through a Teflon® filter with a pore size of 0.2 μm. The components are identified below.

Acid generator: PAG1 and PAG2 of the following structural formulae

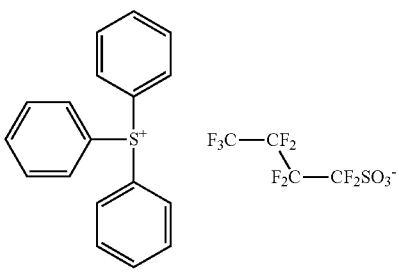

PAG 1

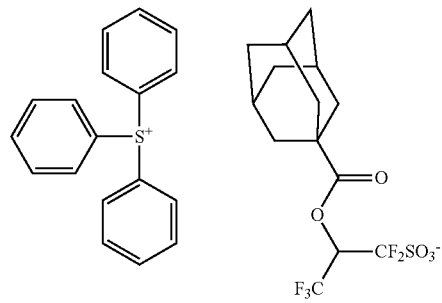

PAG 2

TC Polymer 1

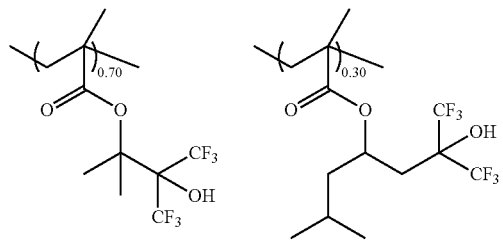

TC Polymer 1

Mw = 8,800
Mw/Mn = 1.69

TC Polymer 2

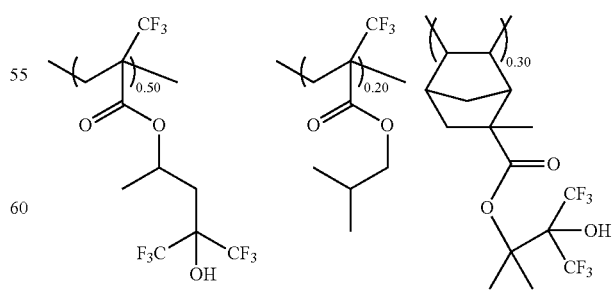

TC Polymer 2

Mw = 7,700
Mw/Mn = 1.77

-continued
TC Polymer 3
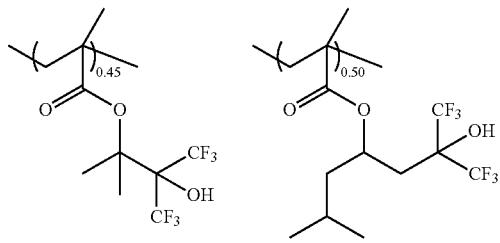
Mw = 9,800
Mw/Mn = 1.98
TC Polymer 4
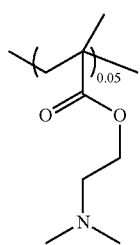
Mw = 8,100
Mw/Mn = 1.81
TC Polymer 5
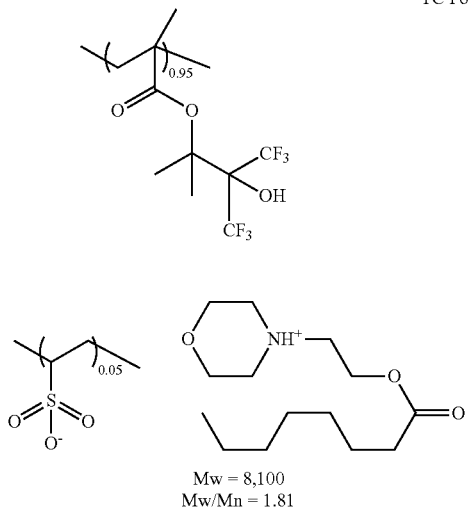
Mw = 9,700
Mw/Mn = 1.77
-continued
TC Polymer 6
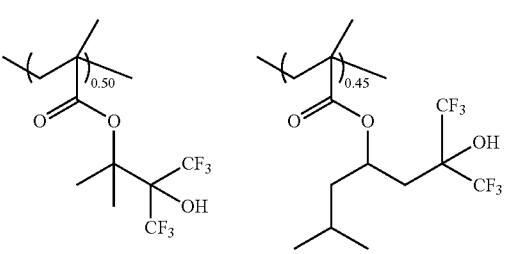
Mw = 9,400
Mw/Mn = 2.04
Water-repellent Polymer 1
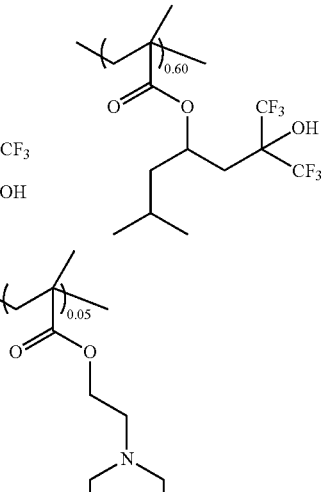
Mw = 8,900
Mw/Mn = 1.96
Water-repellent Polymer 2
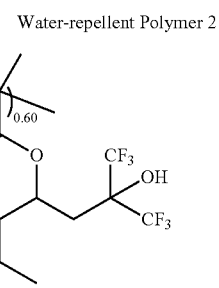

Water-repellent Polymer 3

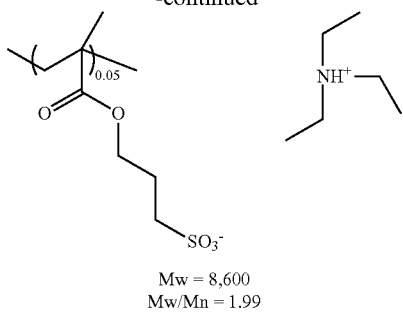

Mw = 8,600
Mw/Mn = 1.99

Water-repellent Polymer 4

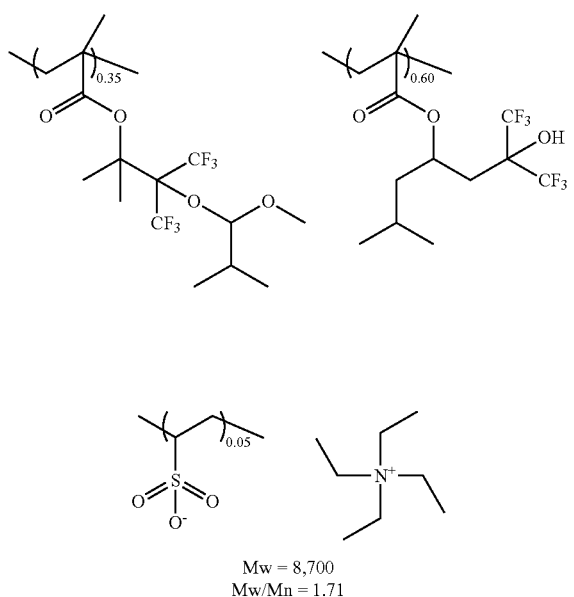

Mw = 8,700
Mw/Mn = 1.71

Water-repellent Polymer 4

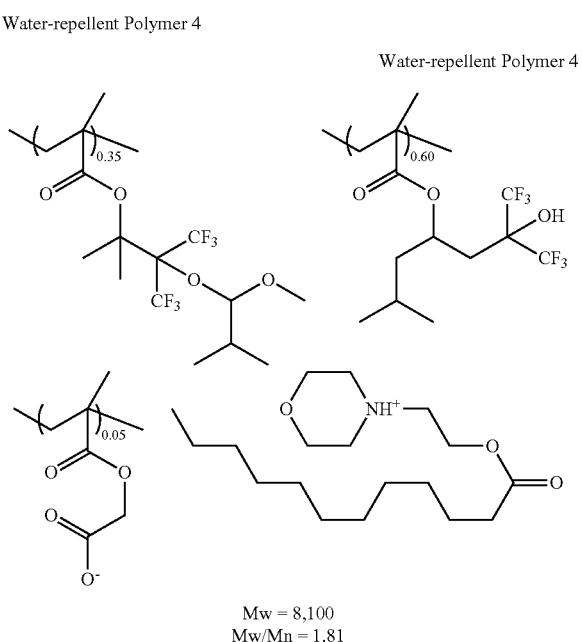

Mw = 8,100
Mw/Mn = 1.81

Water-repellent Polymer 5

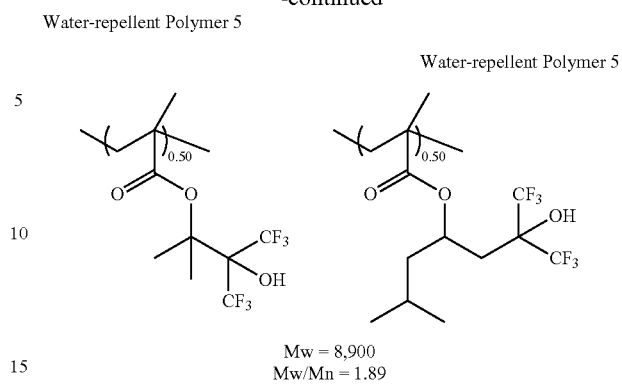

Mw = 8,900
Mw/Mn = 1.89

Basic Compound: Quenchers 1 and 2 of the following structural formulae

Organic Solvent: PGMEA (propylene glycol monomethyl ether acetate)
CyH (cyclohexanone)

ArF Lithography Patterning Test 1

A resist composition was prepared by dissolving polymers (Resist Polymer) and components in solvents in accordance with the formulation of Table 1. On a substrate (silicon wafer) having an antireflective coating (Nissan Chemical Industry Co., Ltd.) of 80 nm thick, the resist composition was spin coated and baked on a hot plate at 100° C. for 60 seconds to form a resist film of 160 nm thick.

Figure 15:
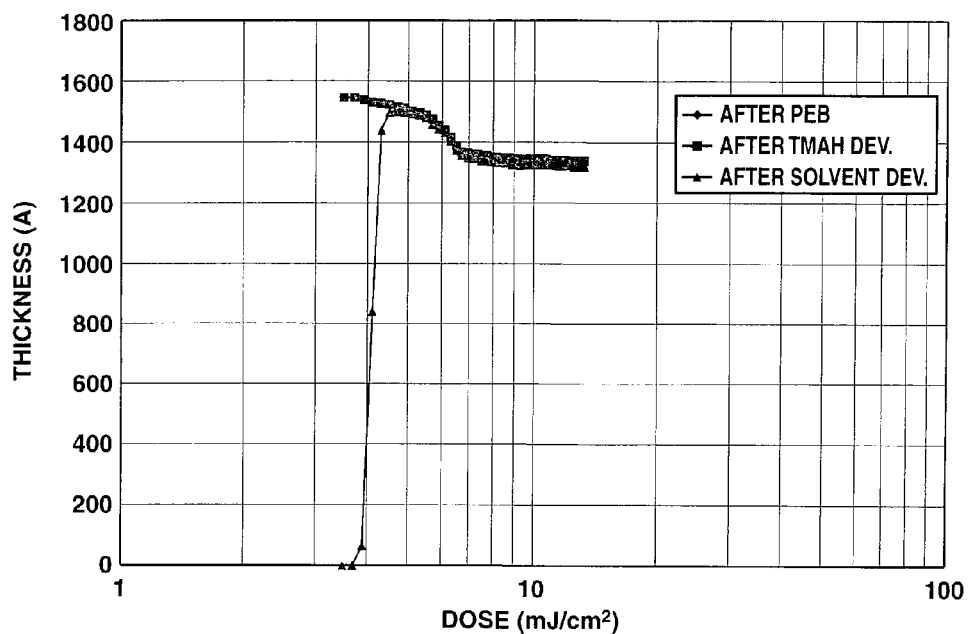
FIG. 15 is a diagram showing film thickness versus exposure dose in Example 1-1.
Figure 16:
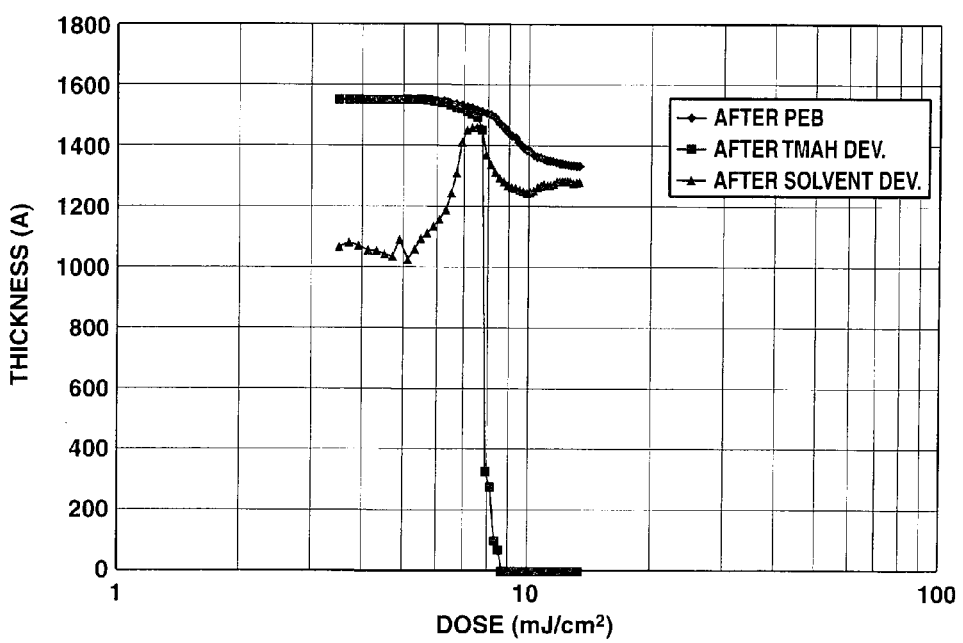
FIG. 16 is a diagram showing film thickness versus exposure dose in Comparative Example 1-1.
Figure 17:
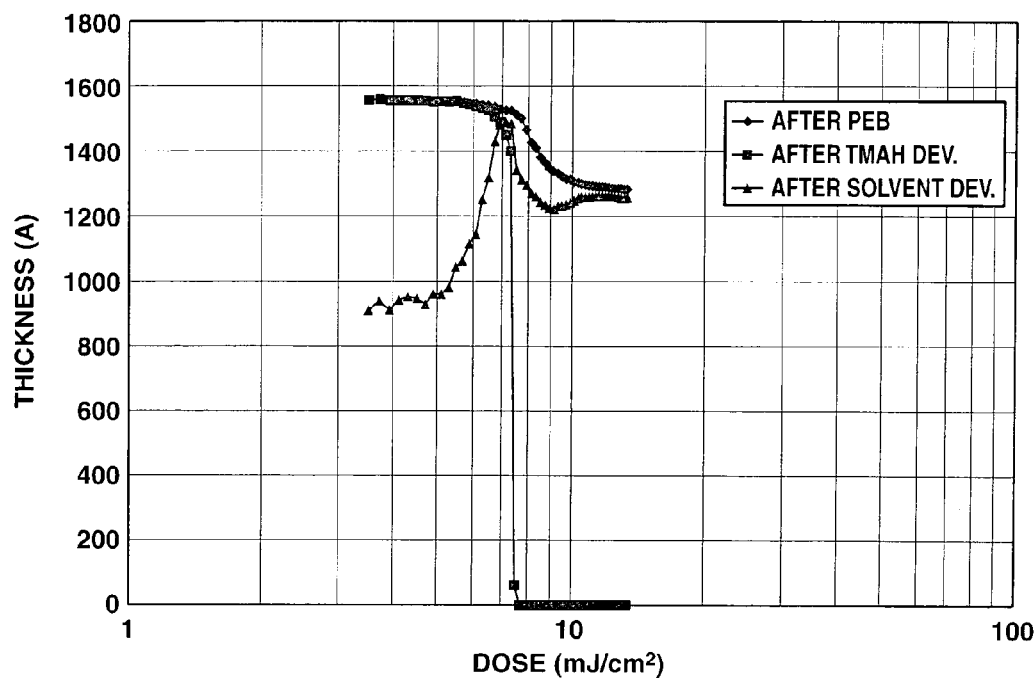
FIG. 17 is a diagram showing film thickness versus exposure dose in Comparative Example 1-2.

Using an ArF excimer laser scanner NSR-305B (Nikon Corp., NA 0.68, σ 0.73), the resist film was open-frame exposed in a dose which varied stepwise by 0.2 mJ/cm². The exposed resist film was baked (PEB) at 110° C. for 60 seconds and puddle developed for 60 seconds with an organic solvent developer as shown in Table 1. The wafer was rinsed at 500 rpm with a rinse liquid (organic solvent) as shown in Table 1, spin dried at 2,000 rpm, and baked at 100° C. for 60 seconds to evaporate off the rinse liquid. Separately, the same process was repeated until the PEB, and followed by development with a 2.38 wt % tetramethylammonium hydroxide (TMAH) aqueous solution. The film thickness after PEB, the film thickness after organic solvent development (butyl acetate BA), and the film thickness after TMAH aqueous solution development were measured. A contrast curve was determined by plotting the film thickness versus the exposure dose. The results are shown in FIGS. 15 to 17.

TABLE 1

|  |  | Polymer (pbw) | Acid generator (pbw) | Basic compound (pbw) | Organic solvent (pbw) | Developer | Rinse liquid |
|---|---|---|---|---|---|---|---|
| Example 1-1 | Resist 1-1 | Polymer 6 (100) | PAG 1 (6.5) | Quencher 1 (1.50) | PGMEA (800) CyH (400) | butyl acetate | 4-methyl-2-pentanol |
| Comparative Example 1-1 | Comparative Resist 1-1 | Comparative Polymer 1 (100) | PAG 1 (6.5) | Quencher 1 (1.50) | PGMEA (800) CyH (400) | butyl acetate | 4-methyl-2-pentanol |
| Comparative Example 1-2 | Comparative Resist 1-2 | Comparative Polymer 2 (100) | PAG 1 (6.5) | Quencher 1 (1.50) | PGMEA (800) CyH (400) | butyl acetate | 4-methyl-2-pentanol |

ArF Lithography Patterning Test 2

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A941 having a silicon content of 43 wt % was deposited thereon to a thickness of 35 nm. On this substrate for trilayer process, the resist composition shown in Tables 2 and 3 was spin coated, then baked on a hot plate at 100° C. for 60 seconds to form a resist film of 100 nm thick. The protective film-forming composition shown in Table 4 was spin coated on the resist film and baked at 90° C. for 60 seconds to form a protective film (or topcoat) of 50 nm thick. In Examples 3-16 to 3-27 and Comparative Example 3-4, the protective film was omitted.

Figure 18:
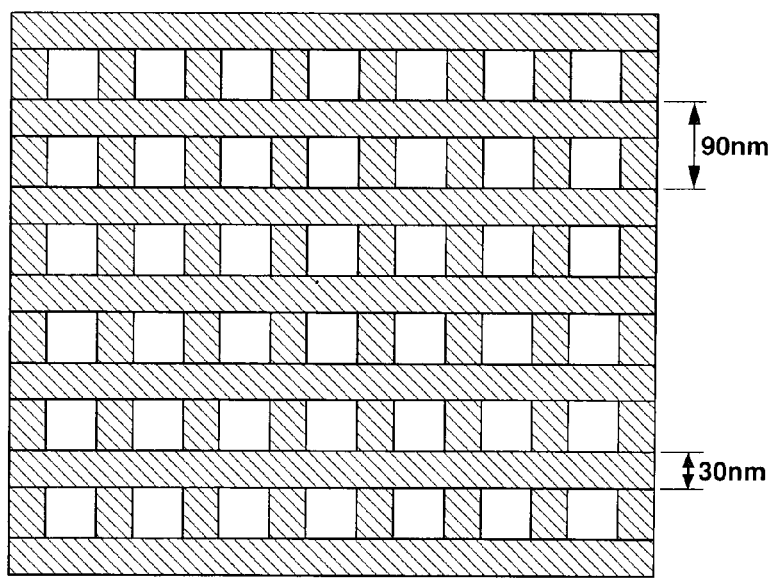
FIG. 18 illustrates a lattice-like mask used in ArF lithography patterning test 2.

Using an ArF excimer laser immersion lithography scanner NSR-610C (Nikon Corp., NA 1.30, σ 0.98/0.78, cross-pole opening 20 deg., azimuthally polarized illumination), exposure was performed in a varying dose through a 6% halftone phase shift mask bearing a lattice-like pattern with a pitch of 90 nm and a line width of 30 nm (on-wafer size) whose layout is shown in FIG. 18. After the exposure, the wafer was baked (PEB) at the temperature shown in Table 5 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of 50 holes was measured, from which a size variation 3σ was determined. The results are shown in Table 5.

TABLE 2

|  |  | Resist | Polymer (pbw) | Acid generator (pbw) | Basic compound (pbw) | Additive (pbw) | Solvent 1 (pbw) | Solvent 2 (pbw) |
|---|---|---|---|---|---|---|---|---|
| Example | 2-1 | R-01 | Resist Polymer 1 (100) | PAG 2 (12.5) | Quencher 1 (1.50) | — | PGMEA (2,000) | CyH (500) |
|  | 2-2 | R-02 | Resist Polymer 2 (100) | PAG 2 (12.5) | Quencher 1 (1.50) | — | PGMEA (2,000) | CyH (500) |
|  | 2-3 | R-03 | Resist Polymer 3 (100) | PAG 2 (12.5) | Quencher 1 (1.50) | — | PGMEA (2,000) | CyH (500) |
|  | 2-4 | R-04 | Resist Polymer 4 (100) | PAG 2 (12.5) | Quencher 1 (1.50) | — | PGMEA (2,000) | CyH (500) |
|  | 2-5 | R-05 | Resist Polymer 5 (100) | PAG 2 (12.5) | Quencher 1 (1.50) | — | PGMEA (2,000) | CyH (500) |
|  | 2-6 | R-06 | Resist Polymer 6 (100) | PAG 2 (12.5) | Quencher 1 (1.50) | — | PGMEA (2,000) | CyH (500) |
|  | 2-7 | R-07 | Resist Polymer 7 (100) | PAG 2 (12.5) | Quencher 1 (1.50) | — | PGMEA (2,000) | CyH (500) |
|  | 2-8 | R-08 | Resist Polymer 8 (100) | PAG 2 (12.5) | Quencher 1 (1.50) | — | PGMEA (2,000) | CyH (500) |
|  | 2-9 | R-09 | Resist Polymer 9 (100) | PAG 2 (12.5) | Quencher 1 (1.50) | — | PGMEA (2,000) | CyH (500) |
|  | 2-10 | R-10 | Resist Polymer 10 (100) | — | Quencher 1 (1.50) | — | PGMEA (2,000) | CyH (500) |
|  | 2-11 | R-11 | Resist Polymer 11 (100) | — | Quencher 1 (1.50) | — | PGMEA (2,000) | CyH (500) |
|  | 2-12 | R-12 | Resist Polymer 6 (100) | PAG 2 (12.5) | Quencher 1 (1.50) | Water-repellent Polymer 1 (6) | PGMEA (2,000) | CyH (500) |
|  | 2-13 | R-13 | Resist Polymer 6 (100) | PAG 2 (12.5) | Quencher 1 (1.50) | Water-repellent Polymer 2 (6) | PGMEA (2,000) | CyH (500) |
|  | 2-14 | R-14 | Resist Polymer 6 (100) | PAG 2 (12.5) | Quencher 1 (1.50) | Water-repellent Polymer 3 (6) | PGMEA (2,000) | CyH (500) |

TABLE 2-continued

| | Resist | Polymer (pbw) | Acid generator (pbw) | Basic compound (pbw) | Additive (pbw) | Solvent 1 (pbw) | Solvent 2 (pbw) |
|---|---|---|---|---|---|---|---|
| 2-15 | R-15 | Resist Polymer 6 (100) | PAG 2 (12.5) | Quencher 1 (1.50) | Water-repellent Polymer 4 (6) | PGMEA (2,000) | CyH (500) |
| 2-16 | R-16 | Resist Polymer 6 (100) | PAG 2 (12.5) | Quencher 1 (1.50) | Water-repellent Polymer 5 (6) | PGMEA (2,000) | CyH (500) |
| 2-17 | R-17 | Resist Polymer 12 (100) | PAG 2 (12.5) | Quencher 1 (1.50) | Water-repellent Polymer 5 (6) | PGMEA (2,000) | CyH (500) |
| 2-18 | R-18 | Resist Polymer 13 (100) | PAG 2 (12.5) | Quencher 1 (1.50) | Water-repellent Polymer 5 (6) | PGMEA (2,000) | CyH (500) |
| 2-19 | R-19 | Resist Polymer 1 (100) | PAG 2 (12.5) | Quencher 2 (1.40) | Water-repellent Polymer 5 (6) | PGMEA (2,000) | CyH (500) |
| 2-20 | R-20 | Resist Polymer 1 (80) Comparative Polymer 1 (20) | PAG 2 (12.5) | Quencher 2 (1.40) | Water-repellent Polymer 5 (6) | PGMEA (2,000) | CyH (500) |
| 2-21 | R-21 | Resist Polymer 14 (100) | PAG 2 (12.5) | Quencher 1 (1.50) | Water-repellent Polymer 5 (6) | PGMEA (2,000) | CyH (500) |
| 2-22 | R-22 | Resist Polymer 15 (100) | PAG 2 (12.5) | Quencher 1 (1.50) | Water-repellent Polymer 5 (6) | PGMEA (2,000) | CyH (500) |
| 2-23 | R-23 | Resist Polymer 15 (50) Blend Resist Polymer 1 (50) | PAG 2 (12.5) | Quencher 1 (1.50) | Water-repellent Polymer 5 (6) | PGMEA (2,000) | CyH (500) |

TABLE 3

| | | Resist | Polymer (pbw) | Acid generator (pbw) | Basic compound (pbw) | Additive (pbw) | Solvent 1 (pbw) | Solvent 2 (pbw) |
|---|---|---|---|---|---|---|---|---|
| Comparative Example | 2-1 | RF-01 | Comparative Polymer 1 (100) | PAG 2 (12.5) | Quencher 1 (1.50) | — | PGMEA (2,000) | CyH (500) |
| | 2-2 | RF-02 | Comparative Polymer 2 (100) | PAG 2 (12.5) | Quencher 1 (1.50) | — | PGMEA (2,000) | CyH (500) |
| | 2-3 | RF-03 | Comparative Polymer 3 (100) | PAG 2 (12.5) | Quencher 1 (1.50) | — | PGMEA (2,000) | CyH (500) |
| | 2-4 | RF-04 | Comparative Polymer 4 (100) | PAG 2 (12.5) | Quencher 1 (1.50) | — | PGMEA (2,000) | CyH (500) |
| | 2-5 | RF-05 | Comparative Polymer 2 (100) | PAG 2 (12.5) | Quencher 1 (1.50) | Water-repellent Polymer 4 (6) | PGMEA (2,000) | CyH (500) |

TABLE 4

| Protective Film | Polymer (pbw) | Additive (pbw) | Organic solvent (pbw) |
|---|---|---|---|
| TC-1 | TC Polymer 1 (100) | tri-n-octylamine (0.5) | diisoamyl ether (2,700) 2-methyl-1-butanol (270) |
| TC-2 | TC Polymer 2 (100) | tri-n-octylamine (0.5) | diisoamyl ether (2,700) 2-methyl-1-butanol (270) |
| TC-3 | TC Polymer 3 (100) | — | diisoamyl ether (2,700) 2-methyl-1-butanol (270) |
| TC-4 | TC Polymer 2 (80) TC Polymer 4 (20) | — | diisoamyl ether (2,700) 2-methyl-1-butanol (270) |
| TC-5 | TC Polymer 5 (80) TC Polymer 4 (20) | — | diisoamyl ether (2,700) 2-methyl-1-butanol (270) |
| Comparative TC-1 | TC Polymer 1 (100) | — | diisoamyl ether (2,700) 2-methyl-1-butanol (270) |
| Comparative TC-2 | TC Polymer 6 (100) | — | diisoamyl ether (2,700) 2-methyl-1-butanol (270) |

TABLE 5

| | Resist | Protective film | PEB temp. (°C.) | Dose (mJ/cm$^2$) | Hole size variation 3σ (nm) |
|---|---|---|---|---|---|
| Example 3-1 | R-01 | TC-1 | 90 | 35.0 | 1.9 |
| Example 3-2 | R-02 | TC-1 | 80 | 32.0 | 2.0 |

TABLE 5-continued

| | Resist | Protective film | PEB temp. (° C.) | Dose (mJ/cm²) | Hole size variation 3σ (nm) |
|---|---|---|---|---|---|
| Example 3-3 | R-03 | TC-1 | 95 | 37.0 | 2.1 |
| Example 3-4 | R-04 | TC-1 | 90 | 34.0 | 1.9 |
| Example 3-5 | R-05 | TC-1 | 100 | 33.0 | 2.2 |
| Example 3-6 | R-06 | TC-1 | 95 | 35.0 | 2.2 |
| Example 3-7 | R-07 | TC-1 | 95 | 39.0 | 2.2 |
| Example 3-8 | R-08 | TC-1 | 95 | 34.0 | 2.3 |
| Example 3-9 | R-09 | TC-1 | 95 | 38.0 | 1.9 |
| Example 3-10 | R-10 | TC-1 | 95 | 33.0 | 1.8 |
| Example 3-11 | R-11 | TC-1 | 105 | 40.0 | 1.9 |
| Example 3-12 | R-06 | TC-2 | 100 | 40.0 | 2.0 |
| Example 3-13 | R-06 | TC-3 | 100 | 35.0 | 2.0 |
| Example 3-14 | R-06 | TC-4 | 100 | 35.0 | 2.3 |
| Example 3-15 | R-06 | TC-5 | 100 | 36.0 | 2.2 |
| Example 3-16 | R-12 | — | 95 | 37.0 | 2.9 |
| Example 3-17 | R-13 | — | 95 | 37.0 | 3.0 |
| Example 3-18 | R-14 | — | 95 | 36.0 | 3.1 |
| Example 3-19 | R-15 | — | 95 | 33.0 | 3.2 |
| Example 3-20 | R-16 | — | 95 | 32.0 | 3.4 |
| Example 3-21 | R-17 | — | 95 | 34.0 | 3.4 |
| Example 3-22 | R-18 | — | 95 | 38.0 | 3.5 |
| Example 3-23 | R-19 | — | 95 | 33.0 | 3.2 |
| Example 3-24 | R-20 | — | 95 | 40.0 | 3.7 |
| Example 3-25 | R-21 | — | 90 | 38.0 | 3.5 |
| Example 3-26 | R-22 | — | 95 | 33.0 | 3.5 |
| Example 3-27 | R-23 | — | 90 | 40.0 | 3.9 |
| Comparative Example 3-1 | RF-01 | TC-1 | 110 | 44.0 | 5.9 |
| Comparative Example 3-2 | RF-02 | TC-1 | 105 | 58.0 | 3.9 |
| Comparative Example 3-3 | RF-03 | TC-1 | 110 | 39.0 | 5.4 |
| Comparative Example 3-4 | RF-04 | — | 110 | 56.0 | 5.6 |
| Comparative Example 3-5 | R-04 | Comparative TC-1 | 90 | 50.0 | 3.4 |
| Comparative Example 3-6 | R-04 | Comparative TC-2 | 90 | 50.0 | Holes not opened |
| Comparative Example 3-7 | RF-03 | TC-1 | 95 | 60.0 | 4.8 |

ArF Lithography Patterning Test 3

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-01, R-02, RF-01 or RF-02) shown in Tables 2 and 3 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Figure 19:
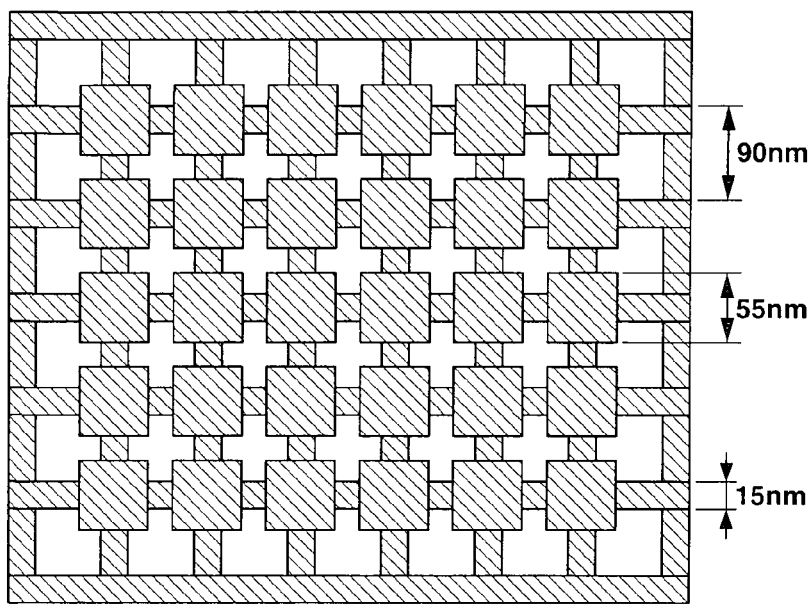
FIG. 19 illustrates a lattice-like mask with dots disposed at intersections, used in ArF lithography patterning test 3.

Using an ArF excimer laser immersion lithography scanner NSR-610C (Nikon Corp., NA 1.30, σ 0.98/0.78, cross-pole opening 20 deg., azimuthally polarized illumination), exposure was performed through a 6% halftone phase shift mask bearing a lattice-like pattern with a pitch of 90 nm and a line width of 15 nm (on-wafer size) having dots disposed at intersections, whose layout is shown in FIG. 19, while the dose and focus were varied. After the exposure, the wafer was baked (PEB) at the temperature shown in Table 6 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of 50 holes was measured, from which a size variation 3σ was determined. The results are shown in Table 6.

TABLE 6

| | Resist | PEB temp. (° C.) | Dose (mJ/cm²) | Hole size variation 3σ (nm) |
|---|---|---|---|---|
| Example 4-1 | R-01 | 90 | 40 | 2.0 |
| Example 4-2 | R-02 | 80 | 41 | 2.0 |
| Comparative Example 4-1 | RF-01 | 110 | 115 | 4.7 |
| Comparative Example 4-2 | RF-02 | 105 | 105 | 5.1 |

ArF Lithography Patterning Test 4

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-01, R-02, RF-01 or RF-02) shown in Tables 2 and 3 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Figure 20:
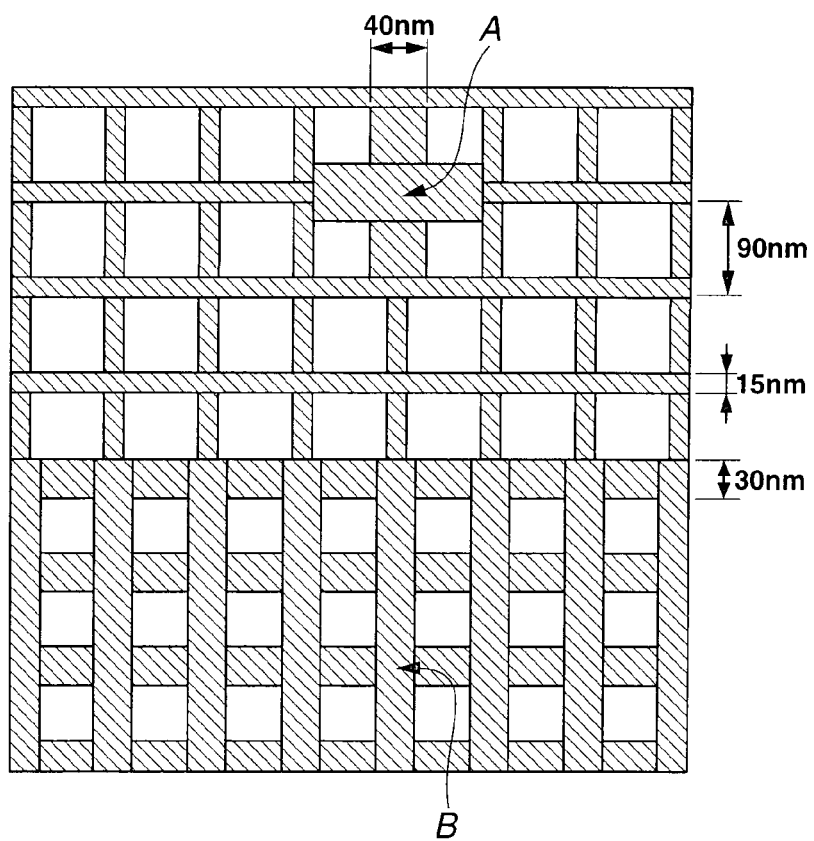
FIG. 20 illustrates a mask bearing a lattice-like pattern with thick gratings disposed thereon, used in ArF lithography patterning test 4.

Using an ArF excimer laser immersion lithography scanner NSR-610C (Nikon Corp., NA 1.30, σ 0.98/0.78, cross-pole opening 20 deg., azimuthally polarized illumination), exposure was performed through a 6% halftone phase shift mask bearing a lattice-like pattern with a pitch of 90 nm (on-wafer size) having thick gratings disposed at intersections whose layout is shown in FIG. 20, while the dose was varied. After the exposure, the wafer was baked (PEB) at the temperature shown in Table 7 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of holes at positions A and B on the mask (FIG. 20) was measured. The results are shown in Table 7.

TABLE 7

| | Resist | PEB temp. (° C.) | Dose (mJ/cm²) | Hole size at A (nm) | Hole size at B (nm) |
|---|---|---|---|---|---|
| Example 5-1 | R-01 | 90 | 41 | 39 | 40 |
| Example 5-2 | R-02 | 80 | 43 | 39 | 41 |
| Comparative Example 5-1 | RF-01 | 110 | 90 | 23 | 51 |
| Comparative Example 5-2 | RF-02 | 105 | 85 | 21 | 50 |

ArF Lithography Patterning Test 5

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A941 having a silicon content of 43 wt % was deposited thereon to a thickness of 35 nm. On this substrate for trilayer process, the resist composition (R-01, R-02, RF-01 or RF-02) shown in Tables 2 and 3 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Using an ArF excimer laser immersion lithography scanner NSR-610C (Nikon Corp., NA 1.30, σ 0.98/0.78, dipole opening 20 deg., azimuthally polarized illumination), exposure was performed through a 6% halftone phase shift mask bearing a lattice-like pattern with a pitch of 90 nm and a line width of 30 nm (on-wafer size) whose layout is shown in FIG. 18 while the dose was varied. The same area was subjected to two continuous exposures by X and Y dipole illuminations. After the exposure, the wafer was baked (PEB) at the temperature shown in Table 8 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of 50 holes was measured, from which a size variation 3σ was determined. The results are shown in Table 8.

TABLE 8

|  | Resist | PEB temp. (° C.) | Dose (mJ/cm$^2$) | Hole size variation 3σ (nm) |
| --- | --- | --- | --- | --- |
| Example 6-1 | R-01 | 90 | 15 | 1.7 |
| Example 6-2 | R-02 | 80 | 18 | 1.8 |
| Comparative Example 6-1 | RF-01 | 110 | 22 | 3.1 |
| Comparative Example 6-2 | RF-02 | 105 | 20 | 3.2 |

ArF Lithography Patterning Test 6

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-01, R-02, RF-01 or RF-02) shown in Tables 2 and 3 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Using an ArF excimer laser immersion lithography scanner NSR-610C (Nikon Corp., NA 1.30, σ 0.98/0.78, dipole opening 20 deg., azimuthally polarized illumination), exposure was performed through a 6% halftone phase shift mask bearing a lattice-like pattern with a pitch of 90 nm and a line width of 15 nm (on-wafer size) having dots disposed at intersections, whose layout is shown in FIG. 19, while the dose was varied. The same area was subjected to two continuous exposures by X and Y dipole illuminations. After the exposure, the wafer was baked (PEB) at the temperature shown in Table 9 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of holes was measured, from which a focus margin affording a size of 40 nm±5 nm was determined as DOF. The size of 50 holes within a shot of the same dose and the same focus was measured, from which a size variation 3σ was determined. The results are shown in Table 9.

TABLE 9

|  | Resist | PEB temp. (° C.) | Dose (mJ/cm$^2$) | DOF (nm) | Hole size variation 3σ (nm) |
| --- | --- | --- | --- | --- | --- |
| Example 7-1 | R-01 | 90 | 23 | 110 | 2.2 |
| Example 7-2 | R-02 | 80 | 25 | 100 | 2.1 |
| Comparative Example 7-1 | RF-01 | 110 | 33 | 30 | 3.6 |
| Comparative Example 7-2 | RF-02 | 105 | 35 | 20 | 3.0 |

ArF Lithography Patterning Test 7

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-01, R-02, RF-01 or RF-02) shown in Tables 2 and 3 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Using an ArF excimer laser immersion lithography scanner NSR-610C (Nikon Corp., NA 1.30, σ 0.98/0.78, cross-pole opening 20 deg., azimuthally polarized illumination), exposure was performed through a 6% halftone phase shift mask bearing a dot pattern with a pitch of 90 nm and a width of 55 nm (on-wafer size) whose layout is shown in FIG. 7, while the dose was varied. After the exposure, the wafer was baked (PEB) at the temperature shown in Table 10 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of holes was measured, from which a focus margin affording a size of 40 nm±5 nm was determined as DOF. The size of 50 holes within a shot of the same dose and the same focus was measured, from which a size variation 3σ was determined. The results are shown in Table 10.

TABLE 10

| | Resist | PEB temp. (° C.) | Dose (mJ/cm$^2$) | DOF (nm) | Hole size variation 3σ (nm) |
|---|---|---|---|---|---|
| Example 8-1 | R-01 | 90 | 21 | 100 | 3.2 |
| Example 8-2 | R-02 | 80 | 29 | 95 | 3.1 |
| Comparative Example 8-1 | RF-01 | 110 | 33 | 15 | 5.6 |
| Comparative Example 8-2 | RF-02 | 105 | 34 | 10 | 5.0 |

TABLE 11

| | Resist | PEB temp. (° C.) | Dose (mJ/cm$^2$) | DOF (nm) | Hole size variation 3σ (nm) |
|---|---|---|---|---|---|
| Example 9-1 | R-01 | 90 | 22 | 105 | 2.0 |
| Example 9-2 | R-02 | 80 | 24 | 100 | 2.0 |
| Comparative Example 9-1 | RF-01 | 110 | 33 | 20 | 3.4 |
| Comparative Example 9-2 | RF-02 | 105 | 35 | 15 | 2.9 |

ArF Lithography Patterning Test 8

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-01, R-02, RF-01 or RF-02) shown in Tables 2 and 3 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Using an ArF excimer laser immersion lithography scanner NSR-610C (Nikon Corp., NA 1.30, σ 0.98/0.78, dipole opening 20 deg., azimuthally polarized illumination), exposure was performed through a 6% halftone phase shift mask bearing a dot pattern with a pitch of 90 nm and a width of 55 nm (on-wafer size) whose layout is shown in FIG. 7, while the dose was varied. The same area was subjected to two continuous exposures by X and Y dipole illuminations. After the exposure, the wafer was baked (PEB) at the temperature shown in Table 11 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of holes was measured, from which a focus margin affording a size of 40 nm±5 nm was determined as DOF. The size of 50 holes within a shot of the same dose and the same focus was measured, from which a size variation 3σ was determined. The results are shown in Table 11.

ArF Lithography Patterning Test 9

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition R-01 shown in Table 2 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Using an ArF excimer laser immersion lithography scanner NSR-610C (Nikon Corp., NA 1.30, σ 0.98/0.78, dipole opening 20 deg., azimuthally polarized illumination), exposure was performed through a 6% halftone phase shift mask bearing a dot pattern with a pitch of 90 nm and a width of 55 nm (on-wafer size) whose layout is shown in FIG. 7, while the dose was varied. The same area was subjected to two continuous exposures by X and Y dipole illuminations. After the exposure, the wafer was baked (PEB) at the temperature shown in Table 12 for 60 seconds and developed. Specifically, the solvent shown in Table 12 was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of holes was measured, from which a focus margin affording a size of 40 nm±5 nm was determined as DOF. The size of 50 holes within a shot of the same dose and the same focus was measured, from which a size variation 3σ was determined. The results are shown in Table 12.

TABLE 12

| | Resist | PEB temp. (° C.) | Dose (mJ/cm$^2$) | Developer | DoF (nm) | Hole size variation 3σ (nm) |
|---|---|---|---|---|---|---|
| Example 10-1 | R-01 | 90 | 25 | 2-heptanone | 105 | 2.0 |
| Example 10-2 | R-01 | 90 | 24 | methyl benzoate | 110 | 2.3 |
| Example 10-3 | R-01 | 90 | 23 | ethyl benzoate | 105 | 2.0 |
| Example 10-4 | R-01 | 90 | 28 | phenyl acetate | 100 | 2.2 |
| Example 10-5 | R-01 | 90 | 24 | benzyl acetate | 100 | 2.2 |
| Example 10-6 | R-01 | 90 | 24 | methyl phenylacetate | 100 | 2.4 |
| Example 10-7 | R-01 | 90 | 26 | methyl benzoate:butyl acetate = 6:4 | 100 | 2.5 |
| Example 10-8 | R-01 | 90 | 25 | methyl benzoate:2-heptanone = 5:5 | 100 | 2.3 |

ArF Lithography Patterning Test 10

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-01, R-02, RF-01 or RF-02) shown in Tables 2 and 3 was spin coated, then baked on a hot plate at 100° C. for 60 seconds to form a resist film of 100 nm thick. The protective film-forming composition TC-1 shown in Table 4 was spin coated on the resist film and baked at 90° C. for 60 seconds to form a protective film (or topcoat) of 50 nm thick.

Using an ArF excimer laser immersion lithography scanner NSR-610C (Nikon Corp., NA 1.30, σ 0.98/0.78, dipole opening 20 deg., azimuthally polarized illumination), first exposure was performed through a 6% halftone phase shift mask bearing an array of X-direction lines with a pitch of 80 nm and a line width of 40 nm (on-wafer size) by compliant dipole illumination. Next, second exposure was performed through a 6% halftone phase shift mask bearing an array of Y-direction lines with a pitch of 80 nm and a line width of 40 nm (on-wafer size) by compliant dipole illumination. After the exposure, the wafer was baked (PEB) at the temperature shown in Table 13 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid.

A hole pattern resulted from image reversal by solvent development. By observation under TDSEM S-9380, the size of holes was measured, from which a focus margin affording a size of 40 nm±5 nm was determined as DOF. The size of 50 holes within a shot of the same dose and the same focus was measured, from which a size variation 3σ was determined. The results are shown in Table 13.

TABLE 13

| | Resist | PEB temp. (° C.) | Dose (mJ/cm$^2$) | DOF (nm) | Hole size variation 3σ (nm) |
|---|---|---|---|---|---|
| Example 11-1 | R-01 | 90 | 16 | 105 | 1.6 |
| Example 11-2 | R-02 | 80 | 18 | 100 | 1.5 |
| Comparative Example 11-1 | RF-01 | 110 | 21 | 20 | 2.8 |
| Comparative Example 11-2 | RF-02 | 105 | 22 | 15 | 2.0 |

It is seen from the results of Tables 5 to 13 that the resist compositions within the scope of the invention display improved resolution, sensitivity, and dimensional uniformity upon organic solvent development.

Japanese Patent Application No. 2010-067769 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An acetal compound which is one selected from the group consisting of the following formulae:

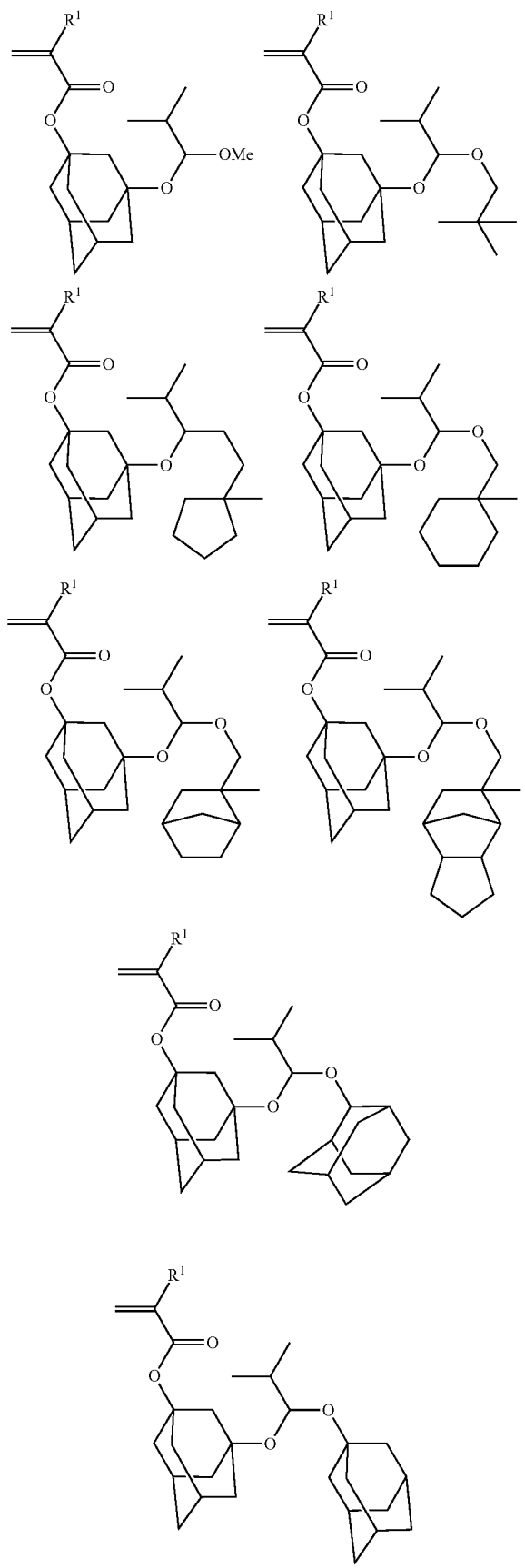

125
-continued
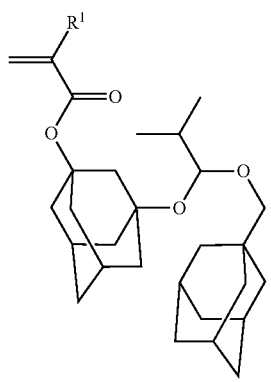
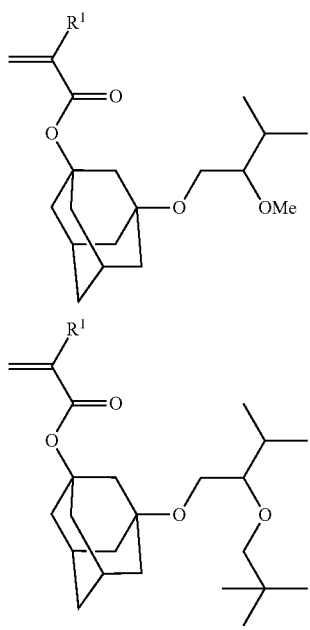
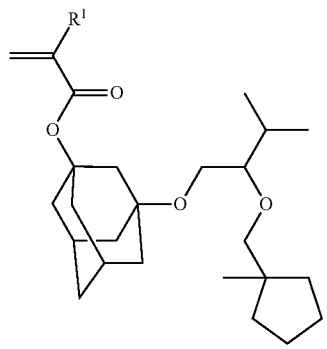
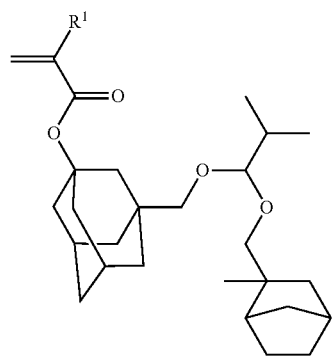
126
-continued
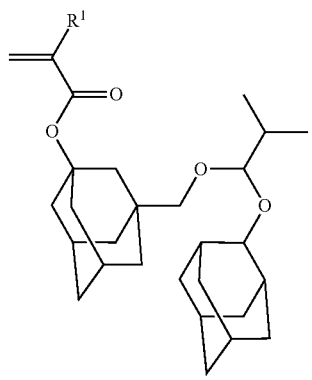
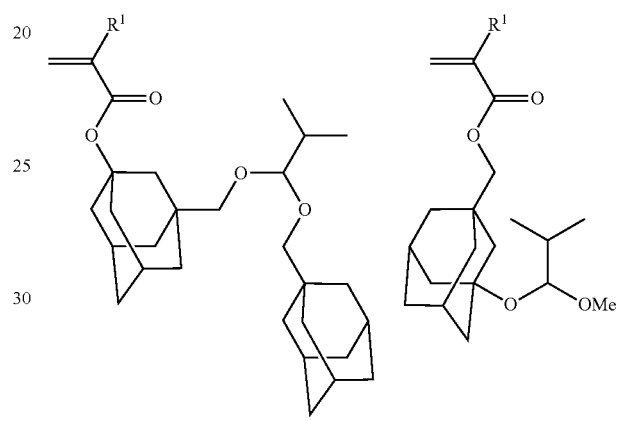
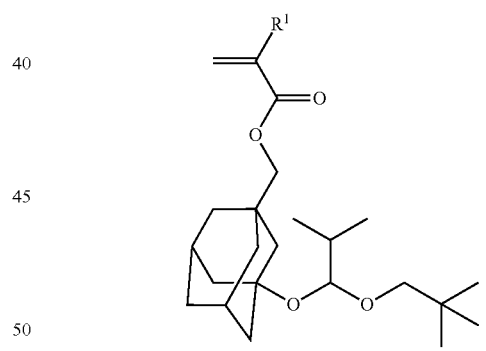
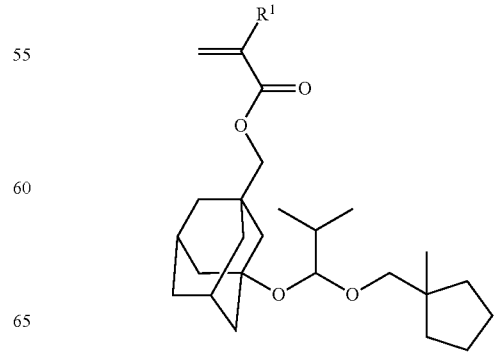

127
-continued
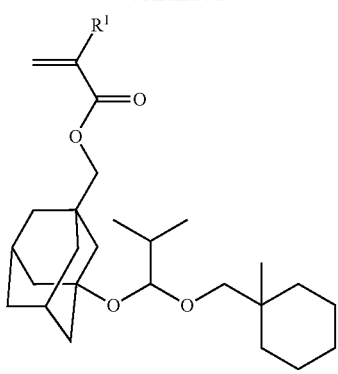
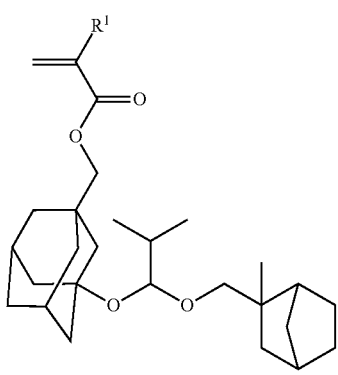
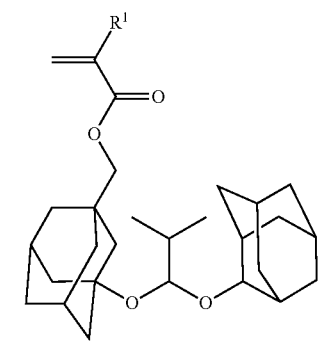
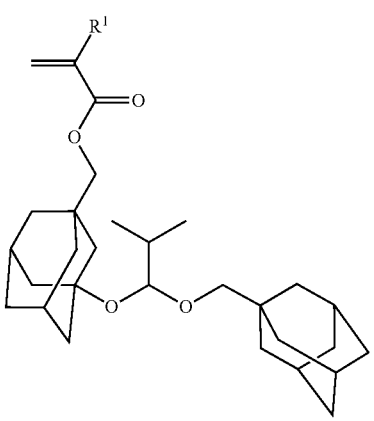
128
-continued
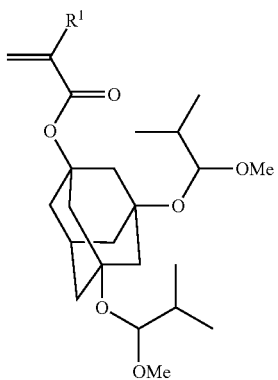
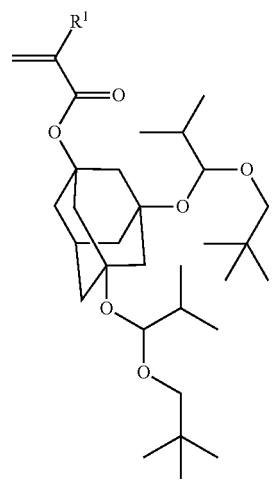
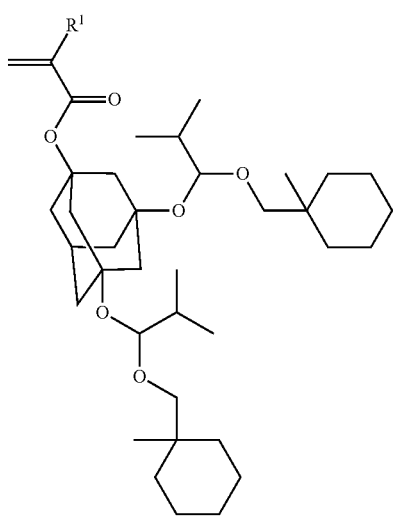

129
-continued
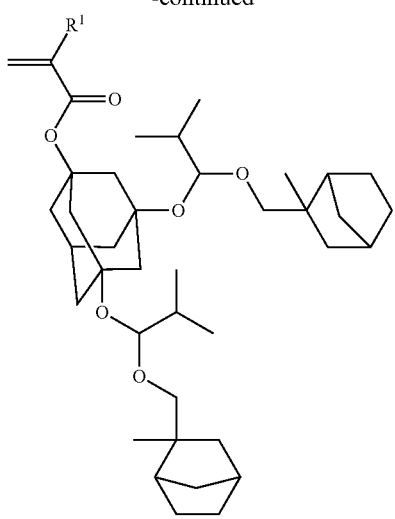
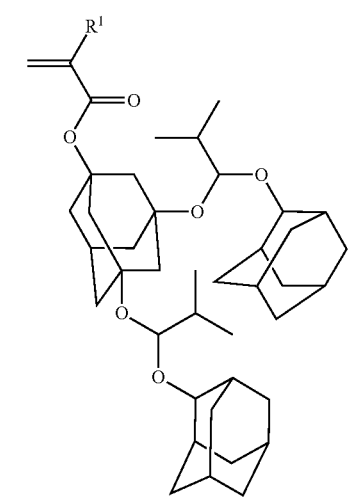
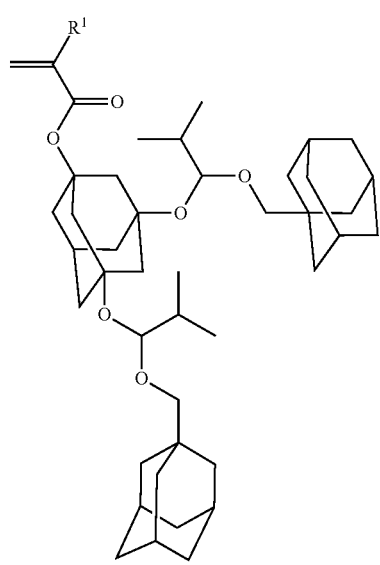
130
-continued
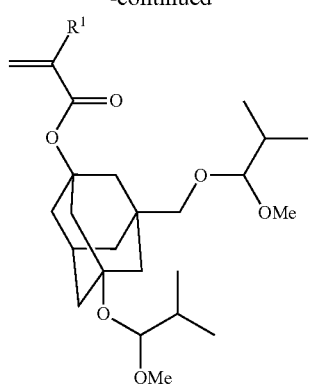
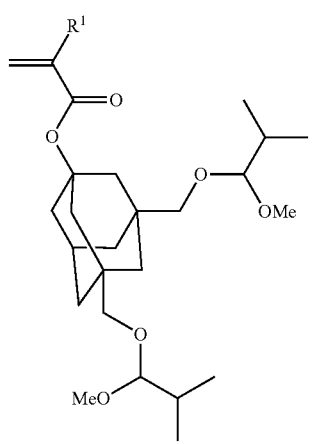
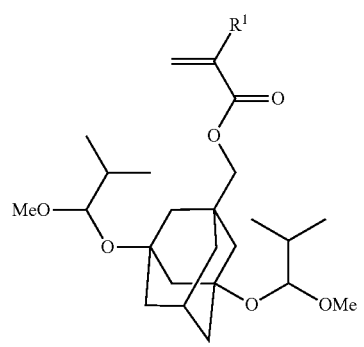
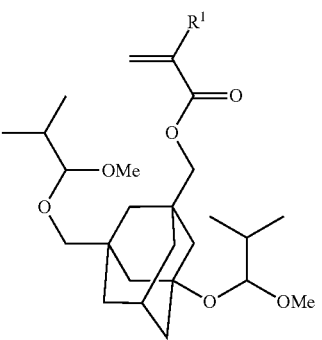

-continued
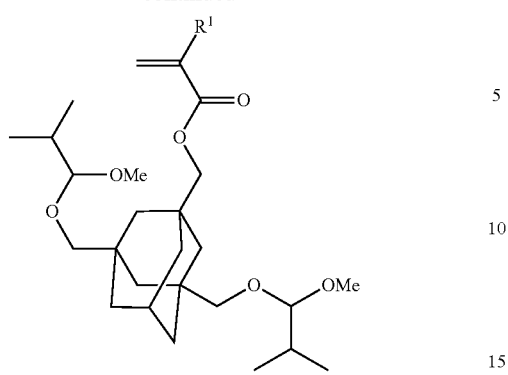
wherein R¹ is hydrogen, methyl or trifluoromethyl.
2. A polymer comprising recurring units being one derived from an acetal compound selected from the group consisting of the following formulae:
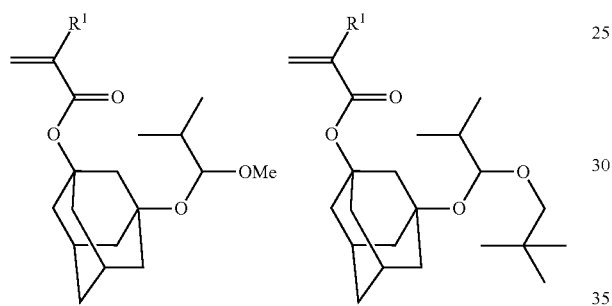
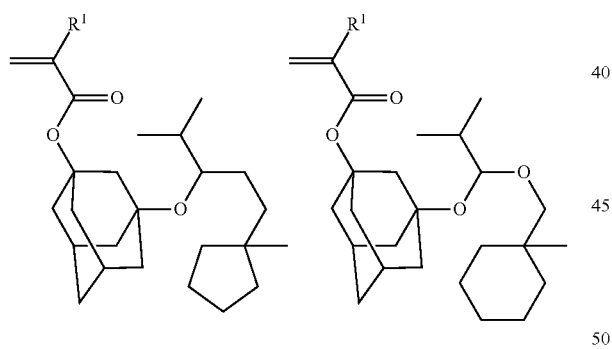
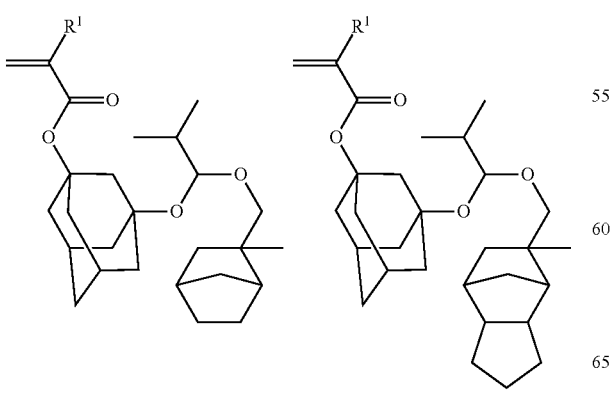
-continued
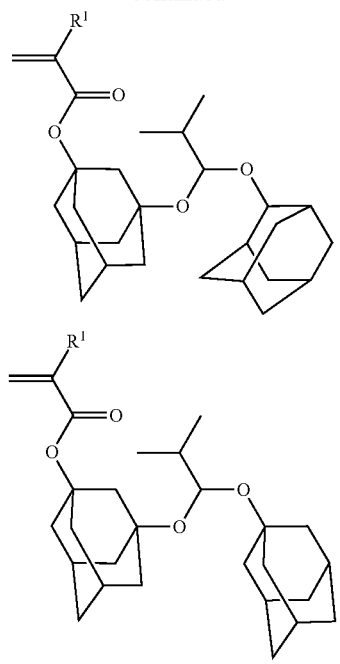
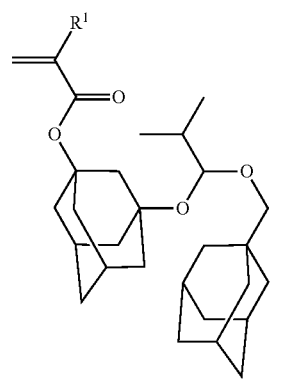
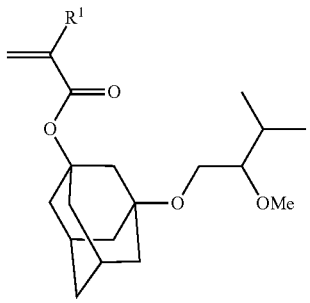
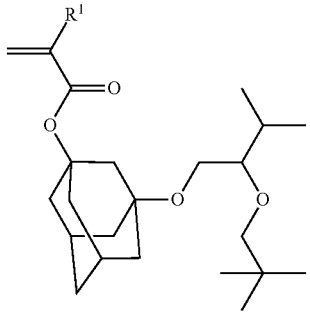

133
-continued
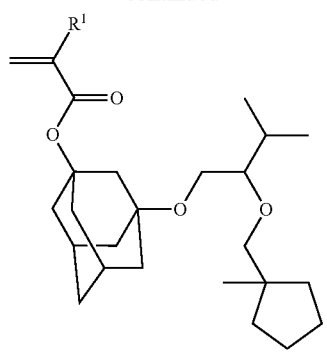
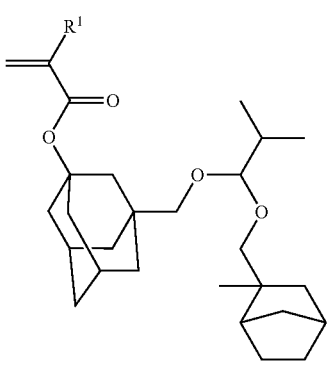
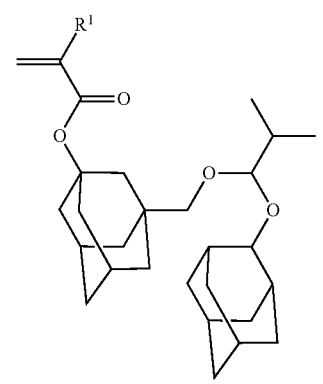
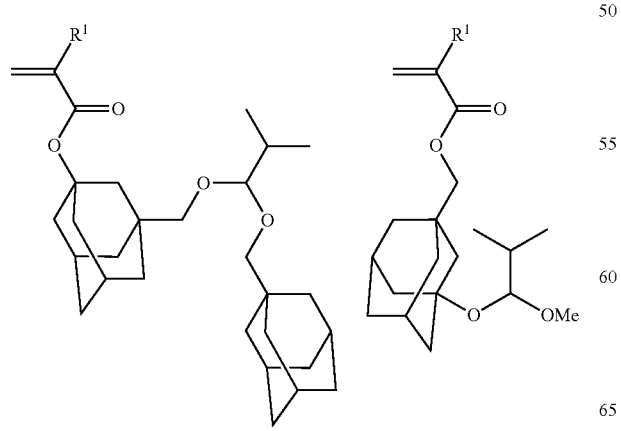
134
-continued
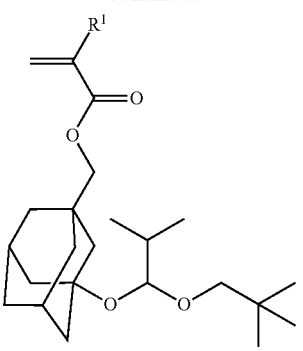
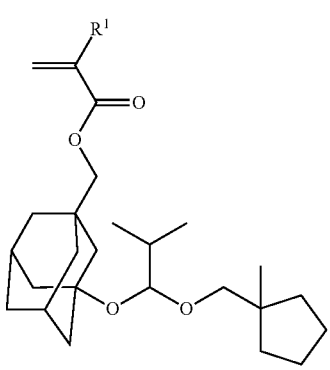
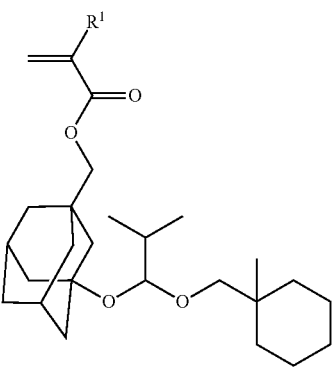
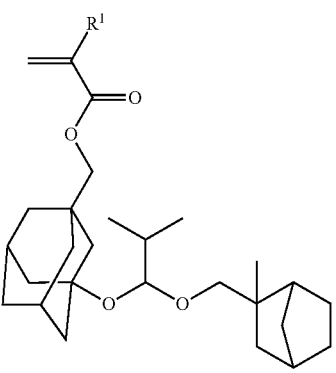

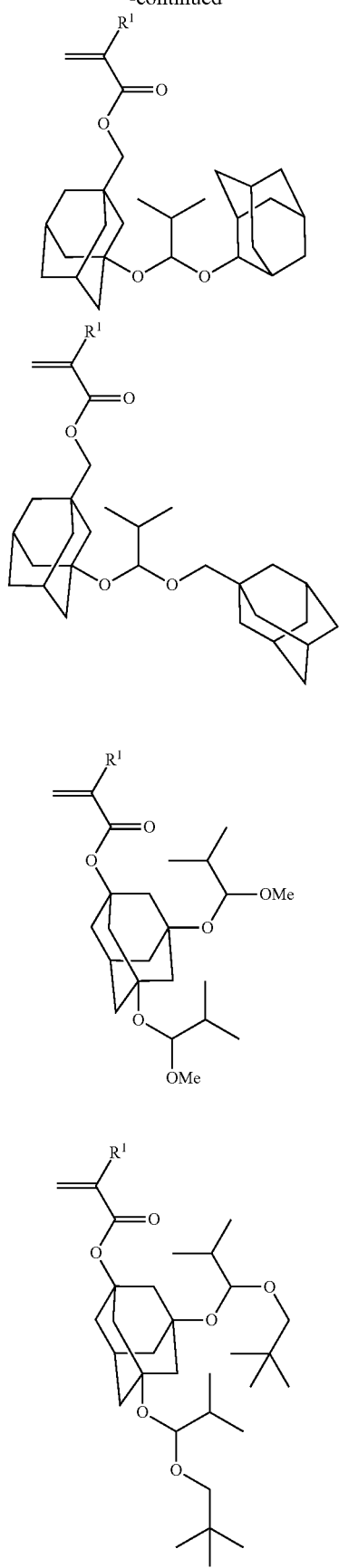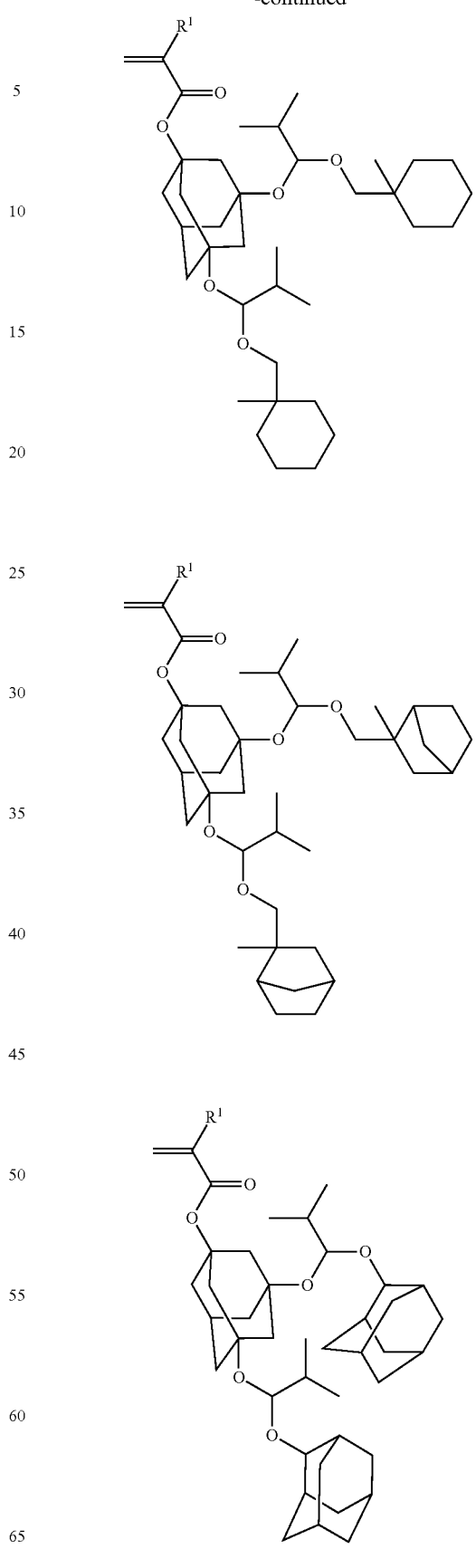

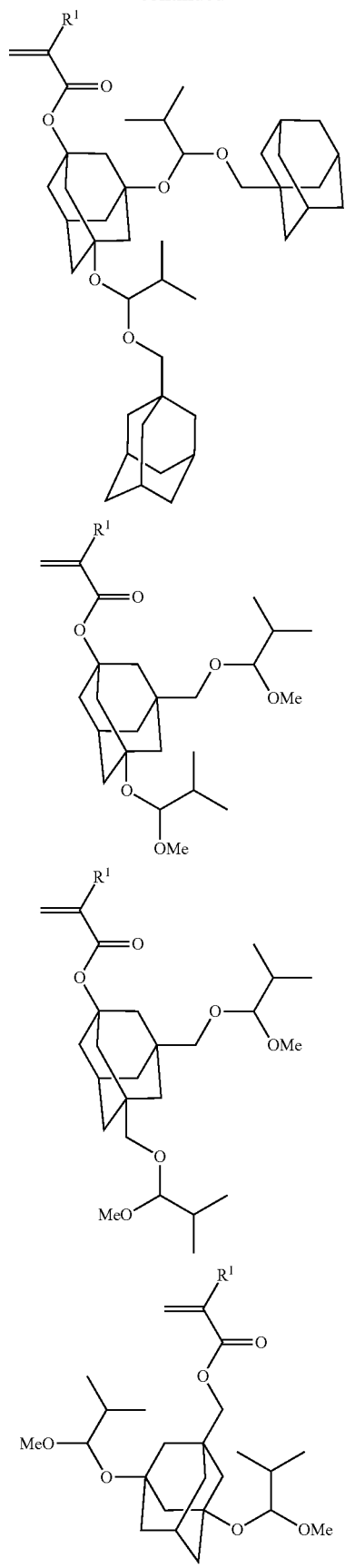
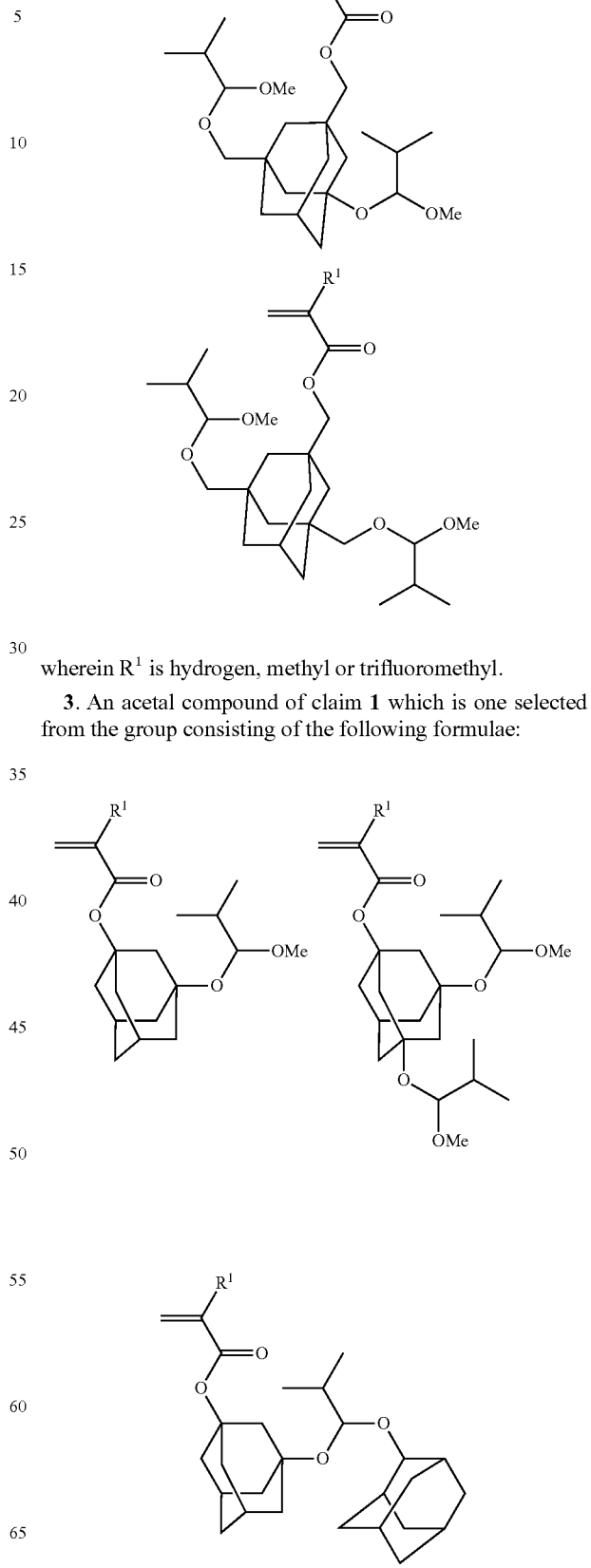
wherein R¹ is hydrogen, methyl or trifluoromethyl.
3. An acetal compound of claim 1 which is one selected from the group consisting of the following formulae:

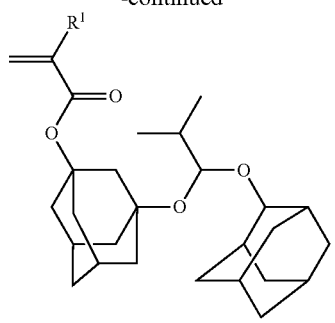
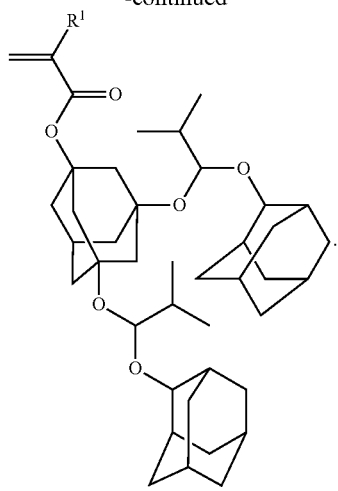
4. A polymer of claim 2 wherein the acetal compound is selected from the group consisting of the following formulae:
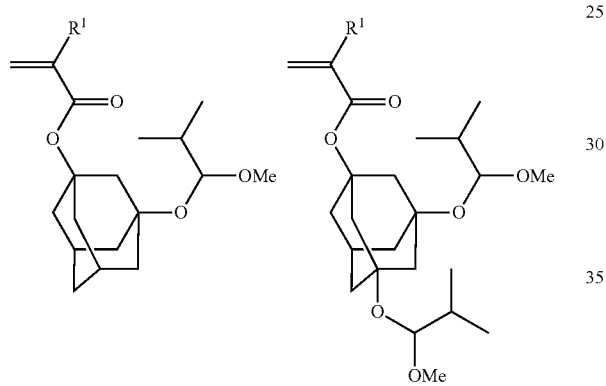
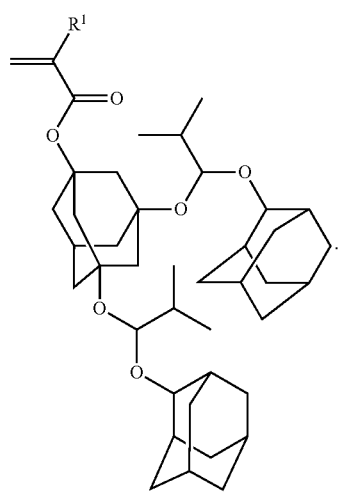
* * * * *